US009206156B2

(12) United States Patent
Schunk et al.

(10) Patent No.: US 9,206,156 B2
(45) Date of Patent: *Dec. 8, 2015

(54) SUBSTITUTED INDOLE DERIVATIVES

(71) Applicants: Stefan Schunk, Aachen (DE); Stefan Oberbörsch, Aachen (DE); Werner Englberger, Stolberg (DE); Bernd Sundermann, Friedrichsdorf (DE)

(72) Inventors: Stefan Schunk, Aachen (DE); Stefan Oberbörsch, Aachen (DE); Werner Englberger, Stolberg (DE); Bernd Sundermann, Friedrichsdorf (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/710,604

(22) Filed: Dec. 11, 2012

(65) Prior Publication Data

US 2013/0116283 A1    May 9, 2013

Related U.S. Application Data

(63) Continuation of application No. 12/388,977, filed on Feb. 19, 2009, now abandoned.

(30) Foreign Application Priority Data

Feb. 22, 2008 (EP) .................................. 08003238

(51) Int. Cl.
C07D 401/12 (2006.01)
C07D 401/14 (2006.01)
C07D 409/14 (2006.01)

(52) U.S. Cl.
CPC ............ C07D 401/12 (2013.01); C07D 401/14 (2013.01); C07D 409/14 (2013.01)

(58) Field of Classification Search
CPC .. C07D 209/04; C07D 209/60; C07D 209/62; C07D 209/70; C07D 401/12; C07D 401/14; C07D 409/14
USPC .................................. 514/323; 546/200, 201
See application file for complete search history.

(56) References Cited

U.S. PATENT DOCUMENTS

| 6,107,329 | A | 8/2000 | Hover et al. |
| 2004/0225003 | A1 | 11/2004 | Sattlegger et al. |
| 2005/0261358 | A1 | 11/2005 | Hinze et al. |
| 2005/0277674 | A1 | 12/2005 | Hinze et al. |
| 2007/0219214 | A1 | 9/2007 | Jasserand et al. |

FOREIGN PATENT DOCUMENTS

| AR | 070398 A1 | 3/2010 |
| AU | 2009216920 A1 | 8/2009 |
| CA | 2716270 A1 | 8/2009 |
| CN | 102015683 A | 4/2011 |
| EP | 2254883 A1 | 12/2010 |
| JP | 2009 525308 A | 7/2009 |
| JP | 2011512374 A | 4/2011 |
| MX | 2010009045 A | 9/2010 |
| PE | 14902009 A1 | 9/2009 |
| WO | 03 037863 | 5/2003 |
| WO | 2004 043909 | 5/2004 |
| WO | 2004 043949 | 5/2004 |
| WO | WO 2005047253 A1 * | 5/2005 |
| WO | WO 2007/088181 A1 | 8/2007 |
| WO | 2008 119741 A2 | 10/2008 |
| WO | 2009 103552 A1 | 8/2009 |

OTHER PUBLICATIONS

Meunier, Jean-Claude et al; "Isolation and structure of the endogenous agonist of opioid receptor-like ORL1 receptor"; Nature, vol. 377, Oct. 1995; pp. 532-535.
Reinscheid, Rainer K, et al; "Orphanin FQ: A neuropepetide that activates an opioidlike G protein-coupled receptor"; Science, vol. 270, Nov. 1995, pp. 792-794.
Mogil, J.S., et al; "Orphanin FQ is a functional anti-opioid peptide"; Neuroscience, vol. 75, No. 2, 1996, pp. 333-337.
Jenck, Francois, et al; "Orphanin FQ acts as an anxiolytic to attenuate behavioral responses to stress"; Proc. Natyl. Acad. Sci. USA, vol. 94, Dec. 1997, pp. 14854-14858.
King, Michael A, et al; "Spinal analgesic activity of orphanin FQ/nociceptin and its fragments"; Neuroscience Letters 223, 1997, pp. 113-116.
Abdulla, Fuad A., et al; "Axotomy reduces the effect of analgesi opioids yet increases the effect of nociceptin on dorsal root ganglion neurons"; The Journal of Neuroscience, 18 (23), Dec. 1, 1998, pp. 9685-9694.
Nishi, Miyuki, et al; "Unrestrained nociceptive response and disregulation of hearing ability in mice lacking the nociceptin/orphaninFQ receptor"; The EMBO Journal, vol. 16, No. 8, 1997, pp. 1858-1864.
Manabe, Toshiya, et al; "Facilitation of long-term potentiation and memory in mice lacking nociceptin receptors"; Nature, vol. 394, Aug. 1998, pp. 577-581.
Calo, Girolamo, et al; "Pharmacology of nociceptin and its receptor: a novel therapeutic target"; British Journal of Pharmacology, 129, 2000, pp. 1261-1283.

* cited by examiner

*Primary Examiner* — Sarah Pihonak
(74) *Attorney, Agent, or Firm* — Norris McLaughlin & Marcus, P.A.

(57) ABSTRACT

Substituted indole derivatives, processes for the preparation thereof, medicinal products and pharmaceutical compositions containing these compounds and the use of substituted indole derivatives to treat pain and other conditions and for other medical purposes.

14 Claims, No Drawings

SUBSTITUTED INDOLE DERIVATIVES

This application is a continuation of U.S. patent application Ser. No. 12/388,977, filed Feb. 19, 2009, which claims priority of European Patent Application No. 080003238.6, filed on Feb. 22, 2008, the disclosures of which patent applications are incorporated herein by reference.

The present invention relates to substituted indole derivatives, processes for the preparation thereof, medicinal products containing these compounds and the use of substituted indole derivatives for the preparation of medicinal products.

The heptadecapeptide nociceptin is an endogenous ligand of the ORL1 (opioid receptor-like) receptor (Meunier et al., Nature 377, 1995, p. 532-535), which belongs to the family of opioid receptors, is to be found in many regions of the brain and spinal cord, and has a high affinity for the ORL1 receptor. The ORL1 receptor is homologous to the μ, κ and δ opioid receptors and the amino acid sequence of the nociceptin peptide displays a strong similarity to those of the known opioid peptides. The activation of the receptor induced by nociceptin leads via the coupling with $G_{i/o}$ proteins to an inhibition of the adenylate cyclase (Meunier et al., Nature 377, 1995, p. 532-535).

After intercerebroventicular application, the nociceptin peptide exhibits pronociceptive and hyperalgesic activity in various animal models (Reinscheid et al., Science 270, 1995, p. 792-794). These findings can be explained as an inhibition of stress-induced analgesia (Mogil et al., Neuroscience 75, 1996, p. 333-337). Anxiolytic activity of the nociceptin could also be demonstrated in this connection, (Jenck et al., Proc. Natl. Acad. Sci. USA 94, 1997, 14854-14858).

On the other hand, an antinociceptive effect of nociceptin could also be demonstrated in various animal models, in particular after intrathaecal application. Nociceptin has an antinociceptive effect in various pain models, for example in the tail flick test in mice (King et al., Neurosci. Lett., 223, 1997, 113-116). In models of neuropathic pain, an antinociceptive effect of nociceptin could likewise be detected and was particularly beneficial since the effectiveness of nociceptin increases after axotomy of spinal nerves. This contrasts with conventional opioids, the effectiveness of which decreases under these conditions (Abdulla and Smith, J. Neurosci., 18, 1998, p. 9685-9694).

The ORL1 receptor is also involved in the regulation of further physiological and patho-physiological processes. These include inter alia learning and memory (Manabe et al., Nature, 394, 1997, p. 577-581), hearing capacity (Nishi et al., EMBO J., 16, 1997, p. 1858-1864) and numerous further processes. A synopsis by Calo et al. (Br. J. Pharmacol., 129, 2000, 1261-1283) gives an overview of the indications or biological processes in which the ORL1-receptor plays a part or very probably plays a part. Mentioned inter alia are: analgesics, stimulation and regulation of food intake, effect on μ-agonists such as morphine, treatment of withdrawal symptoms, reduction of the addiction potential of opioids, anxiolysis, modulation of motor activity, memory disorders, epilepsy; modulation of neurotransmitter release, in particular of glutamate, serotonin and dopamine, and hence neurodegenerative diseases; influence on the cardiovascular system, triggering of an erection, diuresis, antinatriuresis, electrolyte balance, arterial blood pressure, water retention disorders, intestinal motility (diarrhoea), relaxation of the respiratory tract, micturation reflex (urinary incontinence). The use of agonists and antagonists as anorectics, analgesics (also when coadministered with opioids) or nootropics is also discussed.

The possible applications of compounds that bind to the ORL1 receptor and activate or inhibit it are correspondingly diverse. In addition, however, opioid receptors such as the μ-receptor, but also the other subtypes of these opioid receptors, namely δ and κ, play an important part in the field of pain therapy and also other of the aforementioned indications. It is accordingly desirable if the compound also has an effect on these opioid receptors.

The object of the present invention was to provide medicinal products which act on the nociceptin/ORL1 receptor system.

SUMMARY OF THE INVENTION

Surprisingly it has now been found that substituted indole derivatives having the general formula I act on the nociceptin/ORL1 receptor system and are suitable for the treatment of pain, anxiety conditions and other diseases.

The invention therefore provides substituted indole derivatives having the general formula I,

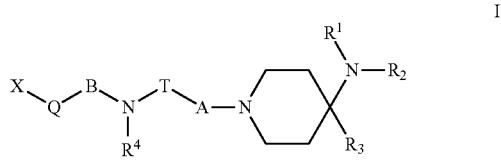

wherein
A and B mutually independently denote $CH_2$, C=O or $SO_2$
X stands for indolyl, unsubstituted or mono- or polysubstituted;
T stands for $(CR^{5a-c}R^{6a-c})_n$, n=1, 2 or 3
Q stands for $(CR^{7a-c}R^{8a-c})_m$, m=0, 1, 2 or 3
$R^1$ and $R^2$ mutually independently denote $C_{1-3}$ alkyl or H or the radicals $R^1$ and $R^2$ form a ring with inclusion of the N atom and together denote $(CH_2)_3$ or $(CH_2)_4$;
$R^3$ denotes aryl or heteroaryl, each optionally bound by a $C_{1-3}$ alkyl chain, each unsubstituted or mono- or polysubstituted; or $C_{1-6}$ alkyl, unsubstituted or mono- or polysubstituted;
$R^4$ denotes H; $C_{1-6}$ alkyl, branched or unbranched, saturated or unsaturated, unsubstituted or mono- or polysubstituted; aryl, heteroaryl or cycloaryl, each optionally bound by a $C_{1-3}$ alkyl chain;
$R^{5a-c}$ and $R^{6a-c}$ mutually independently stand for H; F, CN, OH, $OCH_3$, $OCF_3$; $C_{1-6}$ alkyl, each saturated or unsaturated, branched or unbranched, unsubstituted or mono- or polysubstituted; $C_{3-8}$ cycloalkyl, aryl or heteroaryl, each unsubstituted or mono- or polysubstituted; or for a $C_{3-8}$ cycloalkyl, aryl or heteroaryl radical bound by a $C_{1-3}$ alkyl chain, each unsubstituted or mono- or polysubstituted; or one of the radicals $R^{5a-c}$ or $R^{6a-c}$ forms a five-, six- or seven-membered ring with the radical $R^4$ with inclusion of the nitrogen atom, which ring can itself be substituted or unsubstituted or can be fused to a further five-, six- or seven-membered ring, which can be aromatic or non-aromatic;
$R^{7a-c}R^{8a-c}$ mutually independently stand for H; F, CN, OH, $OCH_3$, $OCF_3$; $C_{1-6}$ alkyl, each saturated or unsaturated, branched or unbranched, unsubstituted or mono- or polysubstituted; $C_{3-8}$ cycloalkyl, aryl or heteroaryl, each unsubstituted or mono- or polysubstituted; or for a $C_{3-8}$ cycloalkyl, aryl or heteroaryl radical bound by a $C_{1-3}$ alkyl chain, each unsubstituted or mono- or polysubstituted;

or one of the radicals $R^{7a-c}$ or $R^{8a-c}$ forms a five-, six- or seven-membered unsaturated ring with a substituent in the 2 or 3 position of the indolyl ring X, with the proviso that compounds in which $R^3$ stands for a phenyl radical which is substituted in the 3 position with OH or $OCOC_{1-8}$ alkyl are excluded from protection, in the form of the racemate; the enantiomers, diastereomers, mixtures of enantiomers or diastereomers or a single enantiomer or diastereomer; the bases and/or salts of physiologically compatible acids or cations.

The compounds according to the invention exhibit good binding to the ORL1 receptor but also to the μ-opioid receptor.

DETAILED DESCRIPTION OF THE INVENTION

Within the meaning of this invention the expressions "$C_{1-6}$ alkyl" and "$C_{1-3}$ alkyl" include acyclic saturated or unsaturated hydrocarbon radicals, which can be branched or straight-chain and unsubstituted or mono- or polysubstituted, having respectively 1, 2, 3, 4, 5 or 6 C atoms or 1, 2 or 3 C atoms, i.e. $C_{1-5}$ alkanyls, $C_{2-5}$ alkenyls and $C_{2-5}$ alkynyls or $C_{1-3}$ alkanyls, $C_{2-3}$ alkenyls and $C_{2-3}$ alkynyls. Alkenyls have at least one C=C double bond and alkynyls have at least one C≡C triple bond. Alkyl is advantageously selected from the group comprising methyl, ethyl, n-propyl, 2-propyl, n-butyl, isobutyl, sec-butyl, tert-butyl, n-pentyl, isopentyl, neopentyl, n-hexyl, 2-hexyl; ethylenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), 1,1-dimethylethyl, 1,1-dimethylpropyl, butenyl, butynyl, pentenyl, pentynyl, hexyl, hexenyl or hexynyl. Methyl and ethyl are particularly preferred within the meaning of this invention.

For the purposes of this invention the expression "cycloalkyl" or "$C_{3-8}$ cycloalkyl" denotes cyclic hydrocarbons having 3, 4, 5, 6, 7 or 8 carbon atoms, wherein the hydrocarbons can be saturated or unsaturated (but not aromatic), unsubstituted or mono- or polysubstituted. $C_{3-8}$ cycloalkyl is advantageously selected from the group including cyclopropyl, cyclobutyl, cyclopentyl, cyclohexyl, cycloheptyl, cyclooctyl, cyclopentenyl, cyclohexenyl, cycloheptenyl and cyclooctenyl. Cyclobutyl, cyclopentyl and cyclohexyl are particularly preferred within the meaning of this invention.

The term $(CH_2)_{3-6}$ is understood to mean —CH$_2$—CH$_2$—CH$_2$—, —CH$_2$—CH$_2$—CH$_2$—CH$_2$—, —CH$_2$—CH$_2$—CH$_2$—CH$_2$—CH$_2$— and CH$_2$—CH$_2$—CH$_2$—CH$_2$—CH$_2$—CH$_2$—.

Within the meaning of this invention the expression "aryl" denotes carbocyclic ring systems having up to 14 ring members with at least one aromatic ring, but without heteroatoms in only one of the rings, inter alia phenyls, naphthyls and phenanthrenyls. The aryl radicals can also be fused to other saturated, (partially) unsaturated or aromatic ring systems. Each aryl radical can be present in unsubstituted or mono- or polysubstituted form, wherein the aryl substituents can be identical or different and can be at any desired and possible position of the aryl. Phenyl or naphthyl radicals are particularly advantageous.

The expression "heteroaryl" stands for a 5-, 6- or 7-membered cyclic aromatic radical containing at least 1, optionally also 2, 3, 4 or 5 heteroatoms, wherein the heteroatoms can be identical or different and the heterocyclic compound can be unsubstituted or mono- or polysubstituted; if the heterocyclic compound is substituted, the substituents can be identical or different and can be at any desired and possible position of the heteroaryl. The heterocyclic compound can also be part of a bicyclic or polycyclic system having up to 14 ring members. Preferred heteroatoms are nitrogen, oxygen and sulfur. It is preferable for the heteroaryl radical to be selected from the group including pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the binding to the compounds having the general structure I can be made via any desired and possible ring member of the heteroaryl radical.

In connection with definitions of substituents, "alkyl" denotes "$C_{1-6}$ alkyl" unless otherwise specified.

In connection with "alkyl" and "cycloalkyl", the term "substituted" within the meaning of this invention is understood to mean the substitution of one or more hydrogen radicals with F, Cl, Br, I, —CN, NH$_2$, NH-alkyl, NH-aryl, NH-heteroaryl, NH-cycloalkyl, NH-alkyl-aryl, NH-alkyl-heteroaryl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, C(=O)C$_{1-6}$ alkyl, C(=S)C$_{1-6}$ alkyl, C(=O)aryl, C(=S)aryl, C(=O)C$_{1-6}$ alkyl-aryl, C(=S)C$_{1-6}$ alkyl-aryl, C(=O)-heteroaryl, C(=S)-heteroaryl, C(=O)-cycloalkyl, C(=S)-cycloalkyl, CO$_2$H, CO$_2$ alkyl, CO$_2$ alkyl-aryl, C(=O)NH$_2$, C(=O)NH-alkyl, C(=O)NH-aryl, C(=O)NH-cycloalkyl, C(=O)N(alkyl)$_2$, C(=O)N(alkyl-aryl)$_2$, C(=O)N(alkyl-heteroaryl)$_2$, C(=O)N(cycloalkyl)$_2$, SO-alkyl, SO$_2$-alkyl, SO$_2$NH$_2$, SO$_3$H, PO(O—C$_{1-6}$ alkyl)$_2$=O, =S, wherein polysubstituted radicals are understood to mean radicals which are either substituted multiple times, e.g. twice or three times, at different or the same atoms, for example three times at the same C atom, as in the case of CF$_3$ or —CH$_2$CF$_3$, or at different sites, as in the case of —CH(OH)—CH=CH—CHCl$_2$. The polysubstitution can take place with identical or with different substituents. A substituent can also optionally itself be substituted, so —O alkyl also includes —O—CH$_2$—CH$_2$—O—CH$_2$—CH$_2$—OH. It is preferable within the meaning of this invention for alkyl or cycloalkyl to be substituted with F, Cl, Br, I, CN, CH$_3$, C$_2$H$_5$, NH$_2$, NO$_2$, SH, CF$_3$, OH, OCH$_3$, cyclopentyl, cyclohexyl, OC$_2$H$_5$ or N(CH$_3$)$_2$, preferably F, Cl, Br, I, CN, CH$_3$, C$_2$H$_5$, NH$_2$, NO$_2$, SH, CF$_3$, OH, OCH$_3$, OC$_2$H$_5$ or N(CH$_3$)$_2$. It is most particularly preferred for alkyl or cycloalkyl to be substituted with OH, OCH$_3$ or OC$_2$H$_5$.

In connection with "aryl", "indolyl" or "heteroaryl", "mono- or polysubstituted" within the meaning of this invention is understood to mean the single or multiple, e.g. two, three, four or five times, substitution of one or more hydrogen atoms in the ring system with F, Cl, Br, I, CN, NH$_2$, NH-alkyl, NH-aryl, NH-heteroaryl, NH-alkyl-aryl, NH-alkyl-heteroaryl, NH-cycloalkyl, NH-alkyl-OH, N(alkyl)$_2$, N(alkyl-aryl)$_2$, N(alkyl-heteroaryl)$_2$, N(cycloalkyl)$_2$, N(alkyl-OH)$_2$, NO$_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, C(=O)C$_{1-6}$ alkyl, C(=S)C$_{1-6}$ alkyl, C(=O)aryl, C(=S)aryl, C(=O)—C$_{1-6}$ alkyl-aryl, C(=S)C$_{1-6}$ alkyl-aryl, C(=O)-heteroaryl, C(=S)-heteroaryl, C(=O)-cycloalkyl, C(=S)-cycloalkyl, CO$_2$H, CO$_2$-alkyl, CO$_2$-alkyl-aryl, C(=O)NH$_2$, C(=O)NH-alkyl, C(=O)NH-aryl, C(=O)NH-cycloalkyl, C(=O)N(alkyl)$_2$, C(=O)N(alkyl-aryl)$_2$, C(=O)N(alkyl-heteroaryl)₂, C(=O)N(cycloalkyl)₂, S(O)-alkyl, S(O)-aryl, SO₂-alkyl, SO₂-aryl, SO₂NH₂, SO₃H, CF₃; alkyl, cycloalkyl, aryl and/or heteroaryl; at one or optionally different atoms (wherein a substituent can optionally itself be substituted). The polysubstitution is performed with identical or with different substituents. If an aryl, indolyl or heteroaryl radical is itself substituted with an aryl or heteroaryl radical optionally bound via a bridge, this substituent is preferably itself unsubstituted or mono- or polysubstituted with F, Cl, Br, I, CN, CH₃, C₂H₅, NH₂, NO₂, SH, CF₃, OH, OCH₃, OC₂H₅ or N(CH₃)₂.

It is particularly preferred within the meaning of this invention for aryl, indolyl or heteroaryl to be substituted with F, Cl, Br, I, CN, CH₃, C₂H₅, NH₂, NO₂, SH, CF₃, OH, OCH₃, OC₂H₅ or N(CH₃)₂.

The term salt is understood to mean any form of the active ingredient according to the invention in which it assumes an ionic form or is charged and is coupled to a counterion (a cation or anion) or is in solution. Also included here are complexes of the active ingredient with other molecules and ions, in particular complexes which are complexed by means of ionic interactions. It means in particular (and this is also a preferred embodiment of this invention) physiologically compatible salts, in particular physiologically compatible salts with cations or bases and physiologically compatible salts with anions or acids or also a salt formed with a physiologically compatible acid or a physiologically compatible cation.

Within the meaning of this invention the term "physiologically compatible salt with anions or acids" is understood to mean salts of at least one of the compounds according to the invention—mostly protonated, for example on nitrogen—as cation with at least one anion, which are physiologically—particularly when used in humans and/or mammals—compatible. Within the meaning of this invention this is particularly understood to mean the salt formed with a physiologically compatible acid, namely salts of the individual active ingredient with inorganic or organic acids which are physiologically—particularly when used in humans and/or mammals—compatible. Examples of physiologically compatible salts of certain acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid and/or aspartic acid. The hydrochloride salt, the citrate and the hemicitrate are particularly preferred.

Within the meaning of this invention the term "salt formed with a physiologically compatible acid" is understood to mean salts of the individual active ingredient with inorganic or organic acids which are physiologically—particularly when used in humans and/or mammals—compatible. The hydrochloride and the citrate are particularly preferred. Examples of physiologically compatible acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharinic acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetyl salicylic acid, hippuric acid and/or aspartic acid.

Within the meaning of this invention the term "physiologically compatible salt with cations or bases" is understood to mean salts of at least one of the compounds according to the invention—mostly a (deprotonated) acid—as anion with at least one, preferably inorganic, cation, which are physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

Within the meaning of this invention the term "salt formed with a physiologically compatible cation" is understood to mean salts of at least one of the compounds as anion with at least one inorganic cation, which is physiologically—particularly when used in humans and/or mammals—compatible. Particularly preferred are the salts of the alkali and alkaline-earth metals, but also ammonium salts, but in particular (mono) or (di)sodium, (mono) or (di)potassium, magnesium or calcium salts.

Preferred within the meaning of this invention are substituted indole derivatives wherein "alkyl substituted" and "cycloalkyl substituted" stands for the substitution of a hydrogen radical with F, Cl, Br, I, —CN, NH₂, NH—C₁₋₆ alkyl, NH—C₁₋₆ alkyl-OH, C₁₋₆ alkyl, N(C₁₋₆ alkyl)₂, N(C₁₋₆ alkyl-OH)₂, NO₂, SH, S—C₁₋₆ alkyl, S-benzyl, O—C₁₋₆ alkyl, OH, O—C₁₋₆ alkyl-OH, =O, O-benzyl, C(=O)C₁₋₆ alkyl, C(=O)OC₁₋₆ alkyl, phenyl or benzyl, and "aryl substituted", "indolyl substituted" and "heteroaryl substituted" stands for the single or multiple, e.g. two, three or four times, substitution of one or more hydrogen atoms in the ring system with F, Cl, Br, I, CN, NH₂, NH—C₁₋₆ alkyl, NH—C₁₋₆ alkyl-OH, N(C₁₋₆ alkyl)₂, N(C₁₋₆ alkyl-OH)₂, NO₂, SH, S—C₁₋₆ alkyl, OH, O—C₁₋₆ alkyl, O—C₁₋₆ alkyl-OH, C(=O)-aryl; C(=O)C₁₋₆ alkyl, C(=O)NHC₁₋₆ alkyl; C(=O)—N-morpholine; C(=O)-piperidine; (C=O)-pyrrolidine; (C=O)-piperazine; NHSO₂C₁₋₆ alkyl, NHCOC₁₋₆ alkyl, CO₂H, CH₂SO₂ phenyl, CO₂—C₁₋₆ alkyl, OCF₃, CF₃,

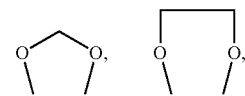

C₁₋₆ alkyl, pyrrolidinyl, piperidinyl, morpholinyl, benzyloxy, phenoxy, phenyl, pyridyl, alkylaryl, thienyl or furyl, wherein aryl and heteroaryl substituents can themselves be substituted with F, Cl, Br, I, CN, CH₃, C₂H₅, NH₂, NO₂, SH, CF₃, OH, OCH₃, OC₂H₅ or N(CH₃)₂; in the form of the racemate; the enantiomers, diastereomers, mixtures of enantiomers or diastereomers or a single enantiomer or diastereomer; the bases and/or salts of physiologically compatible acids or cations.

For a preferred embodiment of the substituted indole derivatives according to the invention, A and B mutually independently denote CH₂ or C=O.

It is particularly preferable for A to denote CH₂ and B to denote CH₂ or C=O.

Substituted indole derivatives are preferred wherein X stands for indolyl, unsubstituted or mono- or polysubstituted with F, Cl, Br, I, CN, CH₃, C₂H₅, C₃H₈, NH₂, NO₂, SH, CF₃, OH, OCH₃, OC₂H₅, N(CH₃)₂ or phenyl, unsubstituted or mono- or polysubstituted with F, Cl, Br, I, CN, CH₃, C₂H₅, NH₂, NO₂, SH, CF₃, OH, OCH₃, OC₂H₅ or N(CH₃)₂.

Substituted indole derivatives are particularly preferred wherein X stands for indole, 1-methyl-indole, 5-fluoroindole, 5-methoxyindole, 5-bromoindole, 6-chloroinidole, 6-fluoroindole, 6-methoxy-1,2-dimethylindole, 1,2-dimethylindole, 2-(4-fluorophenyl)indole, 2-phenylindole, 5-chloroindole or 6-iso-propylindole.

Also preferred are substituted indole derivatives wherein $R^1$ and $R^2$ mutually independently denote methyl or H or the radicals $R^1$ and $R^2$ form a ring with inclusion of the N atom and denote $(CH_2)_3$ or $(CH_2)_4$.

Most particularly preferred are substituted indole derivatives wherein $R^1$ and $R^2$ mutually independently denote methyl or H, preferably methyl.

Also preferred are substituted indole derivatives wherein $R^3$ stands for phenyl, benzyl or phenethyl, each unsubstituted or mono- or polysubstituted at the ring; $C_{1-6}$ alkyl, unsubstituted or mono- or polysubstituted; pyridyl, thienyl, thiazolyl, imidazolyl, 1,2,4-triazolyl or benzimidazolyl, unsubstituted or mono- or polysubstituted.

Particularly preferred are substituted indole derivatives having the general formula I, wherein $R^3$ stands for phenyl, benzyl, phenethyl, thienyl, pyridyl, thiazolyl, imidazolyl, 1,2,4-triazolyl, benzimidazolyl or benzyl, unsubstituted or mono- or polysubstituted with F, Cl, Br, CN, $CH_3$, $C_2H_5$, $NH_2$, $NO_2$, SH, $CF_3$, OH, $OCH_3$, $OC_2H_5$ or $N(CH_3)_2$; ethyl, n-propyl, 2-propyl, allyl, n-butyl, isobutyl, sec-butyl, tert-butyl, n-pentyl, isopentyl, neopentyl, n-hexyl, cyclopentyl or cyclohexyl, each unsubstituted or mono- or polysubstituted with OH, $OCH_3$ or $OC_2H_5$, wherein thienyl, pyridyl, thiazolyl, imidazolyl, 1,2,4-triazolyl and benzimidazolyl are preferably unsubstituted;
in particular
phenyl, unsubstituted or monosubstituted with F, Cl, CN, $CH_3$; thienyl; or n-butyl, unsubstituted or mono- or polysubstituted with $OCH_3$, OH or $OC_2H_5$, in particular with $OCH_3$.

Also preferred are substituted indole derivatives wherein $R^4$ denotes H, $CH_3$ or benzyl, in particular H.

Further preferred are substituted indole derivatives wherein
$R^{5a-c}$ and $R^{6a-c}$ stand for H.

Also preferred are substituted indole derivatives wherein $R^{7a-c}R^{8a-c}$ mutually independently denotes H; $C_{1-6}$ alkyl, saturated or unsaturated, branched or unbranched,
or one of the radicals $R^{7a-c}$ or $R^{8a-c}$ forms a five-, six- or seven-membered unsaturated ring with a substituent in the 3 position of the indolyl ring X, such that a structural element having the general formulae IIa-f is produced:

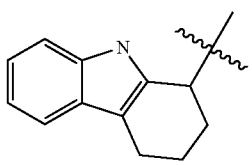

IIa

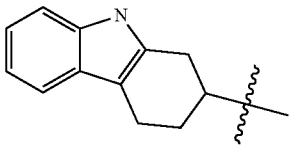

IIb

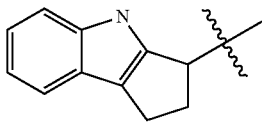

IIc

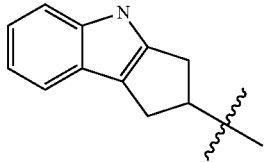

IId

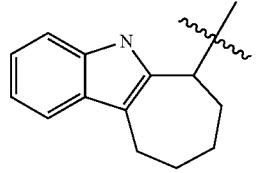

IIe

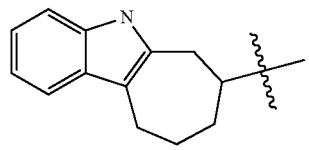

IIf

Particularly preferred are substituted indole derivatives having the general formula I, wherein $R^{7a-c}R^{8a-c}$ mutually independently stand for H; $CH_3$, ethyl or propyl;
or one of the radicals $R^{7a-c}$ or $R^{8a-c}$ forms a six-membered unsaturated ring with a substituent in the 3 position of the indolyl ring X, such that the structural element having the general formula IIa is produced:

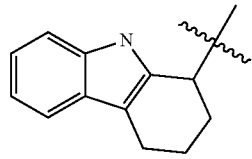

IIa

Most particularly preferred are substituted indole derivatives from the group comprising
1  N-(2-(4-(Dimethylamino)-4-phenylpiperidin-1-yl)ethyl)-N-methyl-1H-indole-6-carboxamide
2  N-(2-(4-(Dimethylamino)-4-(thiophen-2-yl)piperidin-1-yl)ethyl)-3-(1H-indol-3-yl)-4-methylpentanamide
3  N-(2-(4-(Dimethylamino)-4-phenylpiperidin-1-yl)ethyl)-5-fluoro-N-methyl-1H-indole-2-carboxamide
4  N-(2-(4-(Dimethylamino)-4-phenylpiperidin-1-yl)ethyl)-3-(1H-indol-3-yl)-N-methylpropanamide
5  N-(2-(4-(Dimethylamino)-4-(thiophen-2-yl)piperidin-1-yl)ethyl)-3-(1H-indol-3-yl)propanamide
6  N-(2-(4-(Dimethylamino)-4-(thiophen-2-yl)piperidin-1-yl)ethyl)-3-(1H-indol-3-yl)-4-methylpentanamide
7  6-Chloro-N-(2-(4-(dimethylamino)-4-(thiophen-2-yl)piperidin-1-yl)ethyl)-2,3,4,9-tetrahydro-1H-carbazole-1-carboxamide
8  N-(2-(4-(Dimethylamino)-4-(thiophen-2-yl)piperidin-1-yl)ethyl)-2-(6-fluoro-1H-indol-3-yl)acetamide
9  N-(2-(4-(Dimethylamino)-4-(thiophen-2-yl)piperidin-1-yl)ethyl)-1-methyl-1H-indole-6-carboxamide
10  N-(2-(4-(Dimethylamino)-4-(thiophen-2-yl)piperidin-1-yl)ethyl)-1-methyl-1H-indole-4-carboxamide
11  N-(3-(4-(Dimethylamino)-4-(thiophen-2-yl)piperidin-1-yl)propyl)-N-methyl-1H-indole-3-carboxamide
12  N-(2-(4-(Dimethylamino)-4-phenylpiperidin-1-yl)ethyl)-N-methyl-1H-indole-3-carboxamide 13 N-(3-(4-(Dimethylamino)-4-(thiophen-2-yl)piperidin-1-yl)propyl)-N-methyl-3-(1-methyl-1H-indol-3-yl)propanamide 14 N-(2-(4-(Dimethylamino)-4-phenylpiperidin-1-yl)ethyl)-N-methyl-3-(1-methyl-1H-indol-3-yl)propanamide 15 N-(3-(4-(Dimethylamino)-4-(thiophen-2-yl)piperidin-1-yl)propyl)-5-fluoro-N-methyl-1H-indole-2-carboxamide 16 N-(2-(4-(Dimethylamino)-4-phenylpiperidin-1-yl)ethyl)-5-fluoro-N-methyl-1H-indole-2-carboxamide 17 N-(3-(4-(Dimethylamino)-4-(thiophen-2-yl)piperidin-1-yl)propyl)-N-methyl-1H-indole-6-carboxamide 18 N-(2-(4-(Dimethylamino)-4-phenylpiperidin-1-yl)ethyl)-N-methyl-1H-indole-6-carboxamide 19 N-(3-(4-(Dimethylamino)-4-(thiophen-2-yl)piperidin-1-yl)propyl)-3-(1H-indol-3-yl)-N-methylbutanamide 20 N-(2-(4-(Dimethylamino)-4-phenylpiperidin-1-yl)ethyl)-3-(1H-indol-3-yl)-N methylbutanamide 21 N-(3-(4-(Dimethylamino)-4-(thiophen-2-yl)piperidin-1-yl)propyl)-3-(1H-indol-3-yl)-N-methylpropanamide 22 N-(3-(4-(Dimethylamino)-4-(thiophen-2-yl)piperidin-1-yl)propyl)-5-methoxy-N-methyl-1H-indole-2-carboxamide 23 N-(3-(4-(Dimethylamino)-4-(thiophen-2-yl)piperidin-1-yl)propyl)-3-(1H-indol-3-yl)-N,4-dimethylpentanamide 24 N-(2-(4-(Dimethylamino)-4-phenylpiperidin-1-yl)ethyl)-3-(1H-indol-3-yl)-N,4-dimethylpentanamide 25 6-Chloro-N-(2-(4-(dimethylamino)-4-phenylpiperidin-1-yl)ethyl)-N-methyl-2,3,4,9-tetrahydro-1H-carbazole-1-carboxamide 26 N-(3-(4-(Dimethylamino)-4-(thiophen-2-yl)piperidin-1-yl)propyl)-2-(6-fluoro-1H-indol-3-yl)-N-methylacetamide 27 N-(2-(4-(Dimethylamino)-4-phenylpiperidin-1-yl)ethyl)-2-(6-fluoro-1H-indol-3-yl)-N-methylacetamide 28 N-(3-(4-(Dimethylamino)-4-(thiophen-2-yl)piperidin-1-yl)propyl)-N,1-dimethyl-1H-indole-6-carboxamide 29 N-(2-(4-(Dimethylamino)-4-phenylpiperidin-1-yl)ethyl)-N,1-dimethyl-1H-indole-6-carboxamide 30 N-(3-(4-(Dimethylamino)-4-(thiophen-2-yl)piperidin-1-yl)propyl)-N,1-dimethyl-1H-indole-4-carboxamide 31 N-(2-(4-(Dimethylamino)-4-phenylpiperidin-1-yl)ethyl)-N,1-dimethyl-1H-indole-4-carboxamide 32 3-(1H-Indol-3-yl)-N,4-dimethyl-N-(2-(4-phenyl-4-(pyrrolidin-1-yl)piperidin-1-yl)ethyl)pentanamide 33 N-(2-(4-Butyl-4-(dimethylamino)piperidin-1-yl)ethyl)-3-(1H-indol-3-yl)-N,4-dimethylpentanamide 34 N-(3-(4-(Dimethylamino)-4-phenylpiperidin-1-yl)propyl)-3-(1H-indol-3-yl)-N,4-dimethylpentanamide 35 6-Chloro-N-(3-(4-(dimethylamino)-4-phenylpiperidin-1-yl)propyl)-N-methyl-2,3,4,9-tetrahydro-1H-carbazole-1-carboxamide 36 2-(6-Fluoro-1H-indol-3-yl)-N-methyl-N-(2-(4-phenyl-4-(pyrrolidin-1-yl)piperidin-1-yl)ethyl)acetamide 37 N,1-Dimethyl-N-(2-(4-phenyl-4-(pyrrolidin-1-yl)piperidin-1-yl)ethyl)-1H-indole-6-carboxamide 38 N-(2-(4-Butyl-4-(dimethylamino)piperidin-1-yl)ethyl)-N,1-dimethyl-1H-indole-6-carboxamide 39 N-(3-(4-(Dimethylamino)-4-phenylpiperidin-1-yl)propyl)-N,1-dimethyl-1H-indole-6-carboxamide 40 N,1-Dimethyl-N-(2-(4-phenyl-4-(pyrrolidin-1-yl)piperidin-1-yl)ethyl)-1H-indole-4-carboxamide 41 N-(2-(4-Butyl-4-(dimethylamino)piperidin-1-yl)ethyl)-N,1-dimethyl-1H-indole-4-carboxamide 42 6-Chloro-N-methyl-N-(2-(4-phenyl-4-(pyrrolidin-1-yl)piperidin-1-yl)ethyl)-2,3,4,9-tetrahydro-1H-carbazole-1-carboxamide 43 N-(2-(4-Butyl-4-(dimethylamino)piperidin-1-yl)ethyl)-6-chloro-N-methyl-2,3,4,9-tetrahydro-1H-carbazole-1-carboxamide 44 N-(2-(4-Butyl-4-(dimethylamino)piperidin-1-yl)ethyl)-2-(6-fluoro-1H-indol-3-yl)-N-methylacetamide 45 N-(3-(4-(Dimethylamino)-4-phenylpiperidin-1-yl)propyl)-2-(6-fluoro-1H-indol-3-yl)-N-methylacetamide 46 N-Methyl-N-(2-(4-phenyl-4-(pyrrolidin-1-yl)piperidin-1-yl)ethyl)-1H-indole-3-carboxamide 47 N-(2-(4-Butyl-4-(dimethylamino)piperidin-1-yl)ethyl)-N-methyl-1H-indole-3-carboxamide 48 N-Methyl-3-(1-methyl-1H-indol-3-yl)-N-(2-(4-phenyl-4-(pyrrolidin-1-yl)piperidin-1-yl)ethyl)propanamide 49 N-(2-(4-Butyl-4-(dimethylamino)piperidin-1-yl)ethyl)-N-methyl-3-(1-methyl-1H-indol-3-yl)propanamide 50 N-(3-(4-(Dimethylamino)-4-phenylpiperidin-1-yl)propyl)-N-methyl-3-(1-methyl-1H-indol-3-yl)propanamide 51 5-Fluoro-N-methyl-N-(2-(4-phenyl-4-(pyrrolidin-1-yl)piperidin-1-yl)ethyl)-1H-indole-2-carboxamide 52 N-(2-(4-Butyl-4-(dimethylamino)piperidin-1-yl)ethyl)-5-fluoro-N-methyl-1H-indole-2-carboxamide 53 N-(3-(4-(Dimethylamino)-4-phenylpiperidin-1-yl)propyl)-5-fluoro-N-methyl-1H-indole-2-carboxamide 54 N-Methyl-N-(2-(4-phenyl-4-(pyrrolidin-1-yl)piperidin-1-yl)ethyl)-1H-indole-6-carboxamide 55 N-(2-(4-Butyl-4-(dimethylamino)piperidin-1-yl)ethyl)-N-methyl-1H-indole-6-carboxamide 56 N-(3-(4-(Dimethylamino)-4-phenylpiperidin-1-yl)propyl)-N-methyl-1H-indole-6-carboxamide 57 3-(1H-Indol-3-yl)-N-methyl-N-(2-(4-phenyl-4-(pyrrolidin-1-yl)piperidin-1-yl)ethyl)butanamide 58 N-(2-(4-Butyl-4-(dimethylamino)piperidin-1-yl)ethyl)-3-(1H-indol-3-yl)-N-methylbutanamide 59 N-(3-(4-(Dimethylamino)-4-phenylpiperidin-1-yl)propyl)-3-(1H-indol-3-yl)-N-methylbutanamide 60 N-(2-(4-Butyl-4-(dimethylamino)piperidin-1-yl)ethyl)-3-(1H-indol-3-yl)-N-methylpropanamide 61 N-(3-(4-(Dimethylamino)-4-phenylpiperidin-1-yl)propyl)-3-(1H-indol-3-yl)-N-methylpropanamide 62 2-(5-Bromo-1H-indol-3-yl)-N-methyl-N-(2-(4-phenyl-4-(pyrrolidin-1-yl)piperidin-1-yl)ethyl)acetamide 63 2-(5-Bromo-1H-indol-3-yl)-N-(3-(4-(dimethylamino)-4-phenylpiperidin-1-yl)propyl)-N-methylacetamide 64 5-Methoxy-N-methyl-N-(2-(4-phenyl-4-(pyrrolidin-1-yl)piperidin-1-yl)ethyl)-1H-indole-2-carboxamide 65 N-(2-(4-Butyl-4-(dimethylamino)piperidin-1-yl)ethyl)-5-methoxy-N-methyl-1H-indole-2-carboxamide 66 N-(3-(4-(Dimethylamino)-4-phenylpiperidin-1-yl)propyl)-5-methoxy-N-methyl-1H-indole-2-carboxamide 67 1-(3-(((6-Isopropyl-1H-indol-3-yl)methyl)(methyl)amino)propyl)-N,N-dimethyl-4-(thiophen-2-yl)piperidin-4-amine 68 1-(2-(((1H-Indol-5-yl)methyl)(methyl)amino)ethyl)-N,N-dimethyl-4-phenylpiperidin-4-amine 69 1-(2-(((1H-Indol-5-yl)methylamino)ethyl)-N,N-dimethyl-4-(thiophen-2-yl)piperidin-4-amine 70 1-(2-(((2-(4-Fluorophenyl)-1H-indol-3-yl)methyl)(methyl)amino)ethyl)-N,N-dimethyl-4-phenylpiperidin-4-amine 71 N,N-Dimethyl-1-(2-(methyl((2-phenyl-1H-indol-3-yl)methyl)amino)ethyl)-4-phenylpipendin-4-amine 72 1-(2-((5-Chloro-1H-indol-3-yl)methylamino)ethyl)-N,N-dimethyl-4-(thiophen-2-yl)piperidin-4-amine 73 1-(2-(((6-Isopropyl-1H-indol-3-yl)methyl)(methyl)amino)ethyl)-N,N-dimethyl-4-phenylpiperidin-4-amine 74 1-(2-((6-Isopropyl-1H-indol-3-yl)methylamino)ethyl)-N,N-dimethyl-4-(thiophen-2-yl)pipendin-4-amine 75  1-(2-(((5-Methoxy-1H-indol-3-yl)methyl)(methyl) amino)ethyl)-N,N-dimethyl-4-phenylpiperidin-4-amine
76  1-(2-((5-Methoxy-1H-indol-3-yl)methylamino)ethyl)-N,N-dimethyl-4-(thiophen-2-yl)pipendin-4-amine
77  1-(2-(((1-Benzyl-5-methoxy-2-methyl-1H-indol-3-yl) methyl)(methyl)amino)ethyl)-N,N-dimethyl-4-phenylpiperidin-4-amine
78  1-(2-((1-Benzyl-5-methoxy-2-methyl-1H-indol-3-yl)methylamino)ethyl)-N,N-dimethyl-4-(thiophen-2-yl)piperidin-4-amine
79  1-(2-(((1,2-Dimethyl-1H-indol-3-yl)methyl)(methyl) amino)ethyl)-N,N-dimethyl-4-phenylpiperidin-4-amine
80  1-(2-((1,2-Dimethyl-1H-indol-3-yl)methylamino)ethyl)-N,N-dimethyl-4-(thiophen-2-yl)pipendin-4-amine
81  1-(3-(((1,2-Dimethyl-1H-indol-3-yl)methyl)(methyl) amino)propyl)-N,N-dimethyl-4-(thiophen-2-yl)piperidin-4-amine
82  N-(1-(4-(dimethylamino)-4-phenylpiperidin-1-yl)-3-methyl-1-oxobutan-2-yl)-2-(6-fluoro-1H-indol-3-yl)-N-methylacetamide
83  2-(5-bromo-1H-indol-3-yl)-N-(1-(4-(dimethylamino)-4-phenylpiperidin-1-yl)-3-methyl-1-oxobutan-2-yl)-N-methylacetamide
84  N-(3-(4-(dimethylamino)-4-phenylpiperidin-1-yl)-3-oxopropyl)-3-(1H-indol-3-yl)-4-methylpentanamide
85  N-(3-(4-(dimethylamino)-4-(thiophen-2-yl)piperidin-1-yl)-3-oxo-1-phenylpropyl)-3-(1H-indol-3-yl)-4-methylpentanamide
86  1-(3-(4-(dimethylamino)-4-phenylpiperidine-1-carbonyl) indolin-1-yl)-2-(6-fluoro-1H-indol-3-yl)ethanone
87  N-(2-(4-(dimethylamino)-4-phenylpiperidin-1-yl)ethyl)-3-(1H-indol-3-yl)-N,4-dimethylpentanamide
88  N-(2-(4-(dimethylamino)-4-(thiophen-2-yl)piperidin-1-yl)-2-oxoethyl)-3-(1H-indol-3-yl)-4-methylpentanamide
89  1-(3-(4-(dimethylamino)-4-phenylpiperidine-1-carbonyl) indolin-1-yl)-3-(1H-indol-3-yl)-4-methylpentan-1-one
90  N-(2-(4-(dimethylamino)-4-phenylpiperidin-1-yl)ethyl)-2-(6-fluoro-1H-indol-3-yl)-N-methylacetamide
91  N-(3-(4-(dimethylamino)-4-(thiophen-2-yl)piperidin-1-yl)-3-oxo-1-phenylpropyl)-3-(1H-indol-3-yl)butanamide
92  N-(3-(4-(dimethylamino)-4-phenylpiperidin-1-yl)-3-oxopropyl)-3-(1H-indol-3-yl)butanamide
93  N-(3-(4-(dimethylamino)-4-(thiophen-2-yl)piperidin-1-yl)-3-oxo-1-phenylpropyl)-2-(6-fluoro-1H-indol-3-yl)acetamide
94  N-(1-(4-(dimethylamino)-4-phenylpiperidin-1-yl)-3-methyl-1-oxobutan-2-yl)-3-(1H-indol-3-yl)-N-methylpropanamide
95  N-(2-(4-(dimethylamino)-4-(thiophen-2-yl)piperidin-1-yl)-2-oxo-1-phenylethyl)-2-(6-fluoro-1H-indol-3-yl)-N-methylacetamide
96  N-(3-(4-(dimethylamino)-4-(thiophen-2-yl)piperidin-1-yl)-3-oxo-1-phenylpropyl)-1H-indole-6-carboxamide
97  6-chloro-N-(3-(4-(dimethylamino)-4-(thiophen-2-yl)piperidin-1-yl)-3-oxo-1-phenylpropyl)-2,3,4,9-tetrahydro-1H-carbazole-1-carboxamide
98  N-(3-(4-(dimethylamino)-4-phenylpiperidin-1-yl)-3-oxopropyl)-3-(1H-indol-3-yl)propanamide
99  N-(3-(4-(dimethylamino)-4-phenylpiperidin-1-yl)-3-oxopropyl)-1-methyl-1H-indole-6-carboxamide
100  2-(5-bromo-1H-indol-3-yl)-N-(2-(4-(dimethylamino)-4-(thiophen-2-yl)piperidin-1-yl)-2-oxo-1-phenylethyl)-N-methylacetamide
101  N-(3-(4-(dimethylamino)-4-(thiophen-2-yl)piperidin-1-yl)-3-oxo-1-phenylpropyl)-1-methyl-1H-indole-6-carboxamide
102  N-(2-(4-(dimethylamino)-4-(thiophen-2-yl)piperidin-1-yl)-2-oxo-1-phenylethyl)-N-methyl-1H-indole-6-carboxamide
103  (6-chloro-2,3,4,9-tetrahydro-1H-carbazol-1-yl)(3-(4-(dimethylamino)-4-phenylpiperidine-1-carbonyl)piperidin-1-yl)methanone
104  (4-(dimethylamino)-4-phenylpiperidin-1-yl)(1-(5-fluoro-1H-indole-2-carbonyl)piperidin-3-yl)methanone
105  N-(2-(4-(dimethylamino)-4-(thiophen-2-yl)piperidin-1-yl)-2-oxo-1-phenylethyl)-3-(1H-indol-3-yl)-N,4-dimethylpentanamide
106  1-(3-(4-(dimethylamino)-4-phenylpiperidine-1-carbonyl)piperidin-1-yl)-3-(1H-indol-3-yl)-4-methylpentan-1-one
107  6-chloro-N-(3-(4-(dimethylamino)-4-phenylpiperidin-1-yl)-3-oxopropyl)-2,3,4,9-tetrahydro-1H-carbazole-1-carboxamide
108  N-(3-(4-(dimethylamino)-4-(thiophen-2-yl)piperidin-1-yl)-3-oxo-1-phenylpropyl)-1-methyl-1H-indole-4-carboxamide
109  N-(2-(4-(dimethylamino)-4-(thiophen-2-yl)piperidin-1-yl)-2-oxoethyl)-1-methyl-1H-indole-6-carboxamide
110  N-(2-(4-(dimethylamino)-4-(thiophen-2-yl)piperidin-1-yl)-2-oxo-1-phenylethyl)-3-(1H-indol-3-yl)-N-methylpropanamide
111  N-(2-(4-(dimethylamino)-4-(thiophen-2-yl)piperidin-1-yl)-2-oxo-1-phenylethyl)-N,1-dimethyl-1H-indole-6-carboxamide
112  N-(2-(4-butyl-4-(dimethylamino)piperidin-1-yl)ethyl)-2-(6-fluoro-1H-indol-3-yl)-N-methylacetamide
113  N-(3-(4-(dimethylamino)-4-phenylpiperidin-1-yl)-3-oxopropyl)-1H-indole-6-carboxamide
114  (4-(dimethylamino)-4-phenylpiperidin-1-yl)(1-(1-methyl-1H-indole-4-carbonyl)indolin-3-yl)methanone
115  2-(5-bromo-1H-indol-3-yl)-1-(3-(4-(dimethylamino)-4-phenylpiperidine-1-carbonyl)piperidin-1-yl)ethanone
116  6-chloro-N-(2-(4-(dimethylamino)-4-(thiophen-2-yl)piperidin-1-yl)-2-oxoethyl)-2,3,4,9-tetrahydro-1H-carbazole-1-carboxamide
117  N-(3-(4-(dimethylamino)-4-phenylpiperidin-1-yl)-3-oxopropyl)-3-(1-methyl-1H-indol-3-yl)propanamide
118  (4-(dimethylamino)-4-phenylpiperidin-1-yl)(1-(1-methyl-1H-indole-6-carbonyl)indolin-3-yl)methanone
119  N-(2-(4-(dimethylamino)-4-phenylpiperidin-1-yl) ethyl)-N,1-dimethyl-1H-indole-6-carboxamide
120  6-(dimethylamino)-N-(3-(4-(dimethylamino)-4-phenylpiperidin-1-yl)-3-oxopropyl)-1H-indole-2-carboxamide
121  N-(3-(4-(dimethylamino)-4-phenylpiperidin-1-yl)-3-oxopropyl)-1-methyl-1H-indole-4-carboxamide
122  1-(3-(4-(dimethylamino)-4-phenylpiperidine-1-carbonyl)piperidin-1-yl)-3-(1H-indol-3-yl)butan-1-one
123  1-(3-(4-(dimethylamino)-4-phenylpiperidine-1-carbonyl)piperidin-1-yl)-3-(1H-indol-3-yl)propan-1-one
124  1-(3-(4-(dimethylamino)-4-phenylpiperidine-1-carbonyl)piperidin-1-yl)-2-(6-fluoro-1H-indol-3-yl)ethanone
125  (1-(1H-indole-6-carbonyl)piperidin-3-yl)(4-(dimethylamino)-4-phenylpiperidin-1-yl)methanone
126  N-(2-(4-(dimethylamino)-4-(thiophen-2-yl)piperidin-1-yl)-2-oxo-1-phenylethyl)-N-methyl-3-(1-methyl-1H-indol-3-yl)propanamide
127  6-chloro-N-(2-(4-(dimethylamino)-4-phenylpiperidin-1-yl)ethyl)-N-methyl-2,3,4,9-tetrahydro-1H-carbazole-1-carboxamide
128  (4-(dimethylamino)-4-phenylpiperidin-1-yl)(1-(1-methyl-1H-indole-6-carbonyl)piperidin-3-yl) methanone 129  N-(3-(4-(dimethylamino)-4-phenylpiperidin-1-yl)-3-oxopropyl)-5-methoxy-1H-indole-2-carboxamide
130  (4-(dimethylamino)-4-phenylpiperidin-1-yl)(1-(1-methyl-1H-indole-4-carbonyl)piperid in-3-yl) methanone
131  (1-(1H-indole-3-carbonyl)piperidin-3-yl)(4-(dimethylamino)-4-phenylpiperidin-1-yl)methanone
132  N-(1-(4-(dimethylamino)-4-phenylpiperidin-1-yl)-3-methyl-1-oxobutan-2-yl)-N-methyl-3-(1-methyl-1H-indol-3-yl)propanamide
133  1-(3-(4-(dimethylamino)-4-phenylpiperidine-1-carbonyl)piperidin-1-yl)-3-(1-methyl-1H-indol-3-yl)propan-1-one
134  6-chloro-N-(2-(4-(dimethylamino)-4-(thiophen-2-yl)piperidin-1-yl)-2-oxo-1-phenylethyl)-N-methyl-2,3,4,9-tetrahydro-1H-carbazole-1-carboxamide
135  N-(2-(4-(dimethylamino)-4-(thiophen-2-yl)piperidin-1-yl)-2-oxoethyl)-1-methyl-1H-indole-4-carboxamide
136  (6-(dimethylamino)-1H-indol-2-yl)(3-(4-(dimethylamino)-4-phenylpiperidine-1-carbonyl)piperidin-1-yl)methanone
137  N-((1H-indol-3-yl)methyl)-N-methyl-2-(4-phenyl-4-(pyrrolidin-1-yl)piperidin-1-yl)ethanamine
138  1-(2-(((1H-indol-3-yl)methyl)(methyl)amino)ethyl)-4-butyl-N,N-dimethylpiperidin-4-amine
139  3-((1H-indol-3-yl)methylamino)-1-(4-(dimethylamino)-4-phenylpiperidin-1-yl)propan-1-one
140  N-((1H-indol-5-yl)methyl)-N-methyl-2-(4-phenyl-4-(pyrrolidin-1-yl)piperidin-1-yl)ethanamine
141  1-(2-(((1H-indol-5-yl)methyl)(methyl)amino)ethyl)-4-butyl-N,N-dimethylpiperidin-4-amine
142  3-((1H-indol-5-yl)methylamino)-1-(4-(dimethylamino)-4-phenylpiperidin-1-yl)propan-1-one
143  N-((1H-indol-6-yl)methyl)-N-methyl-2-(4-phenyl-4-(pyrrolidin-1-yl)piperidin-1-yl)ethanamine
144  1-(2-(((1H-indol-6-yl)methyl)(methy)amino)ethyl)-4-butyl-N,N-dimethylpiperidin-4-amine
145  3-((1H-indol-6-yl)methylamino)-1-(4-(dimethylamino)-4-phenylpiperidin-1-yl)propan-1-one
146  2-(((1H-indol-5-yl)methyl)(methyl)amino)-1-(4-(dimethylamino)-4-phenylpiperidin-1-yl)-3-methylbutan-1-one
147  2-(((1H-indol-5-yl)methyl)(methyl)amino)-1-(4-(dimethylamino)-4-(thiophen-2-yl)piperidin-1-yl)-2-phenylethanone
148  (1-((1H-indol-5-yl)methyl)piperidin-3-yl)(4-(dimethylamino)-4-phenylpiperidin-1-yl)methanone
149  2-(((1H-indol-6-yl)methyl)(methyl)amino)-1-(4-(dimethylamino)-4-phenylpiperidin-1-yl)-3-methylbutan-1-one
150  2-(((1H-indol-6-yl)methyl)(methyl)amino)-1-(4-(dimethylamino)-4-(thiophen-2-yl)pipendin-1-yl)-2-phenylethanone
151  (1-((1H-indol-3-yl)methyl)piperidin-3-yl)(4-(dimethylamino)-4-phenylpiperidin-1-yl)methanone
152  (1-((1H-indol-6-yl)methyl)piperidin-3-yl)(4-(dimethylamino)-4-phenylpiperidin-1-yl)methanone
153  N-((5-bromo-1H-indol-3-yl)methyl)-N-methyl-2-(4-phenyl-4-(pyrrolidin-1-yl)piperidin-1-yl)ethanamine
154  1-(2-(((5-bromo-1H-indol-3-yl)methyl)(methyl)amino)ethyl)-4-butyl-N,N-dimethylpiperidin-4-amine
155  (1-((5-bromo-1H-indol-3-yl)methyl)piperidin-3-yl)(4-(dimethylamino)-4-phenylpiperidin-1-yl) methanone
156  (4-(dimethylamino)-4-phenylpiperidin-1-yl)(1-((2-methyl-1H-indol-3-yl)methyl)piperidin-3-yl) methanone
157  1-(2-(((1H-indol-7-yl)methyl)(methy)amino)ethyl)-4-butyl-N,N-dimethylpiperidin-4-amine
158  (1-((1H-indol-7-yl)methyl)piperidin-3-yl)(4-(dimethylamino)-4-phenylpiperidin-1-yl)methanone
159  N-((1H-indol-4-yl)methyl)-N-methyl-2-(4-phenyl-4-(pyrrolidin-1-yl)piperidin-1-yl)ethanamine
160  1-(2-(((1H-indol-4-yl)methyl)(methy)amino)ethyl)-4-butyl-N,N-dimethylpiperidin-4-amine
161  (1-((1H-indol-4-yl)methyl)piperidin-3-yl)(4-(dimethylamino)-4-phenylpiperidin-1-yl)methanone
162  3-((5-bromo-1H-indol-3-yl)methylamino)-1-(4-(dimethylamino)-4-phenylpiperidin-1-yl)propan-1-one
163  3-((5-bromo-1H-indol-3-yl)methylamino)-1-(4-(dimethylamino)-4-(thiophen-2-yl)piperidin-1-yl)-3-phenylpropan-1-one
164  3-((1H-indol-3-yl)methylamino)-1-(4-(dimethylamino)-4-(thiophen-2-yl)piperidin-1-yl)-3-phenylpropan-1-one
165  3-((1H-indol-5-yl)methylamino)-1-(4-(dimethylamino)-4-(thiophen-2-yl)piperidin-1-yl)-3-phenylpropan-1-one
166  (1-((1H-indol-5-yl)methyl)indolin-3-yl)(4-(dimethylamino)-4-phenylpiperidin-1-yl)methanone
167  1-(4-(dimethylamino)-4-phenylpiperidin-1-yl)-3-((2-methyl-1H-indol-3-yl)methylamino)propan-1-one
168  1-(4-(dimethylamino)-4-(thiophen-2-yl)piperidin-1-yl)-3-((2-methyl-1H-indol-3-yl)methylamino)-3-phenylpropan-1-one
169  3-((1H-indol-6-yl)methylamino)-1-(4-(dimethylamino)-4-(thiophen-2-yl)piperidin-1-yl)-3-phenylpropan-1-one
170  (1-((1H-indol-6-yl)methyl)indolin-3-yl)(4-(dimethylamino)-4-phenylpiperidin-1-yl)methanone
171  3-((1H-indol-7-yl)methylamino)-1-(4-(dimethylamino)-4-phenylpiperidin-1-yl)propan-1-one
172  2-((1H-indol-7-yl)methylamino)-1-(4-(dimethylamino)-4-(thiophen-2-yl)piperidin-1-yl)ethanone
173  3-((1H-indol-7-yl)methylamino)-1-(4-(dimethylamino)-4-(thiophen-2-yl)piperidin-1-yl)-3-phenylpropan-1-one
174  3-((1H-indol-4-yl)methylamino)-1-(4-(dimethylamino)-4-(thiophen-2-yl)piperidin-1-yl)-3-phenylpropan-1-one
175  (1-((1H-indol-4-yl)methypindolin-3-yl)(4-(dimethylamino)-4-phenylpiperidin-1-yl)methanone
176  (4-(dimethylamino)-4-phenylpiperidin-1-yl)(1-((6-methoxy-1,2-dimethyl-1H-indol-3-yl)methyl)piperidin-3-yl)methanone
177  (4-(dimethylamino)-4-phenylpiperidin-1-yl)(1-((2-(4-fluorophenyl)-1H-indol-3-yl)methyl)piperidin-3-yl) methanone
178  1-(2-((5-chloro-1H-indol-3-yl)methylamino)ethyl)-N,N-dimethyl-4-(thiophen-2-yl)piperidin-4-amine
179  1-(2-((1H-indol-3-yl)methylamino)ethyl)-N,N-dimethyl-4-(thiophen-2-yl)piperidin-4-amine
180  1-(2-(((6-isopropyl-1H-indol-3-yl)methyl)(methyl)amino)ethyl)-N,N-dimethyl-4-phenylpiperidin-4-amine
181  1-(2-(((1H-indol-6-yl)methyl)(methyl)amino)ethyl)-N,N-dimethyl-4-phenylpiperidin-4-amine
182  1-(2-(((5-chloro-1H-indol-3-yl)methyl)(methy)amino)ethyl)-N,N-dimethyl-4-phenylpiperidin-4-amine
183  1-(2-(((5-chloro-1H-indol-3-yl)methyl)(methy)amino)ethyl)-N,N-dimethyl-4-phenylpiperidin-4-amine
184  1-(2-(((1H-indol-6-yl)methyl)(methy)amino)ethyl)-N,N-dimethyl-4-phenylpiperidin-4-amine
185  1-(2-(((5-bromo-1H-indol-3-yl)methyl)(methyl)amino)ethyl)-N,N-dimethyl-4-phenylpiperidin-4-amine
186  1-(2-(((1H-indol-3-yl)methyl)(methy)amino)ethyl)-N,N-dimethyl-4-phenylpiperidin-4-amine 187 1-(2-(((1H-indol-3-yl)methyl)(methy)amino)ethyl)-N,N-dimethyl-4-phenylpiperidin-4-amine
188 1-(2-((5-methoxy-1H-indol-3-yl)methylamino)ethyl)-N,N-dimethyl-4-(thiophen-2-yl)piperidin-4-amine
189 1-(2-(((1,2-dimethyl-1H-indol-3-yl)methyl)(methyl)amino)ethyl)-N,N-dimethyl-4-phenylpiperidin-4-amine
190 1-(2-(((5-methoxy-1H-indol-3-yl)methyl)(methyl)amino)ethyl)-N,N-dimethyl-4-phenylpiperidin-4-amine
191 1-(2-(((5-methoxy-1H-indol-3-yl)methyl)(methyl)amino)ethyl)-N,N-dimethyl-4-phenylpiperidin-4-amine
192 1-(2-(((5-methoxy-1H-indol-3-yl)methyl)(methyl)amino)ethyl)-N,N-dimethyl-4-phenylpiperidin-4-amine
193 1-(2-(((1-benzyl-5-methoxy-2-methyl-1H-indol-3-yl)methyl)(methyl)amino)ethyl)-N,N-dimethyl-4-phenylpiperidin-4-amine
194 1-(2-(((1H-indol-4-yl)methyl)(methy)amino)ethyl)-N,N-dimethyl-4-phenylpiperidin-4-amine
195 1-(2-(((1H-indol-4-yl)methyl)(methy)amino)ethyl)-N,N-dimethyl-4-phenylpiperidin-4-amine in the form of the racemate; the enantiomers, diastereomers, mixtures of enantiomers or diastereomers or a single enantiomer or diastereomer; the bases and/or salts of physiologically compatible acids or cations.

The substances according to the invention act for example on the ORL1 receptor of relevance in connection with various diseases, such that they are suitable as a pharmaceutical active ingredient in a medicinal product. The invention therefore also provides medicinal products containing at least one substituted indole derivative according to the invention, optionally along with suitable additives and/or auxiliary substances and/or optionally further active ingredients.

The medicinal products according to the invention optionally contain, in addition to at least one substituted indole derivative according to the invention, suitable additives and/or auxiliary substances, including carrier materials, fillers, solvents, diluents, dyes and/or binders, and can be administered as liquid dosage forms in the form of injection solutions, drops or juices, as semi-solid dosage forms in the form of granules, tablets, pellets, patches, capsules, plasters/spray plasters or aerosols. The choice of auxiliary substances, etc., and the amount thereof to use depend on whether the medicinal product is to be administered by oral, peroral, parenteral, intravenous, intraperitoneal, intradermal, intramuscular, intranasal, buccal, rectal or local means, for example on the skin, mucous membranes or in the eyes. Preparations in the form of tablets, pastilles, capsules, granules, drops, juices and syrups are suitable for oral administration; solutions, suspensions, easily reconstitutable dry preparations and sprays are suitable for parenteral, topical and inhalative administration. Substituted indole derivatives according to the invention in a depot formulation, in dissolved form or in a plaster, optionally with addition of agents promoting skin penetration, are suitable preparations for percutaneous administration. Preparation forms suitable for oral or percutaneous administration can deliver the substituted indole derivatives according to the invention on a delayed release basis. The substituted indole derivatives according to the invention can also be used in parenteral long-term depot forms, such as implants or implanted pumps, for example. Other additional active ingredients known to the person skilled in the art can be added in principle to the medicinal products according to the invention.

The amount of active ingredient to be administered to the patient varies according to the weight of the patient, the type of administration, the indication and the severity of the illness. 0.00005 to 50 mg/kg, preferably 0.001 to 0.5 mg/kg, of at least one substituted indole derivative according to the invention are conventionally administered.

A preferred form of the medicinal product contains a substituted indole derivative according to the invention as a pure diastereomer and/or enantiomer, as a racemate or as a non-equimolar or equimolar mixture of diastereomers and/or enantiomers.

As was mentioned in the introduction in respect of the prior art, the ORL1 receptor has been identified in particular in the pain mechanism. Substituted indole derivatives according to the invention can accordingly be used for the preparation of a medicinal product for the treatment of pain, in particular acute, neuropathic or chronic pain.

The invention therefore also provides the use of a substituted indole derivative according to the invention to prepare a medicinal product for the treatment of pain, in particular acute, visceral, neuropathic or chronic pain.

The invention also provides the use of a substituted indole derivative according to the invention to prepare a medicinal product for the treatment of anxiety conditions, stress and stress-related syndromes, depression, epilepsy, Alzheimer's disease, senile dementia, general cognitive dysfunctions, learning and memory disorders (as a nootropic), withdrawal symptoms, alcohol and/or drug and/or prescription drug abuse and/or dependency, sexual dysfunctions, cardiovascular diseases, hypotension, hypertension, tinnitus, pruritus, migraine, hearing impairment, gastrointestinal motility disorders, food intake disorders, anorexia, obesity, locomotive disorders, diarrhoea, cachexia, urinary incontinence, or as a muscle relaxant, anticonvulsant or anaesthetic, or for coadministration in treatment with an opioid analgesic or with an anaesthetic, for diuresis or antinatriuresis, anxiolysis, for the modulation of motor activity, for the modulation of neurotransmitter release and treatment of associated neurodegenerative diseases, for the treatment of withdrawal symptoms and/or for the reduction of the addiction potential of opioids.

In one of the above uses it can be preferable for a substituted indole derivative that is used to be in the form of a pure diastereomer and/or enantiomer, a racemate or a non-equimolar or equimolar mixture of diastereomers and/or enantiomers.

The invention also provides a process for the treatment, in particular in one of the aforementioned indications, of a non-human mammal or human requiring treatment of pain, in particular chronic pain, by administration of a therapeutically active dose of a substituted indole derivative according to the invention or of a medicinal product according to the invention.

The present invention also provides a process for preparing the substituted indole compounds according to the invention. The chemicals and reaction components used in the reactions described are available commercially or can be produced by methods known to the person skilled in the art.

General Process for Preparing Compounds Having the General Formula I the meaning given above, at temperatures of preferably 0° C. to 80° C., to form compounds having the general formula III.

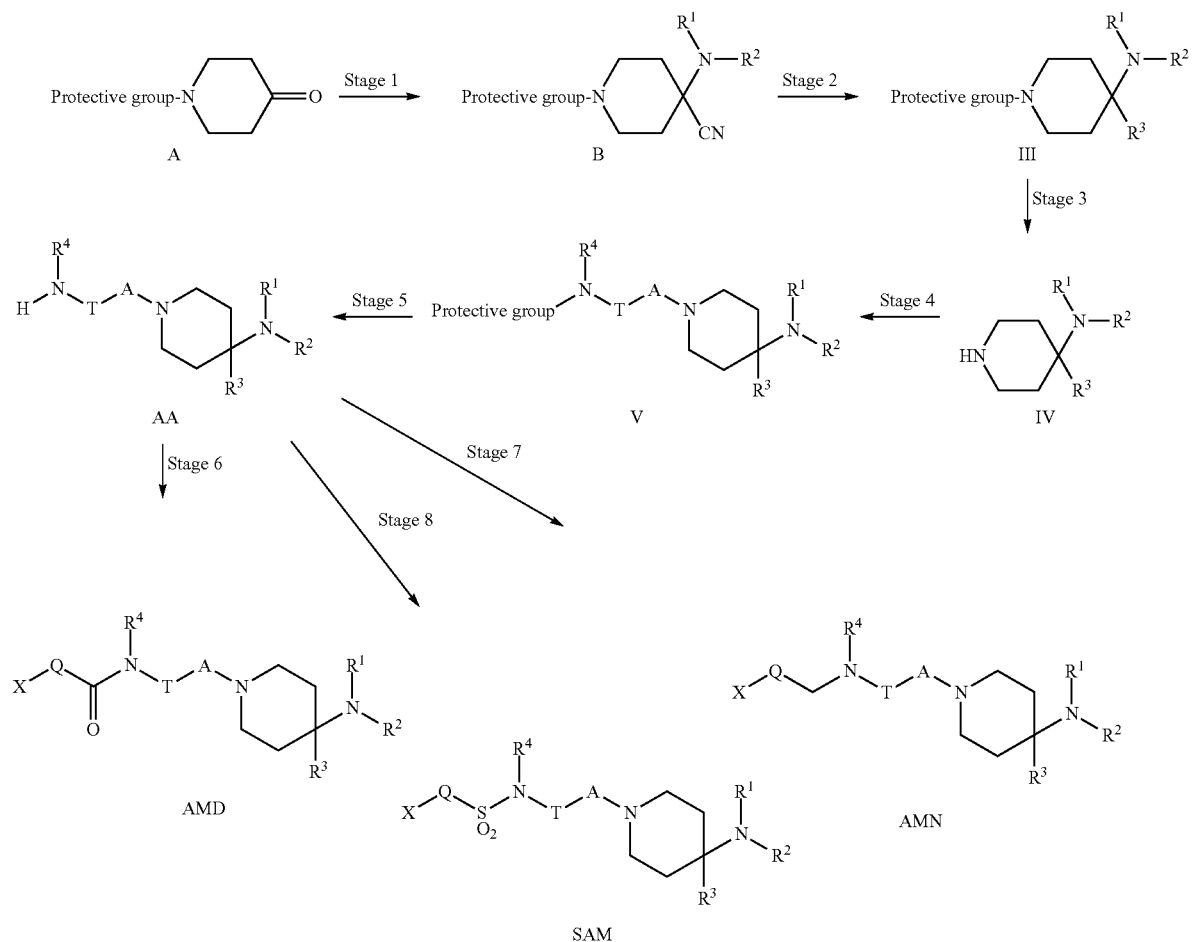

Reaction Scheme 1: Synthesis Routes

The compounds having the general formula AA, as shown in Reaction Scheme 1, can be converted to compounds having the formula AMD, SAM and AMN.

The protective group in formula A, B and III is a suitable nitrogen protective group, preferably benzyl or tert-butyloxycarbonyl.

In stage 1, compounds known from the literature having the general formula A in at least one solvent, preferably selected from the group consisting of methanol, ethanol, dioxane, diethyl ether, tetrahydrofuran, water and dimethyl formamide, are reacted with an amine having the general formula $HNR^1R^2$, wherein $R^1$ and $R^2$ have the meaning given above, and potassium cyanide or sodium cyanide, with addition of at least one acid, preferably selected from the group consisting of sodium hydrogen sulfite, acetic acid, trifluoroacetic acid, hydrochloric acid and sulfuric acid, at temperatures of preferably 0° C. to 60° C., to form compounds having the general formula B.

In stage 2, compounds having the general formula B in at least one solvent, preferably selected from the group consisting of tetrahydrofuran, diethyl ether and dioxane, are reacted with a Grignard reagent $R^3MgBr$ or $R^3MgCl$, wherein $R^3$ has In stage 3, compounds having the general formula III are converted to compounds having the general formula IV by elimination of the protective group.

If the protective group is benzyl, the conversion to compounds having the general formula IV takes place in 2 steps. First of all the compounds having the general formula III (protective group=benzyl) in at least one solvent, preferably selected from the group consisting of chloroform, diethyl ether, tetrahydrofuran, acetonitrile, acetone and dimethyl formamide, are reacted with carbobenzoxychloride (CbzCl) at temperatures of preferably 0° C. to 80° C. to form compounds having the general formula III (protective group=Cbz). Then the compounds having the general formula III (protective group=Cbz) in at least one solvent, preferably selected from the group consisting of methanol, ethanol, diethyl ether, tetrahydrofuran, acetonitrile, dimethyl formamide and dimethyl sulfoxide, are reacted with an inorganic base, preferably selected from the group consisting of lithium hydroxide, sodium hydroxide and potassium hydroxide, at temperatures of preferably 0° C. to 80° C., to form compounds having the general formula IV.

Alternatively, compounds having the general formula III (protective group=benzyl) in at least one solvent, preferably selected from the group consisting of methanol, ethanol, ethyl acetate, chloroform, diethyl ether, tetrahydrofuran, acetone and dimethyl formamide in the presence of a catalyst, preferably selected from the group consisting of palladium on carbon, palladium hydroxide, palladium acetate and palladium black, are reacted with a suitable hydrogen source, preferably selected from the group consisting of hydrogen, formic acid, 1,3-cyclohexadiene and ammonium formate, at temperatures of preferably 0° C. to 80° C., to form compounds having the general formula IV.

If the protective group is tert-butyloxycarbonyl (Boc), then the compounds having the general formula III in at least one solvent, preferably selected from the group consisting of methanol, ethanol, dichloromethane, diethyl ether, tetrahydrofuran, acetonitrile, dioxane, dimethyl formamide and dimethyl sulfoxide, are reacted with an acid, preferably selected from the group consisting of trifluoroacetic acid, sulfuric acid and hydrochloric acid, at temperatures of preferably 0° C. to 80° C., to form compounds having the general formula IV.

In stage 4, the compounds having the general formula IV in at least one solvent, preferably selected from the group consisting of dioxane, diethyl ether, tetrahydrofuran, acetonitrile and dimethyl formamide, are reacted with a suitable alkyl halide in the presence of an excess of a base, preferably selected from the group consisting of caesium carbonate, calcium carbonate, potassium carbonate, triethylamine, diisopropyl ethylamine and pyridine, at temperatures of preferably 0° C. to 80° C., to form compounds having the general formula V.

Alternatively, compounds having the general formula IV are reacted with a suitable aldehyde in at least one organic solvent, preferably selected from the group consisting of diethyl ether, tetrahydrofuran, methanol, ethanol, dichloroethane, dichloromethane and toluene, with addition of at least one reducing agent, preferably selected from the group consisting of borane-pyridine complex, sodium boron hydride, sodium triacetoxyboron hydride, sodium cyanoboron hydride and triethylsilane, optionally in the presence of at least one acid, preferably selected from the group consisting of formic acid, acetic acid, hydrochloric acid and trifluoroacetic acid, at temperatures of preferably −70° C. to 100° C., to form compounds having the general formula V.

Alternatively, compounds having the general formula IV in at least one solvent, preferably selected from the group consisting of dichloromethane, acetonitrile, dimethyl formamide, diethyl ether, dioxane and tetrahydrofuran, are reacted with acids having the general formula protective group-$NR_4$-T-$CO_2$H, wherein protective group, $R_4$ and T have the meanings given above, with addition of at least one coupling reagent, preferably selected from the group consisting of carbonyl diimidazole (CDI), 2-chloro-1-methylpyridinium iodide (Mukaiyama reagent), N-(3-dimethylaminopropyl)-N'-ethylcarbodiimide (EDCl), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or an organic base, preferably selected from the group consisting of triethylamine, diisopropylethylamine and pyridine, and optionally with addition of 4-(dimethylamino)pyridine or 1-hydroxybenzotriazole, to form compounds having the general formula V.

In stage 5, if the protective group is not H, the protective group is eliminated. If the protective group is tert-butyloxycarbonyl, then the compounds having the general formula V in at least one solvent, preferably selected from the group consisting of diethyl ether, tetrahydrofuran, methanol, ethanol, dichloromethane, dioxane and dimethyl formamide, are reacted with an acid, preferably selected from the group consisting of trifluoroacetic acid, hydrochloric acid and sulfuric acid, at temperatures of preferably 0° C. to 80° C., to form compounds having the general formula AA.

In stage 6, compounds having the general formula AA in at least one solvent, preferably selected from the group consisting of dichloromethane, acetonitrile, dimethyl formamide, diethyl ether, dioxane and tetrahydrofuran, are reacted with acids having the general formula X-Q-$CO_2$H, wherein X and Q have the meanings given above, with addition of at least one coupling reagent, preferably selected from the group consisting of carbonyl diimidazole (CDI), 2-chloro-1-methylpyridinium iodide (Mukaiyama reagent), N-(3-dimethylaminopropyl)-N'-ethylcarbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or an organic base, preferably selected from the group consisting of triethylamine, diisopropylethylamine and pyridine, and optionally with addition of 4-(dimethylamino)pyridine or 1-hydroxybenzotriazole, to form compounds having the general formula AMD.

In stage 7, compounds having the general formula AA are reacted with aldehydes having the general formula X-Q-CHO, wherein X and Q have the meanings given above, in at least one organic solvent, preferably selected from the group consisting of diethyl ether, tetrahydrofuran, methanol, ethanol, dichloroethane, dichloromethane and toluene, with addition of at least one reducing agent, preferably selected from the group consisting of borane-pyridine complex, sodium boron hydride, sodium triacetoxyboron hydride, sodium cyanoboron hydride and triethylsilane, optionally in the presence of at least one acid, preferably selected from the group consisting of formic acid, acetic acid, hydrochloric acid and trifluoroacetic acid, at temperatures of preferably −70° C. to 100° C., to form compounds having the general formula AMN.

In stage 8, compounds having the general formula AA are reacted with sulfonyl chlorides having the general formula X-Q-$SO_2$Cl, wherein X and Q have the meanings given above, in at least one organic solvent, preferably selected from the group consisting of dichloromethane, acetonitrile, dimethyl formamide, diethyl ether, dioxane, tetrahydrofuran, methanol, ethanol and toluene, in the presence of an excess of a base, preferably selected from the group consisting of caesium carbonate, calcium carbonate, potassium carbonate, triethylamine, diisopropylethylamine and pyridine, at temperatures of preferably −70° C. to 100° C., to form compounds having the general formula SAM.

EXAMPLES

Amine Building Blocks AA
Common Intermediates and General Procedures

Synthesis of
N,N-Dimethyl-4-(thiophen-2-yl)piperidin-4-amine
trifluoroacetate

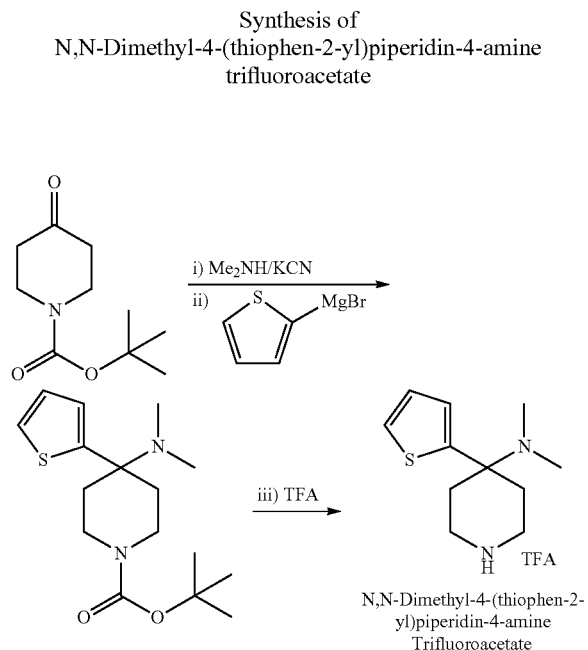

Step-1: Dimethylamine (10 eq.) was added to a solution of 1,4-Cyclohexanedione monoethylene acetal (12.8 mmol) in methanol (5 ml) and acetic acid (3 ml) at 0° C. Then potassium cyanide (2.5 eq.) was added to the reaction mixture through solid addition funnel and stirred for another 16 h. The reaction mixture was slowly quenched with $NH_4OH$ solution (50 g ice+50 ml liquor ammonia) and stirred at 0° C. for another half an hour. The reaction mixture was extracted with ethylacetate. Organic layer was washed with water, satd. $FeSO_4$, brine successively and dried over anh. Sodium sulfate and concentrated under reduced pressure to give the pure desired product. Yield: 94%

Step-2: A solution of step-1 product (2 mmol) in THF (5 ml) was added to an ice-cold solution of thiophene-2-magnesium bromide (5 eq, freshly prepared from 2-bromothiophene, Mg and catalytic amount of $I_2$ in 30 ml THF) and the reaction mixture was allowed to stir at RT for 16 h under nitrogen atmosphere. The reaction mixture was quenched with satd. Ammonia solution under ice-cold condition and extracted with ethylacetate. Organic layer was washed with water, brine successively and dried over anh. Sodium sulfate and concentrated under reduced pressure to give the crude product. The crude product was purified by silica gel column chromatography (EtOH/Hexane) to give the desired step-2 product. Yield: 30%

Step-3: To a solution of step-2 product (1.64 mmol) in DCM (5 ml) was added TFA (1 ml) at 0° C. and stirred for 2 h at RT. Then the reaction mixture was concentrated and the crude mass was azeotroped twice with dry toluene to give the TFA salt of the amine that was used as such for the coupling reactions.

Synthesis of
N,N-Dimethyl-4-phenylpiperidin-4-amine
trifluoroacetate

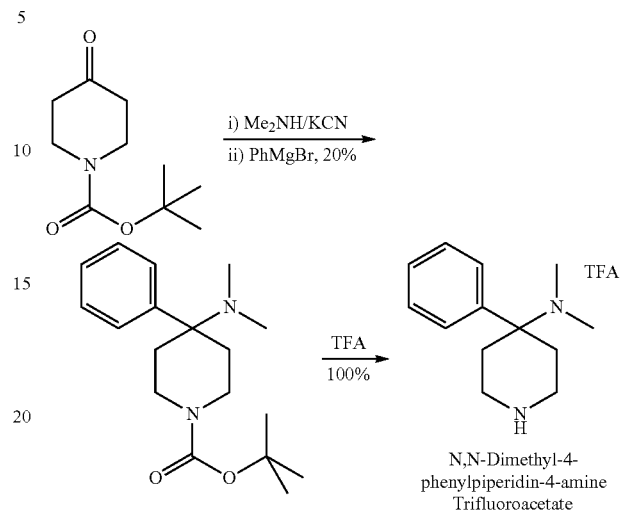

Step-1: Dimethylamine (10 eq.) was added to a solution of 1,4-Cyclohexanedione monoethylene acetal (12.8 mmol) in methanol (5 ml) and acetic acid (3 ml) at 0° C. Then potassium cyanide (2.5 eq.) was added to the reaction mixture through solid addition funnel and stirred for another 16 h. The reaction mixture was slowly quenched with NH4OH solution (50 g ice+50 ml liquor ammonia) and stirred at 0° C. for another half an hour. The reaction mixture was extracted with ethylacetate. Organic layer was washed with water, satd. FeSO4, brine successively and dried over anh. Sodium sulfate and concentrated under reduced pressure to give the pure desired product. Yield: 94%

Step-2: A solution of step-1 product (2 mmol) in THF (5 ml) was added to an ice-cold solution of phenyl magnesium bromide (5 eq. 1M solution in THF) and the reaction mixture was allowed to stir at RT for 16 h under nitrogen atmosphere. The reaction mixture was quenched with satd. Ammonia solution under ice-cold condition and extracted with ethylacetate. Organic layer was washed with water, brine successively and dried over anh. Sodium sulfate and concentrated under reduced pressure to give the crude product. The crude product was purified by silica gel column chromatography (EtOH/Hexane) to give the desired step-2 product. Yield: 20%

Step-3: To a solution of step-2 product (1.64 mmol) in DCM (5 ml) was added TFA (1 ml) at 0° C. and stirred for 2 h at RT. Then the reaction mixture was concentrated and the crude mass was azeotroped twice with dry toluene to give the TFA salt of the amine that was used as such for the coupling reactions.

Synthesis of
1-(tert-Butoxycarbonyl)indoline-3-carboxylic acid

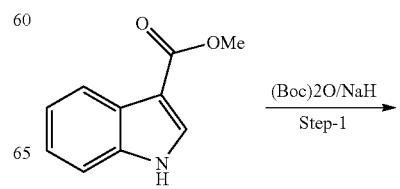

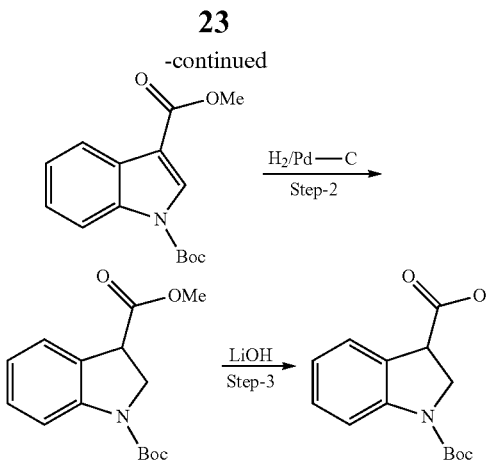

Step-1: Methyl-3 indole carboxylate (17.1 mmol) was placed in a 50 ml round bottom flask with NaH (1.5 eq.) and cooled to an ice-bath. THF (20 ml) was added with stirring. After 30 minutes Boc-anhydride (1.5 eq.) was added and stirred for overnight. The reaction mixture was quenched with satd. Ammonium chloride solution, diluted with ether and washed with water. The organic layer was dried with anh. sodium sulfate and concentrated. The crude mass was purified by column chromatography (EN hexane) to give the desired product. Yield: 98%

Step-2: The Step-1 product was hydrogenated (8 mmol) in parr-shaker with 5% Pd/C (1 g) using 60 psi hydrogen pressure in a mixture of ethyl acetate (30 ml) and methanol (10 ml) for 3 days. The reaction mixture was filtered and filtrate was concentrated. The crude mass was purified by column chromatography (EN hexane) to give the desired product. Yield: 98%

Step-3: To a suspension of Step-2 product (11.75 mmol) in methanol (40 ml), tetrahydrofuran (40 ml) and water (30 ml) was added $LiOH.H_2O$ (5 eq) and the reaction mixture was allowed to stir at 25° C. for overnight. Methanol and THF were completely evaporated; aqueous layer was acidified with 1(N)HCl and filtered. The white solid was taken in a mixture of 350 ml acetone and 50 ml methanol and stirred for 1 h. After filtration the white solid was dried under vacuum to give desired acid intermediate. Yield: 84%

General Procedure No. 1—Amidation Reaction:

To a dichloromethane solution (3 ml/mmol) of N-boc-amino acid (1 eq.) was added EDCI (1.5 eq.), HOBT (1 eq.), DIPEA (2.5 eq.) and the resulting reaction mixture was allowed to stir for 15 minutes at 25° C. In another round bottom flask, TFA salt of N,N-dimethyl-4-(thiophen-2-yl) piperidin-4-amine trifluoroacetate (1.5 eq) in dichloromethane (1 ml/mmol) was cooled in ice bath, treated with DIPEA (4 eq.) and it was added to the reaction mixture. The reaction mixture was allowed to stir at 25° C. for 16 hrs and diluted with dichloromethane. Organic layer was successively washed with aqueous ammonium chloride, sodium bicarbonate and brine and finally dried over sodium sulfate. Evaporation of organic layer under reduced pressure gave the crude product, which was purified by column chromatography on neutral alumina using MeOH/DCM as eluent.

General Procedure No. 2—Boc-Deprotection:

At 0° C., 5-10 equiv of acetylchloride were added to a solution of the boc protected amine in methanol. Progress of the reaction was followed via TLC. The solvent was removed under reduced pressure, after complete conversion. The desired product was obtained as hydrochloride and utilized in the subsequent reactions without further purification.

1) Amine Structural Units AA:

Structural unit AA-1: N,N-Dimethyl-1-(2-(methylamino)ethyl)-4-phenylpiperidin-4-amine tris hydrochloride Stage 1: 1-Benzyl-N,N-dimethyl-4-phenylpiperidin-4-amine A little iodine was added to a mixture of 34.5 g (3.5 eq) magnesium and 100 ml dry diethyl ether, followed over a period of 10 min by 10 g (0.15 eq) bromobenzene, and the mixture was stirred for a further 10 min. Once the reaction had started, 183 g (2.85 eq) bromo-benzene dissolved in 500 ml diethyl ether were added dropwise over a period of 2 h and the mixture was stirred for a further 15 min. 100 g (1 eq) 1-benzyl-4-(dimethylamino)piperidine-4-carbonitrile dissolved in 900 ml diethyl ether were added over a period of 2 h to the Grignard reagent prepared in the preceding step and the mixture was then heated for 12 h at 80° C. The reaction course was monitored by thin-layer chromatography (10% MeOH/ $CHCl_3$). Once the conversion was complete, the reaction solution was cooled to 0° C., mixed with saturated $NH_4Cl$ solution, extracted with ethyl acetate (3×300 ml) and the combined organic phases were dried with $Na_2SO_4$. Following removal of the solvent under reduced pressure, the residue was purified by column chromatography (silica gel; 1% MeOH/$CHCl_3$). 30 g (35%) of product were obtained in the form of a yellow solid.

Stage 2: Benzyloxycarbonyl-4-(dimethylamino)-4-phenylpiperidine 500 ml (10 eq) Cbz chloride were added dropwise to 50 g (1 eq) 1-benzyl-N,N-dimethyl-4-phenylpiperidin-4-amine over a period of 1 h and the reaction mixture obtained was stirred for 2 h at room temperature. The reaction course was monitored by thin-layer chromatography (10% MeOH/ $CHCl_3$). Once the conversion was complete, the reaction mixture was cooled to 0° C., made alkaline with saturated sodium hydrogen carbonate solution and extracted 3 times with 300 ml EtOAc. The combined organic phases were dried with $Na_2SO_4$. Following removal of the solvent under reduced pressure, the residue was purified by column chromatography (silica gel; 50% EtOAc/heptane). 12 g (21%) of product were obtained in the form of an oil.

Stage 3: tert-Butyloxycarbonyl-4-(dimethylamino)-4-phenylpiperidine 12.2 g KOH were added to a solution of 12 g (1 eq) benzyloxycarbonyl-4-(dimethylamino)-4-phenylpiperidine in 120 ml ethanol and the reaction mixture was refluxed for 48 h. The reaction course was monitored by thin-layer chromatography (20% MeOH/$CHCl_3$). Once the conversion was complete, the solvent was distilled off completely, the residue suspended in ethyl acetate, filtered, and the organic phase dried over sodium sulfate. Following removal of the solvent under reduced pressure, the crude product was dissolved in dioxane, mixed with saturated sodium hydrogen carbonate solution and 11.9 g (1.5 eq) of Boc anhydride and stirred for 30 min at room temperature. Once the conversion was complete, the reaction mixture was extracted with 3×200 ml ethyl acetate and the combined organic phases were dried over $Na_2SO_4$. Following removal of the solvent under reduced pressure, 8.5 g (77%) of crude product were obtained in the form of a colourless solid.

Stage 4: N,N-Dimethyl-4-phenylpiperidin-4-amine bishydrochloride 10 equivalents of acetyl chloride were added to a solution of tert-butyloxycarbonyl-4-(dimethylamino)-4-phenylpiperidine in methanol at 0° C. The reaction course was monitored by thin-layer chromatography (10% MeOH/$CHCl_3$).

Once the conversion was complete, the solvent was removed under reduced pressure and the product obtained in the form of a solid.

Stage 5: tert-Butyl 2-(4-(dimethylamino)-4-phenylpiperidin-1-yl)ethyl(methyl)carbamate 7 g (1 eq) N,N-dimethyl-4-phenylpiperidin-4-amine were added in portions to a solution of 6.5 g (1.5 eq) tert-butyl methyl(2-oxoethyl)carbamate in 60 ml methanol. This reaction mixture was cooled to 0° C., 3.97 g (2.5 eq) sodium cyanoboron hydride were added in portions and then the mixture was stirred for 10 min at room temperature. The reaction mixture obtained was adjusted to a pH of ~5 with acetic acid and stirred for 12 h at room temperature. The reaction course was monitored by thin-layer chromatography (20% MeOH/CHCl$_3$). As the conversion was still not complete, 1.5 g sodium cyanoboron hydride and acetic acid were added and the reaction mixture was stirred for a further 30 to 45 min. Once the conversion was complete, the methanol was distilled off, 100 ml saturated NaHCO$_3$ solution were added and the mixture obtained was extracted with chloroform (2×200 ml) and the combined organic phases were dried over Na$_2$SO$_4$. Following removal of the solvent under reduced pressure, the residue was purified by column chromatography (silica gel; 5% MeOH/CHCl$_3$). 8 g (64%) of product were obtained in the form of an oil.

Stage 6: N,N-Dimethyl-1-(2-(methylamino)ethyl)-4-phenylpiperidin-4-amine tris hydrochloride HCl gas was passed through a solution of 9 g (1 eq) tert-butyl 2-(4-(dimethylamino)-4-phenylpiperidin-1-yl)ethyl(methyl)carbamate in 600 ml CH$_3$Cl for 30 min. The reaction course was monitored by thin-layer chromatography (20% MeOH/CHCl$_3$). Once the conversion was complete, the passage of HCl gas was continued for a further 30 min and the completeness of the conversion again monitored by thin-layer chromatography (20% MeOH/CHCl$_3$). Once the conversion was complete, the solvent was removed under reduced pressure and 7.2 g (96%) of the desired product obtained in the form of a white solid.

Structural unit AA-2: N-methyl-2-(4-phenyl-4-(pyrrolidin-1-yl)piperidin-1-yl)ethanamine tris hydrochloride Stage 1: 1-Benzyl-4-(pyrrolidin-1-yl)piperidine-4-carbonitrile 100 g (5 eq) pyrrolidine were added to a solution of 50 g (1 eq) 1-benzylpiperidin-4-one in 250 ml ethanol and the mixture was stirred for 10 min at room temperature. 25 ml (0.5 eq) hydrochloric acid were then added dropwise to the reaction mixture over a period of 10 min and the mixture was stirred for 30 min at room temperature. 55 g (3 eq) potassium cyanide dissolved in 250 ml water were added to this reaction mixture and it was stirred for three days at room temperature. The reaction course was monitored by thin-layer chromatography (50% EtOAc/heptane). Once the conversion was complete, the solid that had formed was filtered off and washed with iced water (3×150 ml). The solid obtained was then suspended in ethyl acetate and dried with Na$_2$SO$_4$. Following removal of the solvent under reduced pressure, 70 g of crude product were obtained in the form of a solid.

Stage 2: 1-Benzyl-4-phenyl-4-(pyrrolidin-1-yl)piperidine

A little iodine was added to a mixture of 31.2 g (5 eq) magnesium and 100 ml dry THF, followed over a period of 10 min by 10 g (0.25 eq) bromobenzene, and the mixture was stirred for a further 10 min. Once the reaction had started, 194.2 g (4.75 eq) bromobenzene dissolved in 500 ml THF were added dropwise over a period of 2 h and the mixture was stirred for a further 15 min. 70 g (1 eq) 1-benzyl-4-(pyrrolidin-1-yl)piperidine-4-carbonitrile dissolved in 450 ml THF were added over a period of 2 h to the Grignard reagent prepared in the preceding step and the mixture was then heated for 12 h at 80° C. The reaction course was monitored by thin-layer chromatography (10% MeOH/CHCl$_3$). Once the conversion was complete, the reaction solution was cooled to 0° C., mixed with saturated NH$_4$Cl solution, extracted with ethyl acetate (3×200 ml) and the combined organic phases were dried with Na$_2$SO$_4$. Following removal of the solvent under reduced pressure, 33 g (40%) of crude product were obtained in the form of an oil.

Stage 3: Benzyloxycarbonyl-4-phenyl-4-(pyrrolidin-1-yl)piperidine 60 g (3.5 eq) Cbz chloride were added dropwise to a solution of 33 g (1 eq) 1-benzyl-4-phenyl-4-(pyrrolidin-1-yl)piperidine in 330 ml chloroform over a period of 10 min and the reaction mixture obtained was stirred for 30 min at room temperature. The reaction course was monitored by thin-layer chromatography (ethyl acetate). Once the conversion was complete, the solvent was distilled off completely and the residue adjusted to a pH of ~6 with 10% HCl solution and washed 3 times with 100 ml EtOAc. In an ice bath the aqueous solution was adjusted to a pH of ~9 with NaOH solution and then extracted 3 times with 100 ml chloroform. The combined organic phases were dried with Na$_2$SO$_4$. Following removal of the solvent under reduced pressure, the residue was purified by column chromatography (silica gel; 20% EtOAc/heptane). 11 g (29%) of product were obtained in the form of a yellow solid.

Stage 4: 4-Phenyl-4-(pyrrolidin-1-yl)piperidine 11 g KOH were added to a solution of 7.3 g (1 eq) benzyloxycarbonyl-4-phenyl-4-(pyrrolidin-1-yl)piperidine in 100 ml ethanol and the reaction mixture was refluxed for 24 h. The reaction course was monitored by thin-layer chromatography (20% MeOH/CHCl$_3$). Once the conversion was complete, the solvent was distilled off completely and the residue mixed with 100 ml water and extracted 3 times with 100 ml CHCl$_3$. The combined organic phases were dried with Na$_2$SO$_4$. Following removal of the solvent under reduced pressure, 7 g of crude product were obtained in the form of an oil.

Stage 5: 4-Phenyl-4-(pyrrolidin-1-yl)piperidine bishydrochloride

HCl gas was passed through a solution of 9 g (1 eq) 4-phenyl-4-(pyrrolidin-1-yl)piperidine in 180 ml chloroform for ~30 min until the reaction mixture reached a pH of ~2. The reaction course was monitored by thin-layer chromatography (10% MeOH/CHCl$_3$). Once the conversion was complete, the solvent was removed under reduced pressure and the residue washed with ethyl acetate (3×100 ml) and dried. 9 g (76%) of product were obtained in the form of a solid.

Stage 6: tert-Butyl methyl(2-(4-phenyl-4-(pyrrolidin-1-yl)piperidin-1-yl)ethyl)carbamate 7 g (1 eq) 4-phenyl-4-(pyrrolidin-1-yl)piperidine bishydrochloride were added to a solution of 4.4 g (1.1 eq) tert-butyl-methyl(2-oxoethyl)carbamate in 70 ml methanol under a nitrogen atmosphere and the reaction mixture was stirred for 10 min at 0° C. 3.62 g (2.5 eq) sodium cyanoboron hydride were then added and the mixture was stirred for 30 min at room temperature. The reaction mixture obtained was adjusted to a pH of 5-6 with acetic acid and stirred for 14 h at room temperature. The reaction course was monitored by thin-layer chromatography (10% MeOH/CHCl$_3$). Once the conversion was complete, the methanol was distilled off, saturated NaHCO$_3$ solution was added and the mixture obtained was extracted with chloroform (3×50 ml) and the combined organic phases were dried over Na$_2$SO$_4$. Following removal of the solvent under reduced pressure, the residue was purified by column chromatography (silica gel; 50% EtOAc/heptane). 8 g (89%) of product were obtained in the form of a red oil.

Stage 7: tert-Butyl methyl(2-(4-phenyl-4-(pyrrolidin-1-yl)piperidin-1-yl)ethyl)carbamate tris hydrochloride HCl gas was passed through a solution of 8 g (1 eq) tert-butyl methyl(2-(4-phenyl-4-(pyrrolidin-1-yl)piperidin-1-yl)ethyl)carbamate in 160 ml chloroform at 0° C. for ~30 min until the reaction mixture reached a pH of ~2. The reaction mixture was then stirred at room temperature for 4 hours. The reaction course was monitored by thin-layer chromatography (10% MeOH/CHCl$_3$). Once the conversion was complete, the solvent was removed under reduced pressure and 8 g (97%) of product were obtained in the form of a white solid.

Structural unit AA-3: 1-(2-Aminoethyl)-N,N-dimethyl-4-(thiophen-2-yl)piperidin-4-amine tris hydrochloride Stage 1: tert-Butyloxycarbonyl-4-cyano-4-(dimethylamino)piperidine 500 ml (10 eq) dimethylamine solution and 109.9 g (5 eq) dimethylamine hydrochloride were added to a solution of 50 g (1 eq) tert-butyloxycarbonyl-4-oxopiperidine in 100 ml methanol and the mixture was cooled to 5° C. 5 ml (0.1 eq) hydrochloric acid were then added dropwise to the reaction mixture over a period of 10 min and the mixture was stirred for 60 min at room temperature. 48.9 g (3 eq) potassium cyanide were added in portions to this reaction mixture and the mixture was stirred for 24 h at room temperature. The reaction course was monitored by thin-layer chromatography (50% EtOAc/hexane). Once the conversion was complete, 150 ml water were added to the reaction mixture and it was extracted 3 times with 100 ml ethyl acetate. The combined organic phases were dried with Na$_2$SO$_4$. Following removal of the solvent under reduced pressure, crude product was obtained which was recrystallised out of hexane. 57 g (90%) of product were obtained in the form of a colourless solid.

Stage 2: tert-Butyloxycarbonyl-4-(dimethylamino)-4-(thiophen-2-yl)piperidine

A little iodine was added to a mixture of 5.6 g (3 eq) magnesium and 20 ml dry diethyl ether, followed over a period of 10 min by 5 g 2-bromothiophene, and the mixture was stirred for a further 10 min. Once the reaction had started, 33.5 g (2.6 eq) 2-bromothiophene dissolved in 80 ml diethyl ether were added dropwise and the mixture was stirred for a period of 2 h at room temperature. The Grignard reagent prepared in the preceding step was added dropwise to a solution of 20 g (1 eq) tert-butyloxycarbonyl-4-cyano-4-(dimethylamino)-piperidine dissolved in 200 ml THF and stirred overnight at room temperature. The reaction course was monitored by thin-layer chromatography (50% EtOAc/hexane). Once the conversion was complete, the reaction solution was cooled to 0° C., mixed with saturated NH$_4$Cl solution, extracted with ethyl acetate (3×100 ml) and the combined organic phases were dried with Na$_2$SO$_4$. Following removal of the solvent under reduced pressure, the residue was purified by column chromatography (Alox neutral; 30% EtOAc/hexane). 6.1 g (25%) of product were obtained in the form of a white solid.

Stage 3: N,N-Dimethyl-4-(thiophen-2-yl)piperidin-4-amine

HCl gas was passed through a solution of 10 g (1 eq) tert-butyloxycarbonyl-4-(dimethyl-amino)-4-(thiophen-2-yl)piperidine in chloroform at 0° C. for ~1 h. The reaction course was monitored by thin-layer chromatography (75% EtOAc/hexane). Once the conversion was complete, 200 ml water were added to the reaction mixture, it was adjusted to a pH of ~8 with Na$_2$CO$_3$ and then extracted with 15% IPA/CHCl$_3$. The combined organic phases were dried over Na$_2$SO$_4$. Following removal of the solvent under reduced pressure, 6 g (89%) of product were obtained in the form of a white solid.

Stage 4: tert-Butyl 2-(4-(dimethylamino)-4-(thiophen-2-yl)piperidin-1-yl)ethylcarbamate 11.1 g (1.5 eq) tert-butyl-2-bromoethylcarbamate dissolved in 65 ml THF and 9.19 g (2 eq) potassium carbonate were added to a solution of 7 g (1 eq) N,N-dimethyl-4-(thiophen-2-yl)piperidin-4-amine in 40 ml THF. The reaction mixture was heated for 6 h at 70° C. The reaction course was monitored by thin-layer chromatography (20% MeOH/CHCl$_3$). Once the conversion was complete, the solvent was distilled off completely, the residue mixed with 200 ml water and the aqueous phase extracted with 20% IPA/CHCl$_3$. The combined organic phases were dried over Na$_2$SO$_4$. Following removal of the solvent under reduced pressure, the residue was purified by column chromatography (silica gel; 10% MeOH/CHCl$_3$). 9 g (76%) of product were obtained in the form of an oil.

Stage 5: 1-(2-Aminoethyl)-N,N-dimethyl-4-(thiophen-2-yl)piperidin-4-amine tris hydrochloride HCl gas was passed through a solution of 9 g (1 eq) tert-butyl 2-(4-(dimethylamino)-4-(thiophen-2-yl)piperidin-1-yl)ethylcarbamate in chloroform at 0° C. for ~30 min. The reaction mixture was then stirred at room temperature for one hour. The reaction course was monitored by thin-layer chromatography (10% MeOH/CHCl$_3$). Once the conversion was complete, the solvent was removed under reduced pressure and 9 g (97%) of product were obtained in the form of a white solid.

Structural unit AA-4: 4-Butyl-N,N-dimethyl-1-(2-(methylamino)ethyl)piperidin-4-amine tris hydrochloride Stage 1: 1-Benzyl-4-(dimethylamino)piperidine-4-carbonitrile 208 g (3 eq) N,N-dimethylamine hydrochloride, 154 g (3 eq) potassium cyanide in 154 ml water and 1050 ml (7 eq) of a 40% dimethylamine solution were added to a solution of 150 g (1 eq) 1-benzylpiperidin-4-one in 300 ml methanol and the mixture was cooled to 0° C. 75 ml (0.5 eq) concentrated hydrochloric acid were then added at 0° C. and the reaction mixture was stirred for 24 h at room temperature. The reaction course was monitored by thin-layer chromatography (20% EtOAc/hexane). Once the conversion was complete, the solid that had formed was filtered off and washed with iced water (4 l). The solid obtained was then dissolved in ethyl acetate and dried with Na$_2$SO$_4$. Following removal of the solvent under reduced pressure, 165 g (85%) of crude product were obtained in the form of a solid.

Stage 2: 1-Benzyl-4-butyl-N,N-dimethylpiperidin-4-amine

A little iodine was added to a mixture of 17.7 g (6 eq) magnesium and 50 ml dry ether, followed over a period of 1 h by 100 g (6 eq) bromobutane dissolved in 100 ml dry ether. This reaction mixture was stirred for 1 h at room temperature. The Grignard reagent produced in the preceding step was added over a period of 20 min to a solution of 30 g (1 eq) 1-benzyl-4-(dimethylamino)piperidine-4-carbonitrile dissolved in 210 ml dry THF and the reaction mixture obtained was then stirred for 12 h at room temperature. The reaction course was monitored by thin-layer chromatography (10% MeOH/CHCl$_3$). Once the conversion was complete, the reaction solution was cooled to 0° C., mixed with saturated NH$_4$Cl solution, filtered over celite, extracted with ethyl acetate (3×200 ml) and the combined organic phases were dried over Na$_2$SO$_4$. Following removal of the solvent under reduced pressure, the residue was purified by column chromatography (aluminium oxide neutral; hexane). 18.2 g (53%) of product were obtained in the form of an oil.

Stage 3: 4-Butyl-N,N-dimethylpiperidin-4-amine bis hydrochloride 1.5 g 20% Pd(OH)$_2$/C and 6.95 g (3 eq) ammonium formate were added to a solution of 10 g (1 eq) 1-benzyl-4-butyl-N,N-dimethylpiperidin-4-amine in 100 ml MeOH. The reaction mixture obtained was refluxed for 30 min. The reaction course was monitored by thin-layer chromatography (20% MeOH/CHCl$_3$). Once the conversion was complete, the reaction solution was cooled to room temperature, filtered over celite and rewashed with methanol. The methanol is distilled off, the residue taken up in ethyl acetate/hexane, the solvent decanted off and toluene added. The organic phase thus obtained was concentrated under reduced pressure and the residue taken up in 150 ml dichloromethane. HCl gas was passed through the dichloromethane solution for 20 min, the solvent was distilled off and 7 g (74%) of product were obtained in this way as a white solid.

Stage 4: tert-Butyl 2-(4-butyl-4-(dimethylamino)piperidin-1-yl)ethyl(methyl)carbamate A solution of 4.73 g (1 eq) tert-butyl methyl(2-oxoethyl) carbamate in 20 ml methanol was added to a solution of 7 g (1 eq) 4-butyl-N,N-dimethylpiperidin-4-amine bis hydrochloride in 50 ml methanol at room temperature and the reaction mixture obtained was stirred for 50 min at room temperature. 3.43 g (2 eq) sodium cyanoboron hydride were added in portions to this reaction mixture and it was then stirred for 12 h at room temperature. The reaction course was monitored by thin-layer chromatography (20% MeOH/CHCl$_3$). Once the conversion was complete, the reaction mixture was cooled to 0° C. and adjusted to a pH of ~5 with acetic acid. 2 g tert-butyl formylmethyl methylcarbamate and 1.7 g sodium cyanoboron hydride were again added and the reaction mixture was stirred for a further 60 min at room temperature. The methanol was then distilled off, 100 ml saturated NaHCO$_3$ solution were added and the mixture obtained was extracted with ethyl acetate (2×200 ml) and the combined organic phases were dried over Na$_2$SO$_4$. Following removal of the solvent under reduced pressure, 10.5 g of crude product were obtained in the form of a pale yellow oil.

Stage 5: 4-Butyl-N,N-dimethyl-1-(2-(methylamino)ethyl)piperidin-4-amine tris hydrochloride HCl gas was passed through a solution of 10.5 g (1 eq) tert-butyl 2-(4-butyl-4-(dimethyl-amino)piperidin-1-yl)ethyl (methyl)carbamate in 1000 ml chloroform at 0° C. for ~1 h. The reaction mixture was then stirred for 12 hours at room temperature. The reaction course was monitored by thin-layer chromatography (20% MeOH/CHCl$_3$). Once the conversion was complete, the solvent was removed under reduced pressure and the residue washed with hexane (3×50 ml) and ethyl acetate (3×50 ml) and dried. 9 g (87%) of product were obtained in the form of a white solid.

Structural unit AA-5: N,N-Dimethyl-1-(3-(methylamino)propyl)-4-phenylpiperidin-4-amine tris hydrochloride Stage 1: tert-Butyl 3-(4-(dimethylamino)-4-phenylpiperidin-1-yl)propyl(methyl)-carbamate 11.1 g (1.3 eq) tert-butyl methyl(3-oxopropyl)carbamate were added to a solution of 11 g (1 eq) N,N-dimethyl-4-phenylpiperidin-4-amine dihydrochloride in 110 ml methanol at 0° C. and the reaction mixture was stirred for 15 min at 0° C. 6.2 g (3 eq) sodium cyanoboron hydride were then added in portions and the mixture was stirred for 30 min at room temperature. The reaction mixture obtained was adjusted to a pH of 5-6 with acetic acid and stirred for 12 h at room temperature. The reaction course was monitored by thin-layer chromatography (20% MeOH/CHCl$_3$). As the conversion was still not complete, 2.4 g sodium cyanoboron hydride were added and the reaction mixture obtained was adjusted to pH 5-6 with acetic acid and stirred for 60 min at room temperature.

Once the conversion was complete, the methanol was distilled off, the mixture was made alkaline with saturated NaHCO$_3$ solution, the mixture obtained was extracted with chloroform (3×100 ml) and the combined organic phases were dried over Na$_2$SO$_4$. Following removal of the solvent under reduced pressure, the residue was purified by column chromatography (silica gel; 5% MeOH/CHCl$_3$). 9 g (60%) of product were obtained.

Stage 2: N,N-Dimethyl-1-(3-(methylamino)propyl)-4-phenylpiperidin-4-amine hydrochloride HCl gas was passed through a solution of 9 g (1 eq) tert-butyl 3-(4-(dimethylamino)-4-phenylpiperidin-1-yl)propyl (methyl)carbamate in 100 ml chloroform at 0° C. for 1 h. The reaction course was monitored by thin-layer chromatography (20% MeOH/CHCl$_3$). Once the conversion was complete, the solvent was removed under reduced pressure and after trituration with diethyl ether 10 g (100%) of product were obtained in the form of a white solid.

Structural unit AA-6: N,N-Dimethyl-1-(3-(methylamino)propyl)-4-(thiophen-2-yl)piperidin-4-amine tris hydrochloride Stage 1: tert-Butyl 3-hydroxypropyl(methyl)carbamate 84.2 g (1.2 eq) sodium carbonate followed by 100 ml water were added in portions to a solution of 50 g (1 eq) 3-aminopropan-1-ol in 500 ml THF at 0° C. 156.5 ml (1.02 eq) di-tert-butyl dicarbonate were added dropwise over a period of 30 min to the solution at 0° C. On completion of the addition, the mixture was stirred for 30 min at room temperature. The reaction course was monitored by thin-layer chromatography (10% MeOH/CHCl$_3$). Once the conversion was complete, the reaction mixture was filtered over celite and the filtrate concentrated under reduced pressure. The residue was mixed with 300 ml water and extracted with 2×250 ml ethyl acetate. The combined organic phases were dried over Na$_2$SO$_4$. Following removal of the solvent under reduced pressure, 116 g (100%) of product were obtained in the form of an oil.

Stage 2: tert-Butyl-3-(tert-butyldimethylsilyloxy)propylcarbamate 11.6 g (1.3 eq) imidazole were added to a solution of 23 g (1 eq) tert-butyl 3-hydroxypropyl-carbamate in 230 ml dichloromethane. The reaction solution was stirred for 10 min at room temperature and then cooled to 0° C. 21.79 g (1.1 eq) TBDMSCl were added to this solution at 0° C. and on completion of the addition the mixture was stirred for 1 h at room temperature. The reaction course was monitored by thin-layer chromatography (30% EtOAc/hexane). Once the conversion was complete, the reaction mixture was filtered over celite and the filtrate mixed with 200 ml water and extracted with dichloromethane. The combined organic phases were dried over Na$_2$SO$_4$. Following removal of the solvent under reduced pressure, 32 g (84%) of product were obtained in the form of an oil.

Stage 3: tert-Butyl 3-(tert-butyldimethylsilyloxy)propyl(methyl)carbamate 50 g (1 eq) tert-butyl 3-(tert-butyldimethylsilyloxy)propylcarbamate dissolved in 200 ml THF were added dropwise to a mixture of 20.7 g (5 eq) sodium hydride and 300 ml THF at 0° C. After heating the reaction mixture to 10° C., 32.3 ml (3 eq) methyl iodide were added dropwise. On completion of the addition, the mixture was stirred for 3 h at room temperature. The reaction course was monitored by thin-layer chromatography (30% EtOAc/hexane). Once the conversion was complete, the reaction mixture was quenched with saturated $NH_4Cl$ solution and then extracted with ethyl acetate. The combined organic phases were dried over $Na_2SO_4$. Following removal of the solvent under reduced pressure, 48 g (92%) of product were obtained in the form of an oil.

Stage 4: tert-Butyl 3-hydroxypropyl(methyl)carbamate 482.5 ml (5 eq) acetic acid dissolved in 386 ml water were added dropwise over a period of 45 min to a solution of 95.6 g (1 eq) tert-butyl 3-(tert-butyldimethylsilyloxy)propyl(methyl)-carbamate dissolved in 386 ml THF at 0° C. and the reaction mixture was then stirred for 20 h at room temperature. As the starting product had not yet been completely converted, the mixture was cooled to 0° C., 50 ml dilute acetic acid were added over a period of 20 min and the mixture was stirred for a further 1 h at 0° C. The reaction course was monitored by thin-layer chromatography (10% EtOAc/hexane). Once the conversion was almost complete, the reaction mixture was concentrated under reduced pressure, adjusted to a pH of ~9 with $Na_2CO_3$ solution and extracted with 10% $IPA/CH_3Cl$. The combined organic phases were dried over $Na_2SO_4$. Following removal of the solvent under reduced pressure, the residue was purified by column chromatography (silica gel; 10% EtOAc/hexane). 40 g (66%) of product were obtained in the form of a colourless oil.

Stage 5: tert-Butyl methyl(3-oxopropyl)carbamate

A catalytic amount of TEMPO was added to a mixture of 20 g (1 eq) tert-butyl 3-hydroxy-propyl(methyl)carbamate in 200 ml dichloromethane and 17.7 g (2 eq) sodium hydrogen carbonate in 100 ml water at 0° C. 140 ml (7 eq) NaOCl were then added dropwise over a period of 30 min to the solution at a temperature of 0° C. and the reaction mixture obtained was stirred for a further 15 min at 0° C. The reaction course was monitored by thin-layer chromatography (40% EtOAc/hexane).

Once the conversion was complete, the reaction mixture was mixed with 150 ml water and the phases were separated. The organic phase was dried over $Na_2SO_4$. Following removal of the solvent under reduced pressure, 16 g (85%) of product were obtained in the form of a yellowish oil.

Stage 6: N,N-Dimethyl-4-(thiophen-2-yl)piperidin-4-amine bis hydrochloride

HCl gas was passed through a solution of 6 g (1 eq) tert-butyloxycarbonyl-4-(dimethylamino)-4-(thiophen-2-yl)piperidine in 120 ml chloroform at 0° C. for 1 h. The reaction course was monitored by thin-layer chromatography (75% EtOAc/hexane). Once the conversion was complete, the solvent was removed under reduced pressure and 5.3 g (98%) of product were obtained in the form of a white solid.

Stage 7: tert-Butyl 3-(4-(dimethylamino)-4-(thiophen-2-yl)piperidin-1-yl)propyl(methyl)carbamate 6.4 g (1.3 eq) tert-butyl methyl(3-oxopropyl)carbamate were added to a solution of 7.5 g (1 eq) N,N-dimethyl-4-(thiophen-2-yl)piperidin-4-amine bis hydrochloride in 75 ml methanol at 0° C. and the reaction mixture was stirred for 15 min at 0° C. 4.9 g (3 eq) sodium cyanoboron hydride were then added in portions and the mixture was stirred for 90 min at room temperature. The reaction course was monitored by thin-layer chromatography (20% $MeOH/CHCl_3$). As the conversion was not yet complete, the pH of the reaction mixture was adjusted to 5-6 with acetic acid and the mixture was stirred for 12 h at room temperature. Once the conversion was complete, the methanol was distilled off, water was added, the mixture obtained was extracted with IPA/chloroform (2×100 ml) and the combined organic phases were dried over $Na_2SO_4$. Following removal of the solvent under reduced pressure, the residue was purified by column chromatography (silica gel; 5% $MeOH/CHCl_3$). 8.5 g (84%) of product were obtained.

Stage 8: N,N-Dimethyl-1-(3-(methylamino)propyl)-4-(thiophen-2-yl)piperidin-4-amine tris hydrochloride HCl gas was passed through a solution of 1.5 g (1 eq) tert-butyl 3-(4-(dimethylamino)-4-(thiophen-2-yl)piperidin-1-yl)propyl(methyl)carbamate in 30 ml chloroform at 0° C. for ~30 min. The reaction course was monitored by thin-layer chromatography (20% $MeOH/CHCl_3$). Once the conversion was complete, the solvent was removed under reduced pressure. After trituration with diethyl ether, 1.5 g (98%) of product were obtained in the form of a white solid.

Amine Building Block AA-7: 3-Amino-1-(4-(dimethylamino)-4-phenylpiperidin-1-yl)propan-1-one dihydrochloride (i) 3-(tert-Butoxycarbonylamino)propanoic acid was converted with N,N-dimethyl-4-phenylpiperidin-4-amine trifluoroacetate according to general procedure no. 1 to yield the desired product (49%).
(ii) The product obtained above was reacted according to general procedure no. 2, to yield the desired product (6.07 g, 102%).

Amine Building Block AA-8: 2-Amino-1-(4-(dimethylamino)-4-(thiophen-2-yl)piperidin-1-yl)ethanone (i) 2-(tert-Butoxycarbonylamino)acetic acid was converted with N,N-dimethyl-4-(thiophen-2-yl)piperidin-4-amine trifluoroacetate according to general procedure no. 1 to yield the desired product (53%).
(ii) The product obtained above was reacted according to general procedure no. 2, to yield the desired product (4.82 g, 85%).

Amine Building Block AA-9: 3-Amino-1-(4-(dimethylamino)-4-(thiophen-2-yl)piperidin-1-yl)-3-phenylpropan-1-one trihydrochloride (i) 3-(tert-Butoxycarbonylamino)-3-phenylpropanoic acid was converted with N,N-dimethyl-4-(thiophen-2-yl)piperidin-4-amine trifluoroacetate according to general procedure no. 1 to yield the desired product (40%).
(ii) The product obtained above was reacted according to general procedure no. 2, to yield the desired product (5.84 g, 91%).

Amine Building Block AA-10: 1-(4-(Dimethylamino)-4-phenylpiperidin-1-yl)-3-methyl-2-(methylamino)butan-1-one trihydrochloride (i) 2-(tert-Butoxycarbonyl(methyl)amino)-3-methylbutanoic acid was converted with N,N-dimethyl-4-phenylpiperidin-4-amine trifluoroacetate according to general procedure no. 1 to yield the desired product (51%).
(ii) The product obtained above was reacted according to general procedure no. 2, to yield the desired product (8.92 g, 102%).

Amine Building Block AA-11: 1-(4-(Dimethylamino)-4-(thiophen-2-yl)piperidin-1-yl)-2-(methylamino)-2-phenylethanone trihydrochloride (i) 2-(tert-Butoxycarbonyl(methyl)amino)-2-phenylacetic acid was converted with N,N-dimethyl-4-(thiophen-2-yl)piperidin-4-amine trifluoroacetate according to general procedure no. 1 to yield the desired product (40%).
(ii) The product obtained above was reacted according to general procedure no. 2, to yield the desired product (6.92 g, 104%).

Amine Building Block AA-12: 4-(Dimethylamino)-4-phenylpiperidin-1-yl)(piperidin-3-yl)methanone trihydrochloride (i) 1-(tert-Butoxycarbonyl)piperidine-3-carboxylic acid was converted with N,N-dimethyl-4-phenylpiperidin-4-amine trifluoroacetate according to general procedure no. 1 to yield the desired product (65%).
(ii) The product obtained above was reacted according to general procedure no. 2, to yield the desired product (7.17 g, 97%).

Amine Building Block AA-13: (4-(Dimethylamino)-4-phenylpiperidin-1-yl)(indolin-3-yl)methanone trihydrochloride (i) 1-(tert-Butoxycarbonyl)indoline-3-carboxylic acid was converted with N,N-dimethyl-4-phenylpiperidin-4-amine trifluoroacetate according to general procedure no. 1 to yield the desired product (51%).
(ii) The product obtained above was reacted according to general procedure no. 2, to yield the desired product (4.82 g, 90%).

| Structure | Amine Building Block No. | Amine Building Block Name |
|---|---|---|
| 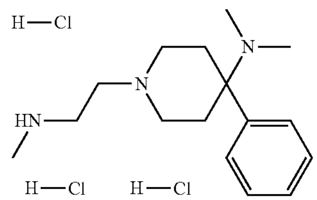 | AA-1 | N,N-Dimethyl-1-(2-(methylamino)ethyl)-4-phenylpiperidin-4-amine trihydrochloride |
| 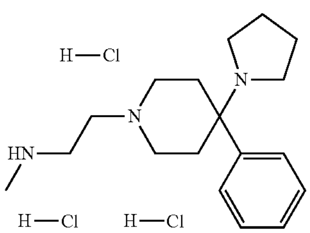 | AA-2 | N-Methyl-2-(4-phenyl-4-(pyrrolidin-1-yl)piperidin-1-yl)ethanamine trihydrochloride |
| 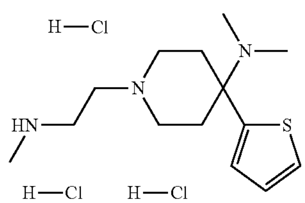 | AA-3 | 1-(2-Aminoethyl)-N,N-dimethyl-4-(thiophen-2-yl)piperidin-4-amine trihydrochloride |
| 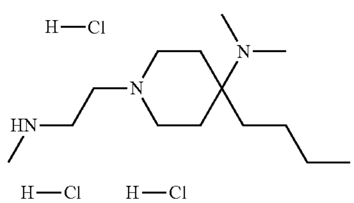 | AA-4 | 4-Butyl-N,N-dimethyl-1-(2-(methylamino)ethyl)piperidin-4-amine trihydrochloride |
| 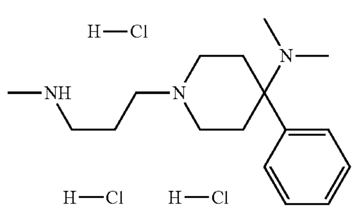 | AA-5 | N,N-Dimethyl-1-(3-(methylamino)propyl)-4-phenylpiperidin-4-amine trihydrochloride |
| 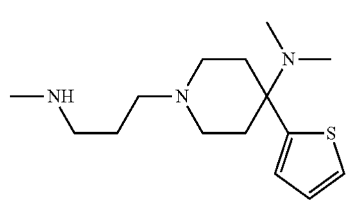 [SMILES: CNCCCN1CCC(c2cccs2)(N(C)C)CC1] | AA-6 | N,N-Dimethyl-1-(3-(methylamino)propyl)-4-(thiophen-2-yl)piperidin-4-amine |

-continued

| Structure | Amine Building Block No. | Amine Building Block Name |
|---|---|---|
| 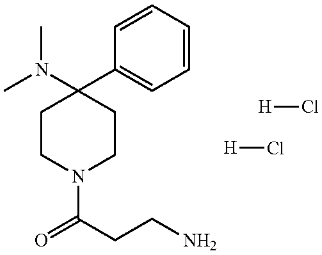 | AA-7 | 3-Amino-1-(4-(dimethylamino)-4-phenylpiperidin-1-yl)propan-1-one dihydrochloride |
| 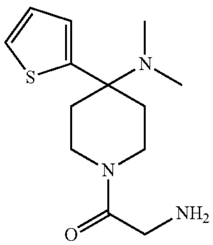 [SMILES: CN(C)C1(c2cccs2)CCN(C(=O)CN)CC1] | AA-8 | 2-Amino-1-(4-(dimethylamino)-4-(thiophen-2-yl)piperidin-1-yl)ethanone |
| 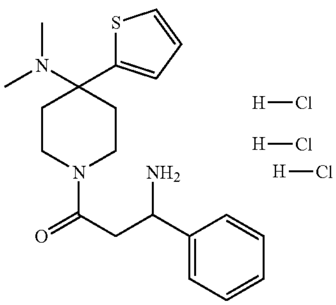 | AA-9 | 3-Amino-1-(4-(dimethylamino)-4-(thiophen-2-yl)piperidin-1-yl)-3-phenylpropan-1-one trihydrochloride |
| 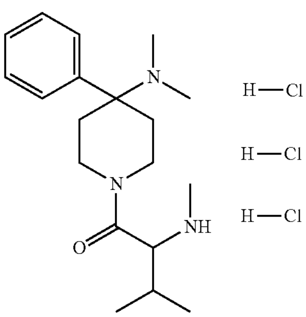 | AA-10 | 1-(4-(Dimethylamino)-4-phenylpiperidin-1-yl)-3-methyl-2-(methylamino)butan-1-one trihydrochloride |
| 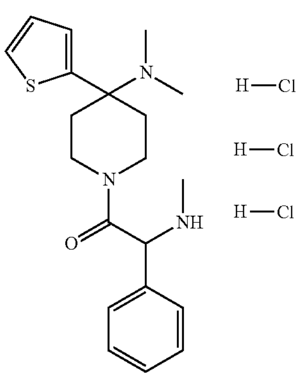 | AA-11 | 1-(4-(Dimethylamino)-4-(thiophen-2-yl)piperidin-1-yl)-2-(methylamino)-2-phenylethanone trihydrochloride |

-continued

| Structure | Amine Building Block No. | Amine Building Block Name |
|---|---|---|
| (structure) | AA-12 | (4-(Dimethylamino)-4-phenylpiperidin-1-yl)(piperidin-3-yl)methanone trihydrochloride |
| (structure) | AA-13 | (4-(Dimethylamino)-4-phenylpiperidin-1-yl)(indolin-3-yl)methanone trihydrochloride |

2 Indole Structural Units ACl

All indole building blocks (ACl) were commercially available at the time of synthesis.

| Structure | Indole Building Block ACl No. | Indole Building Block Name |
|---|---|---|
| (structure) | ACl-1 | 1H-Indole-3-carboxylic acid |
| (structure) | ACl-2 | 3-(1-Methyl-1H-indol-3-yl)propanoic acid |
| (structure) | ACl-3 | 3-(1H-Indol-3-yl)butanoic acid |

-continued

| Structure | Indole Building Block ACl No. | Indole Building Block Name |
|---|---|---|
| 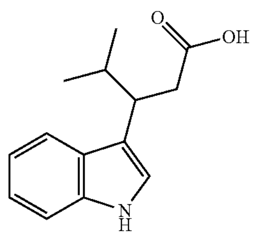 [SMILES: CC(C)C(CC(=O)O)c1c[nH]c2ccccc12] | ACl-4 | 3-(1H-Indol-3-yl)-4-methylpentanoic acid |
| 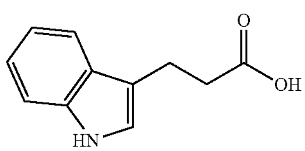 [SMILES: O=C(O)CCc1c[nH]c2ccccc12] | ACl-5 | 3-(1H-Indol-3-yl)propanoic acid |
| 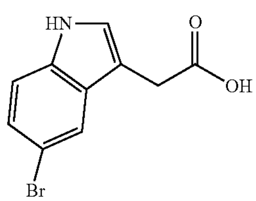 [SMILES: O=C(O)Cc1c[nH]c2ccc(Br)cc12] | ACl-6 | 2-(5-Bromo-1H-indol-3-yl)acetic acid |
| 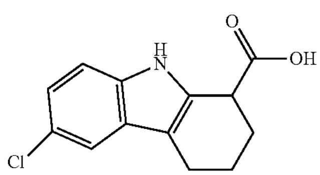 [SMILES: O=C(O)C1CCCc2c1[nH]c1ccc(Cl)cc21] | ACl-7 | 6-Chloro-2,3,4,9-tetrahydro-1H-carbazole-1-carboxylic acid |
| 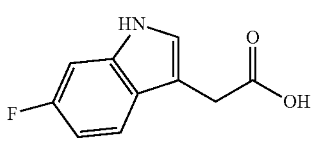 [SMILES: O=C(O)Cc1c[nH]c2cc(F)ccc12] | ACl-8 | 2-(6-Fluoro-1H-indol-3-yl)acetic acid |
| 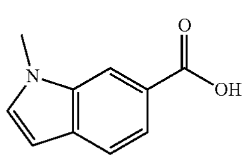 | ACl-9 | 1-Methyl-1H-indole-6-carboxylic acid |
| 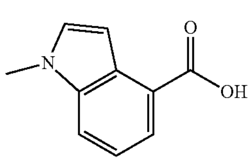 | ACl-10 | 1-Methyl-1H-indole-4-carboxylic acid |
| 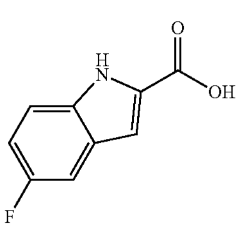 [SMILES: O=C(O)c1cc2cc(F)ccc2[nH]1] | ACl-11 | 5-Fluoro-1H-indole-2-carboxylic acid |

-continued

| Structure | Indole Building Block ACl No. | Indole Building Block Name |
|---|---|---|
| (structure) | ACl-12 | 5-Methoxy-1H-indole-2-carboxylic acid |
| (structure) | ACl-13 | 1H-Indole-6-carboxylic acid |
| (structure) | ACl-14 | 6-(Dimethylamino)-1H-indole-2-carboxylic acid |

3) Indole Structural Units ALD

All indole building blocks (ALD) were commercially available at the time of synthesis.

| Structure | Indole Building Block ALD No. | Indole Building Block Name |
|---|---|---|
| (structure) | ALD-1 | 5-Bromo-1H-indole-3-carbaldehyde |
| (structure) | ALD-2 | 1H-Indole-3-carbaldehyde |
| (structure) | ALD-3 | 6-Methoxy-1,2-dimethyl-1H-indole-3-carbaldehyde |

-continued

| Structure | Indole Building Block ALD No. | Indole Building Block Name |
|---|---|---|
| 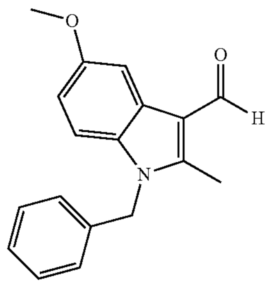 [SMILES: COc1ccc2c(c1)c(C=O)c(C)n2Cc1ccccc1] | ALD-4 | 1-Benzyl-5-methoxy-2-methyl-1H-indole-3-carbaldehyde |
| 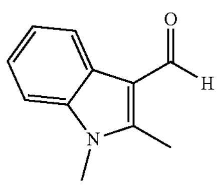 | ALD-5 | 1,2-Dimethyl-1H-indole-3-carbaldehyde |
| 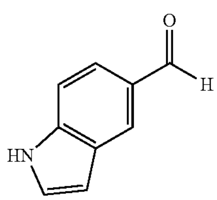 [SMILES: O=Cc1ccc2[nH]ccc2c1] | ALD-6 | 1H-Indole-5-carbaldehyde |
| 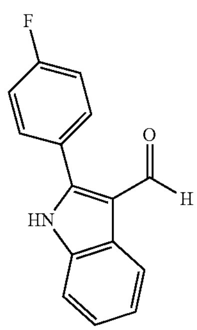 [SMILES: O=Cc1c(-c2ccc(F)cc2)[nH]c2ccccc12] | ALD-7 | 2-(4-Fluorophenyl)-1H-indole-3-carbaldehyde |
| 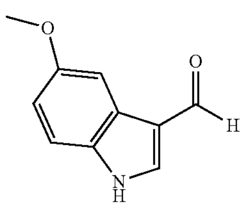 | ALD-8 | 5-Methoxy-1H-indole-3-carbaldehyde |
| 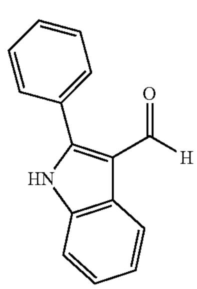 [SMILES: O=Cc1c(-c2ccccc2)[nH]c2ccccc12] | ALD-9 | 2-Phenyl-1H-indole-3-carbaldehyde |

-continued

| Structure | Indole Building Block ALD No. | Indole Building Block Name |
|---|---|---|
| 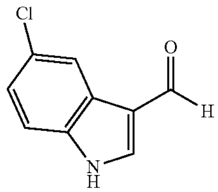 [SMILES: O=Cc1c[nH]c2ccc(Cl)cc12] | ALD-10 | 5-Chloro-1H-indole-3-carbaldehyde |
| 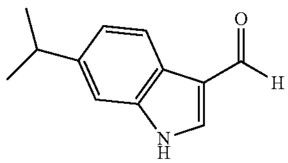 | ALD-11 | 6-Isopropyl-1H-indole-3-carbaldehyde |
| 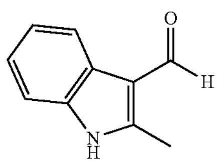 | ALD-12 | 2-Methyl-1H-indole-3-carbaldehyde |
| 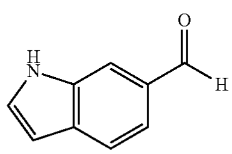 [SMILES: O=Cc1ccc2cc[nH]c2c1] | ALD-13 | 1H-Indole-6-carbaldehyde |
| 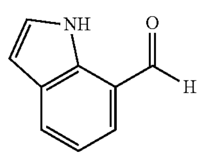 [SMILES: O=Cc1cccc2cc[nH]c12] | ALD-14 | 1H-Indole-7-carbaldehyde |
| 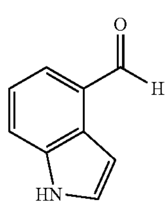 [SMILES: O=Cc1cccc2[nH]ccc12] | ALD-15 | 1H-Indole-4-carbaldehyde |

Solid Substances

Example 1

N-(2-(4-(Dimethylamino)-4-phenylpiperidin-1-yl)ethyl)-N-methyl-1H-indol-6-amide A solution of 1H-indole-6-carboxylic acid (1 eq/0.637 mmol/102 mg), 1-hydroxybenzotriazole hydrate (1 eq/0.637 mmol/84 mg) and N-ethyl diisopropylamine (5 eq/3.185 mmol/0.54 ml) in 5 ml tetrahydrofuran was cooled to 0° C., mixed with 1-(3-dimethylaminopropyl)-3-ethylcarbodiimide hydrochloride (1.5 eq/0.956 mmol/181 mg) and stirred for 15 min at 0° C. N,N-Dimethyl-1-(2-(methylamino)ethyl)-4-phenylpiperidin-4-amine (1.5 eq/0.956 mmol/250 mg) was added to this reaction mixture and it was heated to room temperature and stirred for 12 h.

The reaction course was monitored by thin-layer chromatography (75% EtOAc/hexane). Once the conversion was complete, the reaction mixture was washed 3 times with saturated sodium hydrogen carbonate solution and the organic phase was dried over magnesium sulfate. Following removal of the solvent under reduced pressure, the residue was purified by column chromatography (alumina neutral; 1% MeOH/CH$_2$Cl$_2$). 198 mg (76%) of product were obtained in the form of a yellow oil.

HPLC/MS analysis[1]: R$_t$=1.8 min; purity (UV 200-400 nm) 99%; m/z=405.3 [MH]$^+$, 360.3 [M-N(CH$_3$)$_2$]$^+$

[1] Equipment and methods for HPLC-MS analysis: HPLC: Waters Alliance 2795 with PDA Waters 996; MS: ZQ 2000 MassLynx Single Quadrupol MS Detector; Column: Waters Atlantis™ dC18, 3 µm, 2.1×30 mm; Column temperature: 40° C., Eluent A: purified water+0.1% formic acid; Eluent B: acetonitrile (gradient grade)+0.1% formic acid; Gradient: 0% B to 100% B in 8.8 min, 100% B for 0.4 min, 100% B to 0% B in 0.01 min, 0% B for 0.8 min; Flow: 1.0 ml/min; Ionisation: ES+, 25 V; Make-up: 100 µl/min 70% methanol+0.2% formic acid; UV: 200-400 nm.

Example 2

N-(2-(4-(Dimethylamino)-4-(thiophen-2-yl)piperidin-1-yl)ethyl)-3-(1H-indol-3-yl)-4-methylpentanamide A solution of 3-(1H-indol-3-yl)-4-methylpentanoic acid (1 eq/0.459 mmol/106 mg), 1-hydroxybenzotriazole hydrate (1 eq/0.459 mmol/61 mg) and N-ethyl diisopropylamine (5 eq/2.295 mmol/0.4 ml) in 3.5 ml tetrahydrofuran was cooled to 0° C., mixed with 1-(3-dimethylaminopropyl)-3-ethylcarbodiimide hydrochloride (1.5 eq/0.689 mmol/130 mg) and stirred for 15 min at 0° C. 1-(2-Aminoethyl)-N,N-dimethyl-4-(thiophen-2-yl)piperidin-4-amine trihydrochloride (1.5 eq/0.689 mmol/250 mg) was added to this reaction mixture and it was heated to room temperature and stirred for 12 h.

The reaction course was monitored by thin-layer chromatography (75% EtOAc/hexane). Once the conversion was complete, the reaction mixture was washed 3 times with saturated sodium hydrogen carbonate solution and the organic phase was dried over magnesium sulfate. Following removal of the solvent under reduced pressure, the residue was purified by column chromatography (alumina neutral; 1% MeOH/CH$_2$Cl$_2$). 143 mg (67%) of product were obtained in the form of a yellow oil.

HPLC/MS analysis[1]: R$_t$=2.4 min; purity (UV 200-400 nm) 99%; m/z=467.3 [MH]$^+$, 422.3 [M-N(CH$_3$)$_2$]$^+$

Example 3

N-(2-(4-(Dimethylamino)-4-phenylpiperidin-1-yl)ethyl)-5-fluoro-N-methyl-1H-indol-2-amide A solution of 5-fluoro-1H-indole-2-carboxylic acid (1 eq/0.637 mmol/114 mg), 1-hydroxybenzotriazole hydrate (1 eq/0.637 mmol/84 mg) and N-ethyl diisopropylamine (5 eq/3.185 mmol/0.54 ml) in 5 ml tetrahydrofuran was cooled to 0° C., mixed with 1-(3-dimethylaminopropyl)-3-ethylcarbodiimide hydrochloride (1.5 eq/0.956 mmol/181 mg) and stirred for 15 min at 0° C. N,N-Dimethyl-1-(2-(methylamino)ethyl)-4-phenylpiperidin-4-amine (1.5 eq/0.956 mmol/250 mg) was added to this reaction mixture and it was heated to room temperature and stirred for 12 h.

The reaction course was monitored by thin-layer chromatography (75% EtOAc/hexane). Once the conversion was complete, the reaction mixture was washed 3 times with saturated sodium hydrogen carbonate solution and the organic phase was dried over magnesium sulfate. Following removal of the solvent under reduced pressure, the residue was purified by column chromatography (alumina neutral; 1% MeOH/CH$_2$Cl$_2$). 138 mg (51%) of product were obtained in the form of a white solid.

HPLC/MS analysis[1]: R$_t$=2.1 min; purity (UV 200-400 nm) 99%; m/z=423.3 [MH]$^+$, 378.3 [M-N(CH$_3$)$_2$]$^+$ Library Substances
Parallel Synthesis of Acylated and Reductively Aminated Piperidine Derivatives
General:

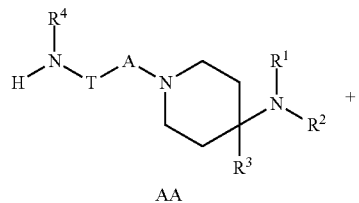

AA

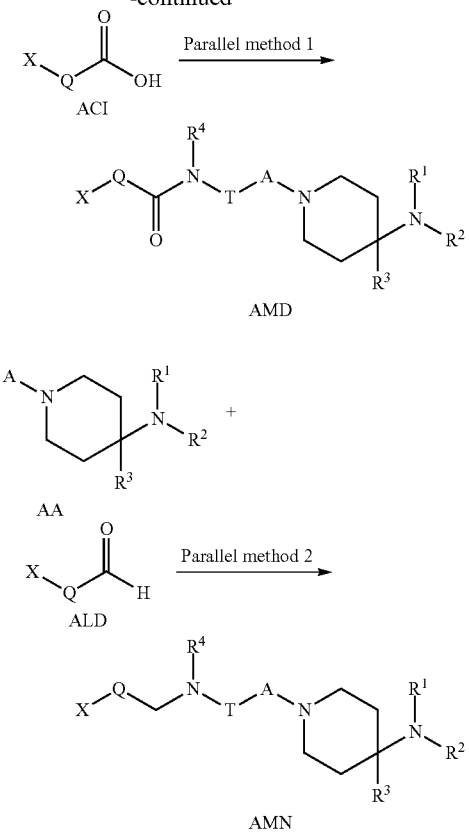

In accordance with the scheme above, the amine structural units AA were converted by parallel synthesis both with acids (ACI) and with aldehydes (ALD) to the acylated (AMD) and reductively aminated (AMN) products.

The crude products of the parallel synthesis were analysed by HPLC-MS[2] and then purified by reverse phase HPLC-MS[3]. The products were able to be identified by means of analytical HPLC-MS measurements[2].

[2] Equipments and methods for HPLC-MS analysis:

Parallel synthesis method 1: HPLC: Waters Alliance 2795 with PDA Waters 996; MS: ZQ 2000 MassLynx Single Quadrupol MS Detector; Column: Nucleodur Gravity C18 30×2 mm, 5 µm; Col. temp.: 40° C., Eluent A: purified water+0.1% formic acid; Eluent B: methanol (gradient grade)+0.1% formic acid; Gradient: 0% B to 100% B in 2.3 min, 100% B for 0.4 min, 100% B to 0% B in 0.01 min, 0% B for 0.8 min; Flow: 1.0 ml/min; Ionisation: ES+, 25V; make up: 100 µl/min 70% methanol+0.2% formic acid; UV: 200-400 nm Parallel synthesis method 2: HPLC: Waters Alliance 2795 with PDA Waters 996; MS: ZQ 2000 MassLynx Single Quadrupol MS Detector; Column: Waters Atlantis™ dC18, 3 µm, 2.1×30 mm; Col. temp.: 40° C., Eluent A: purified water+ 0.1% formic acid; Eluent B: acetonitrile(gradient grade)+ 0.1% formic acid; Gradient: 0% B to 100% B in 2.0 min, 100% B for 0.1 min, 100% B to 0% B in 0.01 min, 0% B for 0.5 min; Flow: 1.2 ml/min; Ionisation: ES+, 25V; make up: 100 µl/min 70% methanol+0.2% formic acid; UV: 200-400 nm

[3] Equipment and methods for HPLC-MS purification: Prep Pump: Waters 2525; Make Up Pump: Waters 515; Auxiliary Detector: Waters DAD 2487; MS Detector: Waters Micromass ZQ; Injector/Fraction Collector: Waters Sample Manager 2767; Gradient: Initial: 50% Water 50% Methanol->2-17 min: 0% Water 100% Methanol; Flow: 35 ml/min Column: Phenomenex Gemini, C18, 100×21.2 mm, Axia, 110A, 5µ

Parallel Synthesis Method 1:

Synthesis Procedure for the Acylation of the Amino Piperidine Derivatives (Aa) with Indole Carboxylic Acids (ACI)

Synthesis Procedure for Method 1:

A solution of the indole carboxylic acid derivative ACI (150 μmol) in 1.6 ml dichloromethane was prepared at room temperature and a solution of carbonyldiimidazole (160 μmol) in 1 ml dichloromethane was added. The reaction mixture was shaken for 1 hour at room temperature and then a solution of the corresponding amine AA (100 μmol) in a mixture of 500 μmol N-ethyl-diisopropylamine and 0.5 ml dichloromethane was added. The reaction mixture was shaken for 12 hours at room temperature. The solvent was then removed under vacuum in a vacuum centrifuge (GeneVac). The final purification was performed by HPLC-MS. The final analysis was performed by LC-MS.

Parallel Synthesis Method 2:
Synthesis Procedure for the Reductive Amination of the Amino Piperidine Derivatives (AA) with Indole Aldehydes (ALD)
Synthesis Procedure for Method 2:

A solution of the amine AA (100 μmol) in 1.0 ml methanol was prepared at room temperature and a solution of the corresponding aldehyde ALD (100 μmol) in 1.0 ml methanol was added. The reaction mixture obtained was mixed with 41 mg aluminium oxide and shaken for 2 hours at room temperature. 10.1 μl borane-pyridine complex were then added and the reaction mixture was shaken for 3 days at room temperature.

For the purposes of processing, 1.5 ml of ½ concentrated hydrochloric acid were added to the batches and they were shaken for 15 minutes at room temperature. Then 1 ml 6 M sodium hydroxide solution and 3 ml ethyl acetate were added.

Further processing took place on a Myriad-Allex processing system (Mettler-Toledo). After mixing thoroughly, the organic phase was separated off, the aqueous phase extracted with 3 ml ethyl acetate and the organic phases combined. Removal of the solvent took place under vacuum in a vacuum centrifuge (GeneVac). Purification was performed by HPLC-MS.

Analysis was performed by LC-MS.

| Structure | Example (Entry No.) | Synthesis procedure | Amine structural unit | Acid/aldehyde structural unit | M+ [g/mol] | R$_t$ [min] |
|---|---|---|---|---|---|---|
| 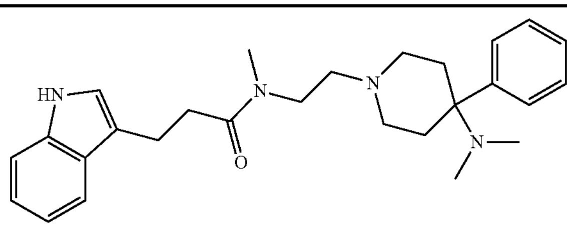 | 4 (AMD-4) | Parallel synthesis method 1 | AA-1 | 3-(1H-Indol-3-yl)propanoic acid | 433.4 | 1.17 |
| 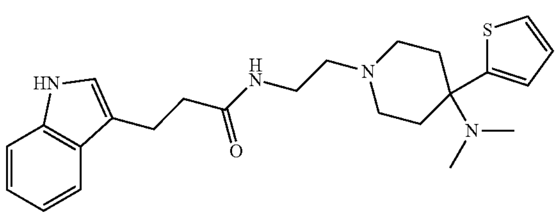 [SMILES: CN(C)C1(c2cccs2)CCN(CCNC(=O)CCc2c[nH]c3ccccc23)CC1] | 5 (AMD-5) | Parallel synthesis method 1 | AA-3 | 3-(1H-Indol-3-yl)propanoic acid | 425.3 | 1.1 |
| 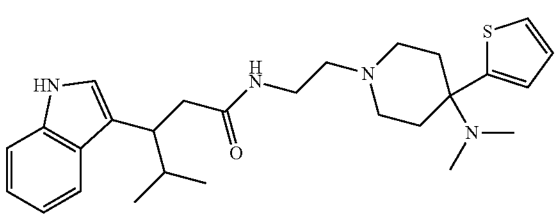 [SMILES: CC(C)C(CC(=O)NCCN1CCC(c2cccs2)(N(C)C)CC1)c1c[nH]c2ccccc12] | 6 (AMD-6) | Parallel synthesis method 1 | AA-3 | 3-(1H-Indol-3-yl)-4-methylpentanoic acid | 467.3 | 1.38 |
| 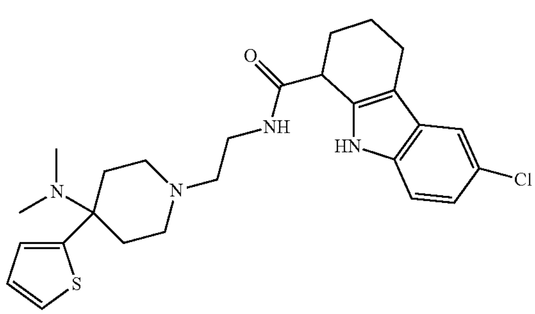 [SMILES: CN(C)C1(c2cccs2)CCN(CCNC(=O)C2CCCc3c2[nH]c2ccc(Cl)cc32)CC1] | 7 (AMD-7) | Parallel synthesis method 1 | AA-3 | 6-Chloro-2,3,4,9-tetrahydro-1H-carbazole-1-carboxylic acid | 406.3 | 1.51 |

-continued

| Structure | Example (Entry No.) | Synthesis procedure | Amine structural unit | Acid/aldehyde structural unit | M+ [g/mol] | R_t [min] |
|---|---|---|---|---|---|---|
| 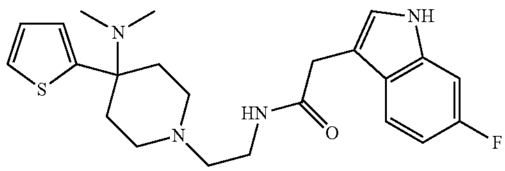 [SMILES: CN(C)C1(c2cccs2)CCN(CCNC(=O)Cc2c[nH]c3cc(F)ccc23)CC1] | 8 (AMD-8) | Parallel synthesis method 1 | AA-3 | 2-(6-Fluoro-1H-indol-3-yl)acetic acid | 429.3 | 1.07 |
| 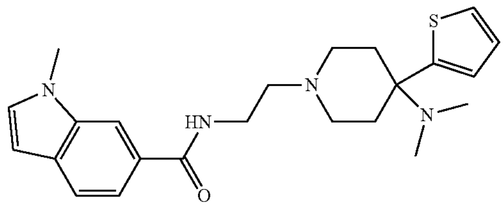 [SMILES: CN(C)C1(c2cccs2)CCN(CCNC(=O)c2ccc3ccn(C)c3c2)CC1] | 9 (AMD-9) | Parallel synthesis method 1 | AA-3 | 1-Methyl-1H-indole-6-carboxylic acid | 411.3 | 1.11 |
| 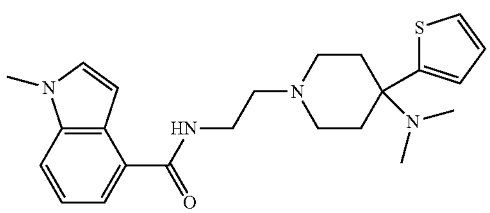 [SMILES: CN(C)C1(c2cccs2)CCN(CCNC(=O)c2cccc3c2ccn3C)CC1] | 10 (AMD-10) | Parallel synthesis method 1 | AA-3 | 1-Methyl-1H-indole-4-carboxylic acid | 411.3 | 1.06 |
| 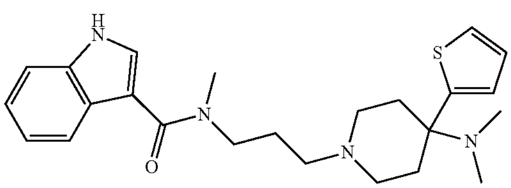 [SMILES: CN(CCCN1CCC(c2cccs2)(N(C)C)CC1)C(=O)c1c[nH]c2ccccc12] | 11 (AMD-11) | Parallel synthesis method 1 | AA-6 | 1H-Indole-3-carboxylic acid | 425.3 | 1.07 |
| 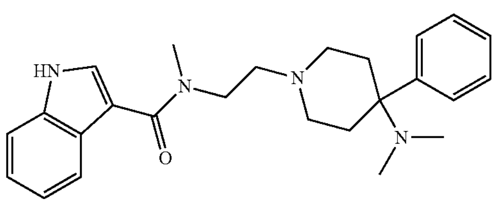 [SMILES: CN(CCN1CCC(c2ccccc2)(N(C)C)CC1)C(=O)c1c[nH]c2ccccc12] | 12 (AMD-12) | Parallel synthesis method 1 | AA-1 | 1H-Indole-3-carboxylic acid | 405.3 | 1.09 |
| 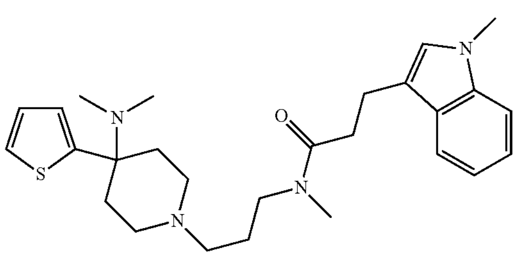 [SMILES: CN(CCCN1CCC(c2cccs2)(N(C)C)CC1)C(=O)CCc1cn(C)c2ccccc12] | 13 (AMD-13) | Parallel synthesis method 1 | AA-6 | 3-(1-Methyl-1H-indol-3-yl)propanoic acid | 467.3 | 1.24 |
| 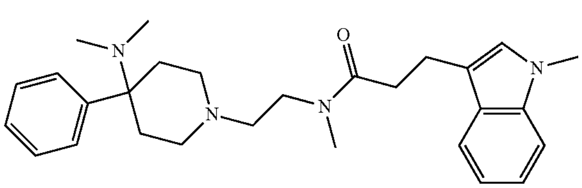 [SMILES: CN(CCN1CCC(c2ccccc2)(N(C)C)CC1)C(=O)CCc1cn(C)c2ccccc12] | 14 (AMD-14) | Parallel synthesis method 1 | AA-1 | 3-(1-Methyl-1H-indol-3-yl)propanoic acid | 447.4 | 1.48 |

-continued

| Structure | Example (Entry No.) | Synthesis procedure | Amine structural unit | Acid/aldehyde structural unit | M+ [g/mol] | R$_t$ [min] |
|---|---|---|---|---|---|---|
| 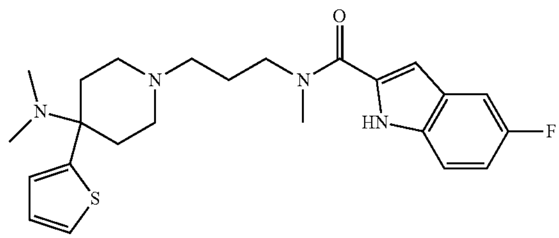 [SMILES: CN(CCCN1CCC(c2cccs2)(N(C)C)CC1)C(=O)c1cc2cc(F)ccc2[nH]1] | 15 (AMD-15) | Parallel synthesis method 1 | AA-6 | 5-Fluoro-1H-indole-2-carboxylic acid | 443.3 | 1.19 |
| 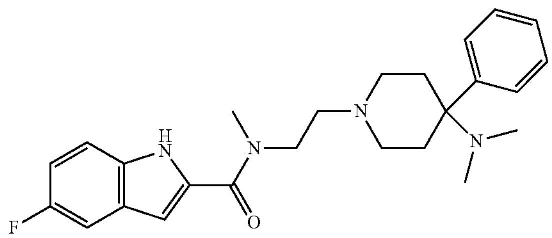 [SMILES: CN(CCN1CCC(c2ccccc2)(N(C)C)CC1)C(=O)c1cc2cc(F)ccc2[nH]1] | 16 (AMD-16) | Parallel synthesis method 1 | AA-1 | 5-Fluoro-1H-indole-2-carboxylic acid | 423.3 | 1.22 |
| 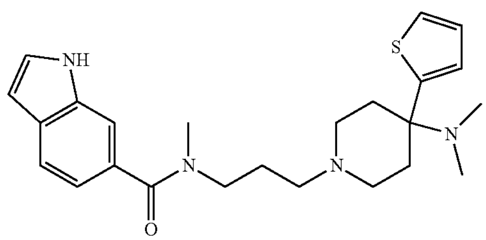 [SMILES: CN(CCCN1CCC(c2cccs2)(N(C)C)CC1)C(=O)c1ccc2cc[nH]c2c1] | 17 (AMD-17) | Parallel synthesis method 1 | AA-6 | 1H-Indole-6-carboxylic acid | 425.3 | 1.09 |
| 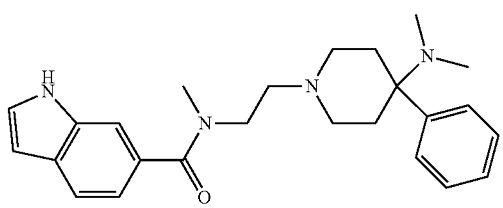 [SMILES: CN(CCN1CCC(c2ccccc2)(N(C)C)CC1)C(=O)c1ccc2cc[nH]c2c1] | 18 (AMD-18) | Parallel synthesis method 1 | AA-1 | 1H-Indole-6-carboxylic acid | 405.3 | 1.12 |
| 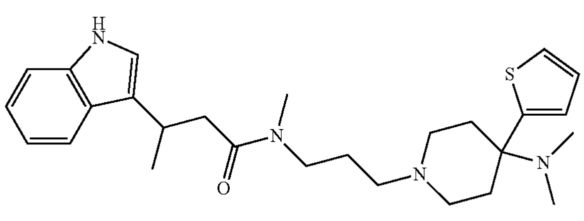 [SMILES: CC(CC(=O)N(C)CCCN1CCC(c2cccs2)(N(C)C)CC1)c1c[nH]c2ccccc12] | 19 (AMD-19) | Parallel synthesis method 1 | AA-6 | 3-(1H-Indol-3-yl)butanoic acid | 467.3 | 1.25 |
| 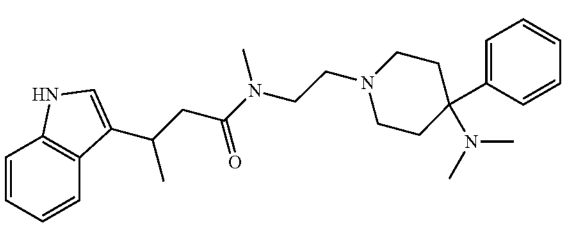 | 20 (AMD-20) | Parallel synthesis method 1 | AA-1 | 3-(1H-Indol-3-yl)butanoic acid | 447.4 | 1.49 |

-continued

| Structure | Example (Entry No.) | Synthesis procedure | Amine structural unit | Acid/aldehyde structural unit | M+ [g/mol] | R$_t$ [min] |
|---|---|---|---|---|---|---|
| 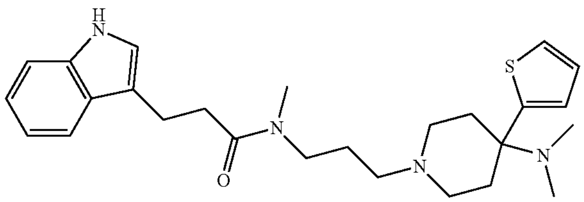 [SMILES: CN(CCCN1CCC(c2cccs2)(N(C)C)CC1)C(=O)CCc1c[nH]c2ccccc12] | 21 (AMD-21) | Parallel synthesis method 1 | AA-6 | 3-(1H-Indol-3-yl)propanoic acid | 453.3 | 1.15 |
| 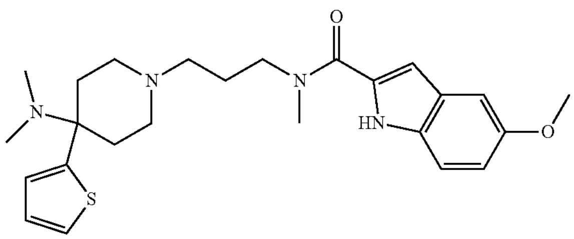 | 22 (AMD-22) | Parallel synthesis method 1 | AA-6 | 5-Methoxy-1H-indole-2-carboxylic acid | 455.3 | 1.19 |
| 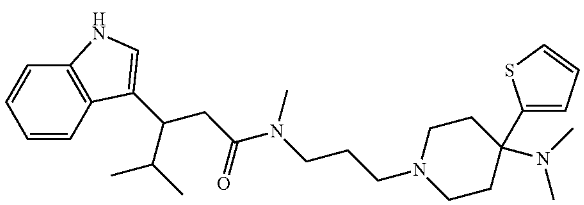 [SMILES: CC(C)C(CC(=O)N(C)CCCN1CCC(c2cccs2)(N(C)C)CC1)c1c[nH]c2ccccc12] | 23 (AMD-23) | Parallel synthesis method 1 | AA-6 | 3-(1H-Indol-3-yl)-4-methylpentanoic acid | 495.4 | 1.38 |
| 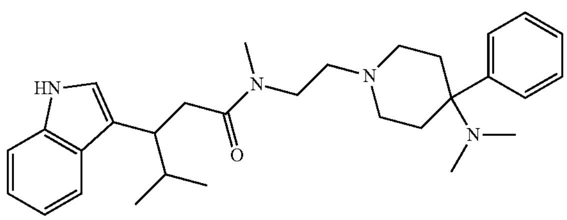 [SMILES: CC(C)C(CC(=O)N(C)CCN1CCC(c2ccccc2)(N(C)C)CC1)c1c[nH]c2ccccc12] | 24 (AMD-24) | Parallel synthesis method 1 | AA-1 | 3-(1H-Indol-3-yl)-4-methylpentanoic acid | 475.4 | 1.46 |
| 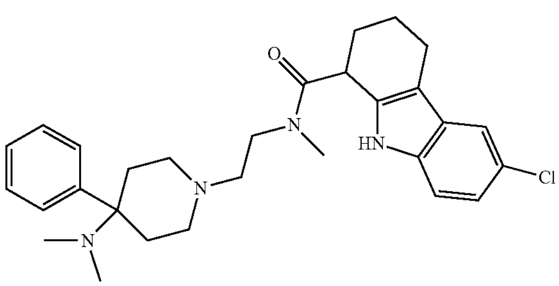 [SMILES: CN(CCN1CCC(c2ccccc2)(N(C)C)CC1)C(=O)C1CCCc2c1[nH]c1ccc(Cl)cc21] | 25 (AMD-25) | Parallel synthesis method 1 | AA-1 | 6-Chloro-2,3,4,9-tetrahydro-1H-carbazole-1-carboxylic acid | 493.4 | 1.53 |
| 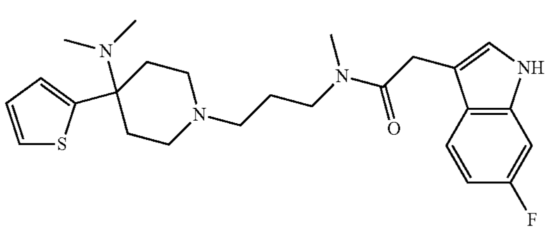 [SMILES: CN(CCCN1CCC(c2cccs2)(N(C)C)CC1)C(=O)Cc1c[nH]c2cc(F)ccc12] | 26 (AMD-26) | Parallel synthesis method 1 | AA-6 | 2-(6-Fluoro-1H-indol-3-yl)acetic acid | 457.3 | 1.15 |

-continued

| Structure | Example (Entry No.) | Synthesis procedure | Amine structural unit | Acid/aldehyde structural unit | M+ [g/mol] | R_t [min] |
|---|---|---|---|---|---|---|
| 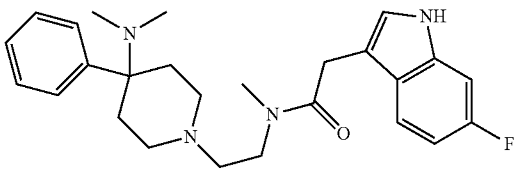 [SMILES: CN(CCN1CCC(c2ccccc2)(N(C)C)CC1)C(=O)Cc1c[nH]c2cc(F)ccc12] | 27 (AMD-27) | Parallel synthesis method 1 | AA-1 | 2-(6-Fluoro-1H-indol-3-yl)acetic acid | 437.3 | 1.13 |
| 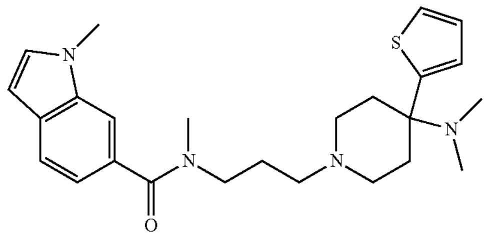 [SMILES: CN(CCCN1CCC(c2cccs2)(N(C)C)CC1)C(=O)c1ccc2ccn(C)c2c1] | 28 (AMD-28) | Parallel synthesis method 1 | AA-6 | 1-Methyl-1H-indole-6-carboxylic acid | 439.3 | 1.15 |
| 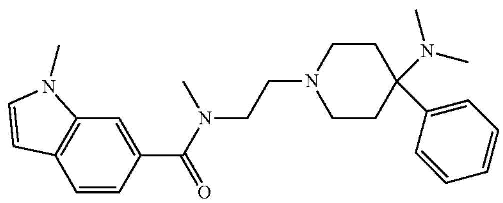 [SMILES: CN(CCN1CCC(c2ccccc2)(N(C)C)CC1)C(=O)c1ccc2ccn(C)c2c1] | 29 (AMD-29) | Parallel synthesis method 1 | AA-1 | 1-Methyl-1H-indole-6-carboxylic acid | 419.3 | 0.25 |
| 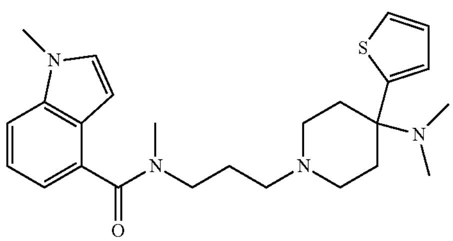 [SMILES: CN(CCCN1CCC(c2cccs2)(N(C)C)CC1)C(=O)c1cccc2c1ccn2C] | 30 (AMD-30) | Parallel synthesis method 1 | AA-6 | 1-Methyl-1H-indole-4-carboxylic acid | 439.3 | 0.26 |
| 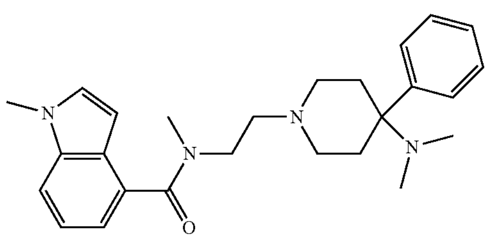 [SMILES: CN(CCN1CCC(c2ccccc2)(N(C)C)CC1)C(=O)c1cccc2c1ccn2C] | 31 (AMD-31) | Parallel synthesis method 1 | AA-1 | 1-Methyl-1H-indole-4-carboxylic acid | 419.3 | 1.17 |
| 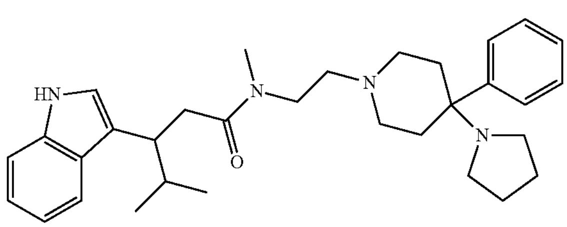 [SMILES: CC(C)C(CC(=O)N(C)CCN1CCC(c2ccccc2)(N2CCCC2)CC1)c1c[nH]c2ccccc12] | 32 (AMD-32) | Parallel synthesis method 1 | AA-2 | 3-(1H-Indol-3-yl)-4-methylpentanoic acid | 501.3 | 1.17 |

-continued

| Structure | Example (Entry No.) | Synthesis procedure | Amine structural unit | Acid/aldehyde structural unit | M+ [g/mol] | Rt [min] |
|---|---|---|---|---|---|---|
| 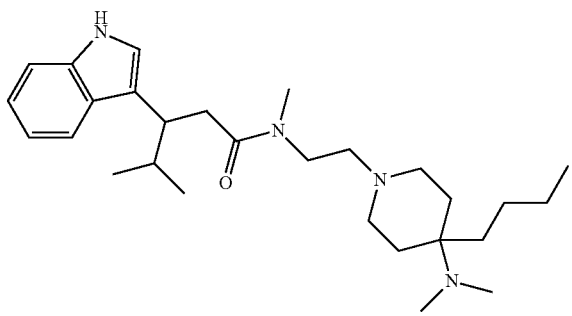 [SMILES: CCCCC1(N(C)C)CCN(CCN(C)C(=O)CC(c2c[nH]c3ccccc23)C(C)C)CC1] | 33 (AMD-33) | Parallel synthesis method 1 | AA-4 | 3-(1H-Indol-3-yl)-4-methylpentanoic acid | 455.3 | 1.15 |
| 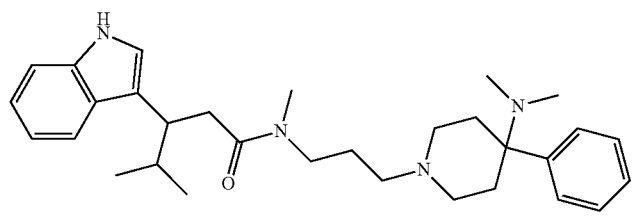 [SMILES: CC(C)C(CC(=O)N(C)CCCN1CCC(c2ccccc2)(N(C)C)CC1)c1c[nH]c2ccccc12] | 34 (AMD-34) | Parallel synthesis method 1 | AA-5 | 3-(1H-Indol-3-yl)-4-methylpentanoic acid | 489.3 | 1.15 |
| 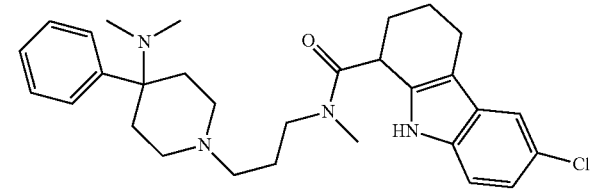 [SMILES: CN(CCCN1CCC(c2ccccc2)(N(C)C)CC1)C(=O)C1CCCc2c1[nH]c1ccc(Cl)cc21] | 35 (AMD-35) | Parallel synthesis method 1 | AA-5 | 6-Chloro-2,3,4,9-tetrahydro-1H-carbazole-1-carboxylic acid | 507.2 | 1.25 |
| 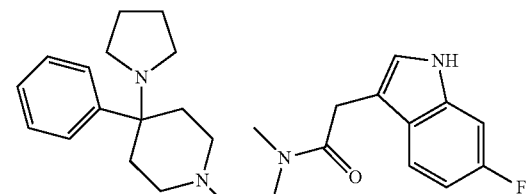 | 36 (AMD-36) | Parallel synthesis method 1 | AA-2 | 2-(6-Fluoro-1H-indol-3-yl)acetic acid | 463.3 | 1.05 |
| 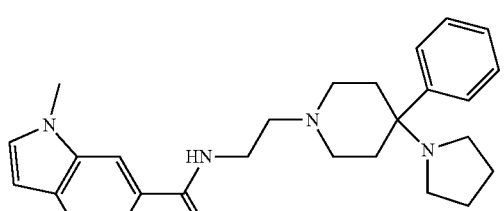 | 37 (AMD-37) | Parallel synthesis method 1 | AA-2 | 1-Methyl-1H-indole-6-carboxylic acid | 445.3 | 1.04 |
| 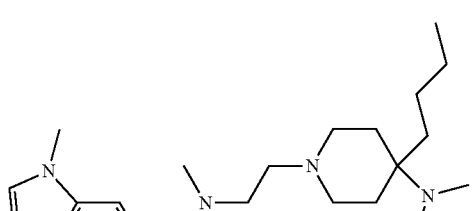 | 38 (AMD-38) | Parallel synthesis method 1 | AA-4 | 1-Methyl-1H-indole-6-carboxylic acid | 399.3 | 1.01 |

-continued

| Structure | Example (Entry No.) | Synthesis procedure | Amine structural unit | Acid/aldehyde structural unit | M+ [g/mol] | $R_t$ [min] |
|---|---|---|---|---|---|---|
| 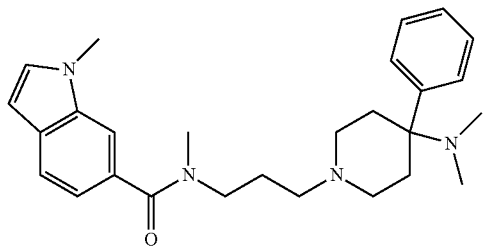 [SMILES: CN(CCCN1CCC(c2ccccc2)(N(C)C)CC1)C(=O)c1ccc2ccn(C)c2c1] | 39 (AMD-39) | Parallel synthesis method 1 | AA-5 | 1-Methyl-1H-indole-6-carboxylic acid | 433.3 | 1.04 |
| 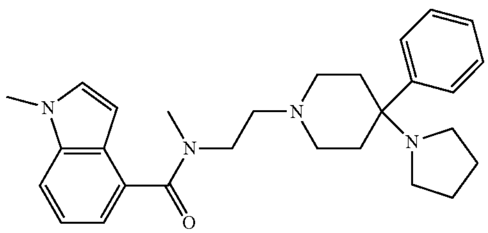 [SMILES: CN(CCN1CCC(c2ccccc2)(N2CCCC2)CC1)C(=O)c1cccc2c1ccn2C] | 40 (AMD-40) | Parallel synthesis method 1 | AA-2 | 1-Methyl-1H-indole-4-carboxylic acid | 445.2 | 1.02 |
| 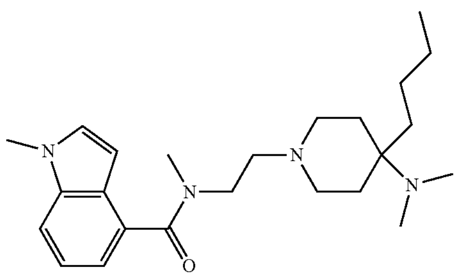 | 41 (AMD-41) | Parallel synthesis method 1 | AA-4 | 1-Methyl-1H-indole-4-carboxylic acid | 399.3 | 0.99 |
| 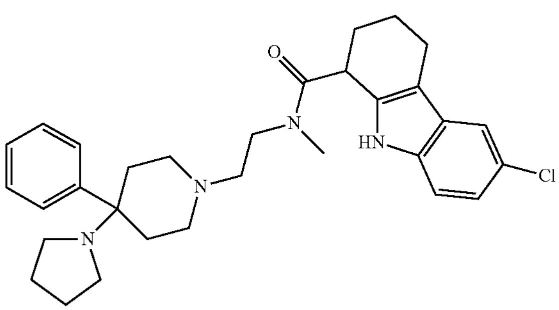 [SMILES: CN(CCN1CCC(c2ccccc2)(N2CCCC2)CC1)C(=O)C1CCCc2c1[nH]c1ccc(Cl)cc21] | 42 (AMD-42) | Parallel synthesis method 1 | AA-2 | 6-Chloro-2,3,4,9-tetrahydro-1H-carbazole-1-carboxylic acid | 519.2 | 1.26 |
| 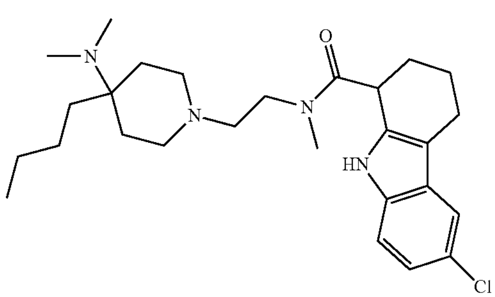 [SMILES: CCCCC1(N(C)C)CCN(CCN(C)C(=O)C2CCCc3c2[nH]c2ccc(Cl)cc32)CC1] | 43 (AMD-43) | Parallel synthesis method 1 | AA-4 | 6-Chloro-2,3,4,9-tetrahydro-1H-carbazole-1-carboxylic acid | 473.2 | 1.25 |

-continued

| Structure | Example (Entry No.) | Synthesis procedure | Amine structural unit | Acid/aldehyde structural unit | M+ [g/mol] | R$_t$ [min] |
|---|---|---|---|---|---|---|
| 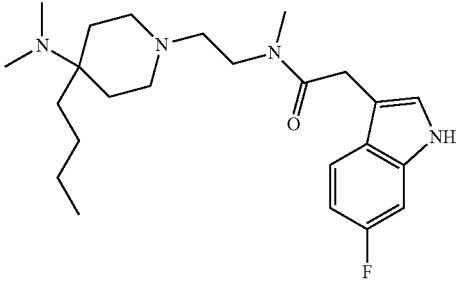 [SMILES: CCCCC1(N(C)C)CCN(CCN(C)C(=O)Cc2c[nH]c3cc(F)ccc23)CC1] | 44 (AMD-44) | Parallel synthesis method 1 | AA-4 | 2-(6-Fluoro-1H-indol-3-yl)acetic acid | 417.3 | 1.02 |
| 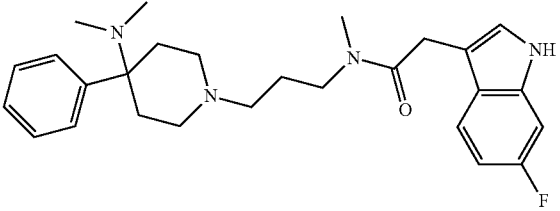 [SMILES: CN(CCCN1CCC(c2ccccc2)(N(C)C)CC1)C(=O)Cc1c[nH]c2cc(F)ccc12] | 45 (AMD-45) | Parallel synthesis method 1 | AA-5 | 2-(6-Fluoro-1H-indol-3-yl)acetic acid | 451.2 | 1.04 |
| 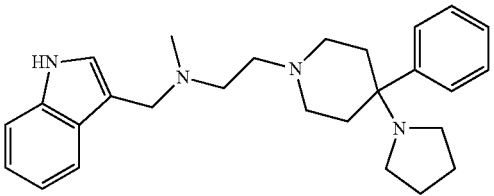 [SMILES: CN(CCN1CCC(c2ccccc2)(N2CCCC2)CC1)Cc1c[nH]c2ccccc12] | 46 (AMD-46) | Parallel synthesis method 1 | AA-2 | 1H-Indole-3-carboxylic acid | 431.2 | 0.99 |
| 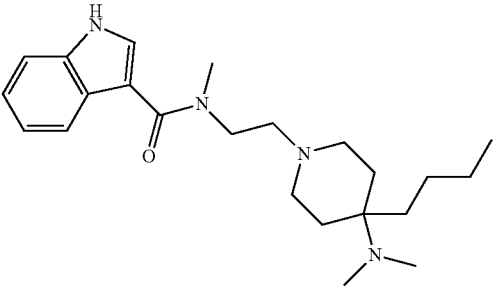 [SMILES: CCCCC1(N(C)C)CCN(CCN(C)C(=O)c2c[nH]c3ccccc23)CC1] | 47 (AMD-47) | Parallel synthesis method 1 | AA-4 | 1H-Indole-3-carboxylic acid | 385.3 | 0.96 |
| 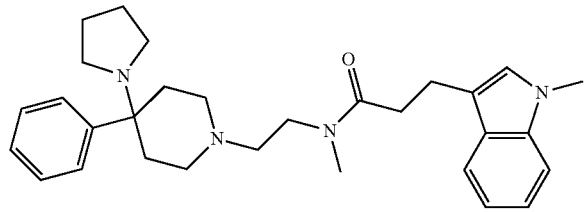 [SMILES: CN(CCN1CCC(c2ccccc2)(N2CCCC2)CC1)C(=O)CCc1cn(C)c2ccccc12] | 48 (AMD-48) | Parallel synthesis method 1 | AA-2 | 3-(1-Methyl-1H-indol-3-yl)propanoic acid | 473.3 | 1.08 |
| 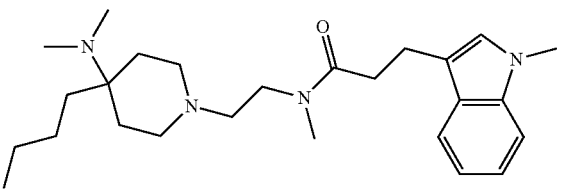 [SMILES: CCCCC1(N(C)C)CCN(CCN(C)C(=O)CCc2cn(C)c3ccccc23)CC1] | 49 (AMD-49) | Parallel synthesis method 1 | AA-4 | 3-(1-Methyl-1H-indol-3-yl)propanoic acid | 427.3 | 1.11 |

-continued

| Structure | Example (Entry No.) | Synthesis procedure | Amine structural unit | Acid/aldehyde structural unit | M+ [g/mol] | R_t [min] |
|---|---|---|---|---|---|---|
| 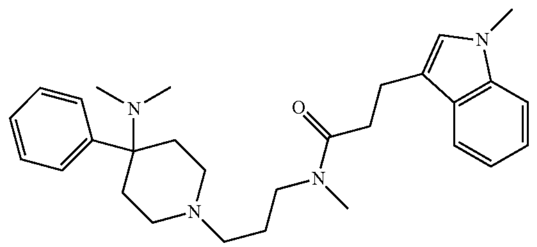 [SMILES: CN(CCCN1CCC(c2ccccc2)(N(C)C)CC1)C(=O)CCc1cn(C)c2ccccc12] | 50 (AMD-50) | Parallel synthesis method 1 | AA-5 | 3-(1-Methyl-1H-indol-3-yl)propanoic acid | 461.3 | 1.11 |
| 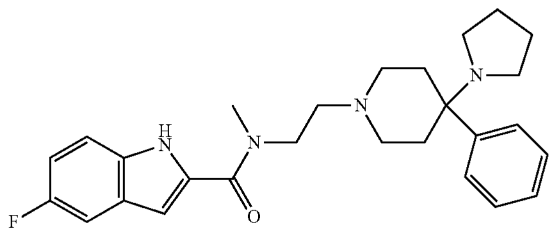 [SMILES: CN(CCN1CCC(c2ccccc2)(N2CCCC2)CC1)C(=O)c1cc2cc(F)ccc2[nH]1] | 51 (AMD-51) | Parallel synthesis method 1 | AA-2 | 5-Fluoro-1H-indole-2-carboxylic acid | 449.2 | 1.09 |
| 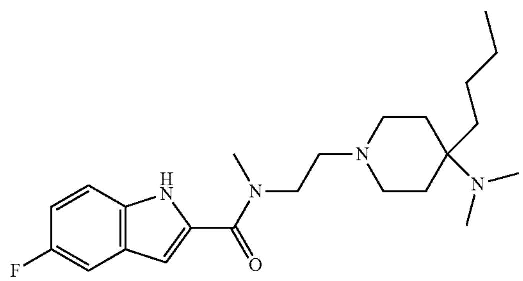 [SMILES: CCCCC1(N(C)C)CCN(CCN(C)C(=O)c2cc3cc(F)ccc3[nH]2)CC1] | 52 (AMD-52) | Parallel synthesis method 1 | AA-4 | 5-Fluoro-1H-indole-2-carboxylic acid | 403.3 | 1.08 |
| 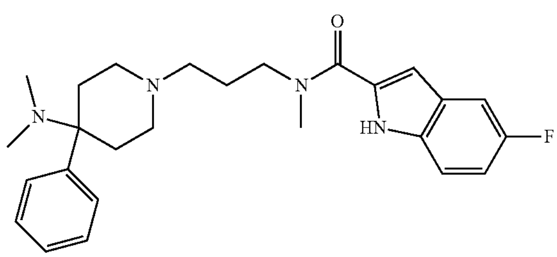 [SMILES: CN(CCCN1CCC(c2ccccc2)(N(C)C)CC1)C(=O)c1cc2cc(F)ccc2[nH]1] | 53 (AMD-53) | Parallel synthesis method 1 | AA-5 | 5-Fluoro-1H-indole-2-carboxylic acid | 437.2 | 1.09 |
| 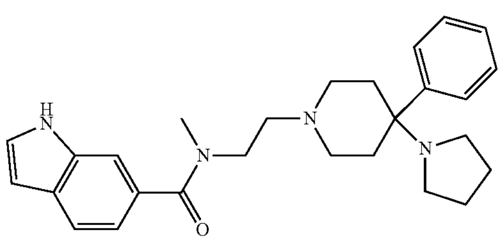 [SMILES: CN(CCN1CCC(c2ccccc2)(N2CCCC2)CC1)C(=O)c1ccc2cc[nH]c2c1] | 54 (AMD-54) | Parallel synthesis method 1 | AA-2 | 1H-Indole-6-carboxylic acid | 431.2 | 1 |
| 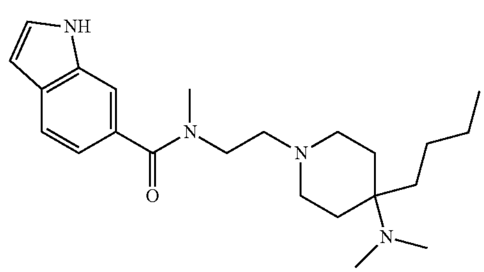 [SMILES: CCCCC1(N(C)C)CCN(CCN(C)C(=O)c2ccc3cc[nH]c3c2)CC1] | 55 (AMD-55) | Parallel synthesis method 1 | AA-4 | 1H-Indole-6-carboxylic acid | 385.3 | 0.97 |

-continued

| Structure | Example (Entry No.) | Synthesis procedure | Amine structural unit | Acid/aldehyde structural unit | M+ [g/mol] | R_t [min] |
|---|---|---|---|---|---|---|
| 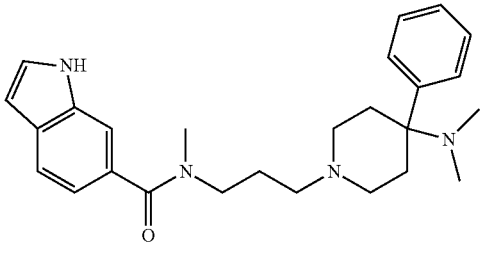 [SMILES: CN(CCCN1CCC(c2ccccc2)(N(C)C)CC1)C(=O)c1ccc2cc[nH]c2c1] | 56 (AMD-56) | Parallel synthesis method 1 | AA-5 | 1H-Indole-6-carboxylic acid | 419.2 | 1.01 |
| 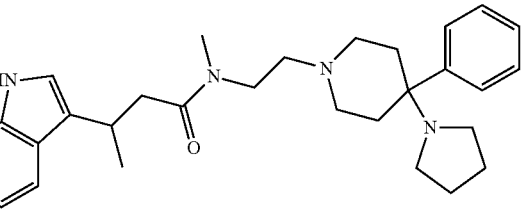 | 57 (AMD-57) | Parallel synthesis method 1 | AA-2 | 3-(1H-Indol-3-yl)butanoic acid | 473.3 | 1.08 |
| 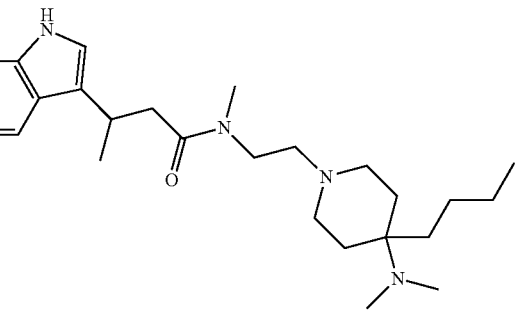 | 58 (AMD-58) | Parallel synthesis method 1 | AA-4 | 3-(1H-Indol-3-yl)butanoic acid | 427.3 | 1.09 |
| 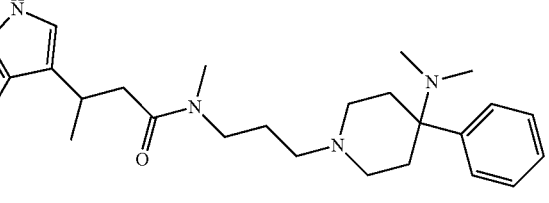 | 59 (AMD-59) | Parallel synthesis method 1 | AA-5 | 3-(1H-Indol-3-yl)butanoic acid | 461.3 | 1.09 |
| 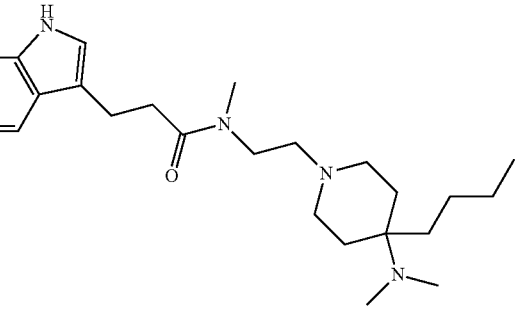 | 60 (AMD-60) | Parallel synthesis method 1 | AA-4 | 3-(1H-Indol-3-yl)propanoic acid | 413.3 | 1.02 |

-continued

| Structure | Example (Entry No.) | Synthesis procedure | Amine structural unit | Acid/aldehyde structural unit | M+ [g/mol] | R$_t$ [min] |
|---|---|---|---|---|---|---|
| 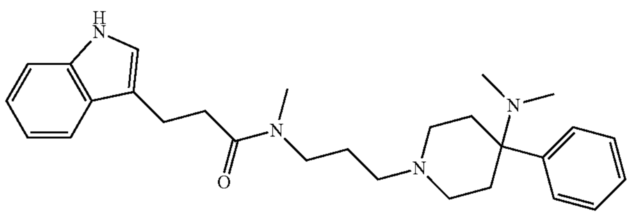 [SMILES: CN(CCCN1CCC(c2ccccc2)(N(C)C)CC1)C(=O)CCc1c[nH]c2ccccc12] | 61 (AMD-61) | Parallel synthesis method 1 | AA-5 | 3-(1H-Indol-3-yl)propanoic acid | 447.3 | 1.05 |
| 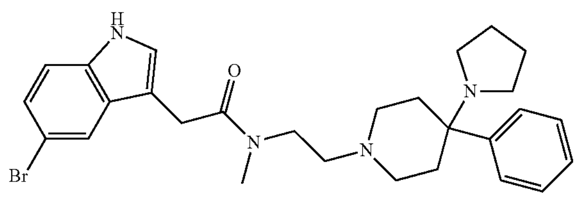 [SMILES: CN(CCN1CCC(c2ccccc2)(N2CCCC2)CC1)C(=O)Cc1c[nH]c2ccc(Br)cc12] | 62 (AMD-62) | Parallel synthesis method 1 | AA-2 | 2-(5-Bromo-1H-indol-3-yl)acetic acid | 523.2 | 1.13 |
| 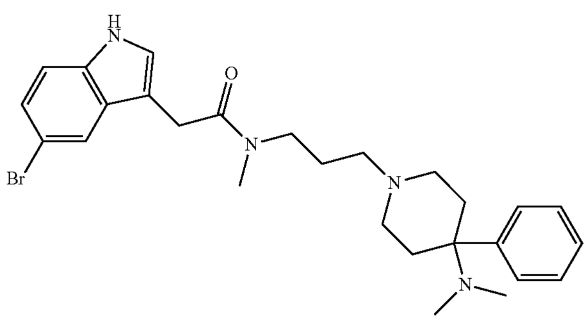 [SMILES: CN(CCCN1CCC(c2ccccc2)(N(C)C)CC1)C(=O)Cc1c[nH]c2ccc(Br)cc12] | 63 (AMD-63) | Parallel synthesis method 1 | AA-5 | 2-(5-Bromo-1H-indol-3-yl)acetic acid | 511.2 | 1.11 |
| 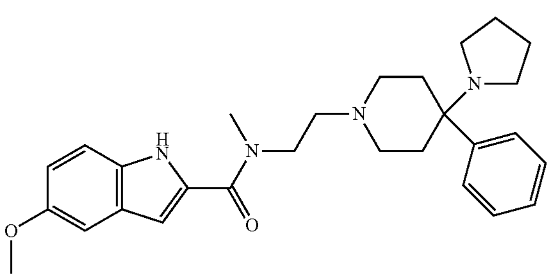 [SMILES: COc1ccc2[nH]c(C(=O)N(C)CCN3CCC(c4ccccc4)(N4CCCC4)CC3)cc2c1] | 64 (AMD-64) | Parallel synthesis method 1 | AA-2 | 5-Methoxy-1H-indole-2-carboxylic acid | 461.2 | 1.07 |
| 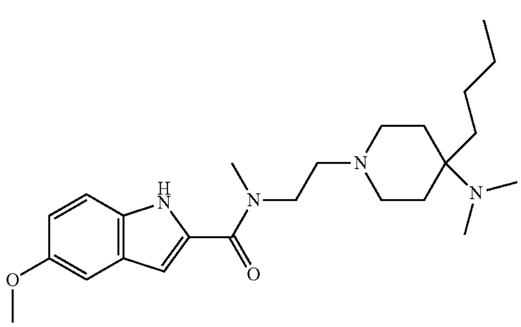 [SMILES: CCCCC1(N(C)C)CCN(CCN(C)C(=O)c2cc3cc(OC)ccc3[nH]2)CC1] | 65 (AMD-65) | Parallel synthesis method 1 | AA-4 | 5-Methoxy-1H-indole-2-carboxylic acid | 415.3 | 1.05 |

-continued

| Structure | Example (Entry No.) | Synthesis procedure | Amine structural unit | Acid/aldehyde structural unit | M+ [g/mol] | R_t [min] |
|---|---|---|---|---|---|---|
| 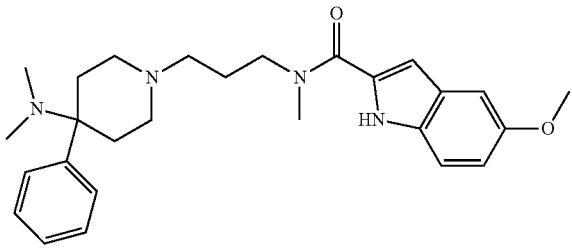 | 66 (AMD-66) | Parallel synthesis method 1 | AA-5 | 5-Methoxy-1H-indole-2-carboxylic acid | 449.2 | 1.07 |
| 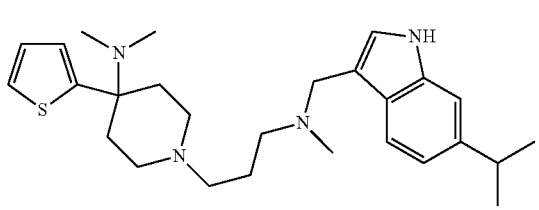 [SMILES: CC(C)c1ccc2c(CN(C)CCCN3CCC(c4cccs4)(N(C)C)CC3)c[nH]c2c1] | 67 (AMN-1) | Parallel synthesis method 2 | AA-6 | 6-Isopropyl-1H-indole-3-carbaldehyde | 453.2 | 1 |
| 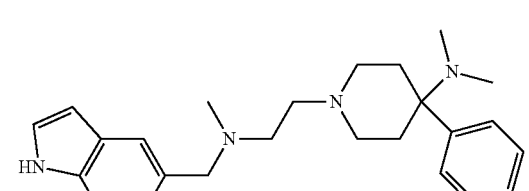 | 68 (AMN-2) | Parallel synthesis method 2 | AA-1 | 1H-Indole-5-carbaldehyde | 390.3 | 1.16 |
| 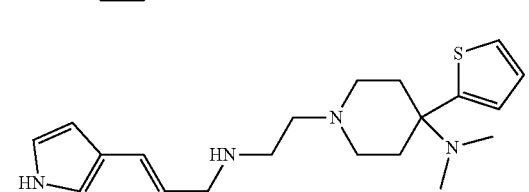 | 69 (AMN-3) | Parallel synthesis method 2 | AA-3 | 1H-Indole-5-carbaldehyde | 383.2 | 0.93 |
| 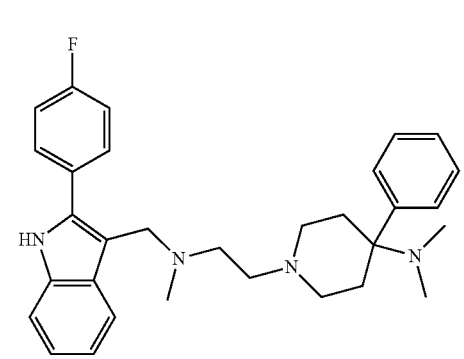 [SMILES: CN(CCN1CCC(c2ccccc2)(N(C)C)CC1)Cc1c(-c2ccc(F)cc2)[nH]c2ccccc12] | 70 (AMN-4) | Parallel synthesis method 2 | AA-1 | 2-(4-Fluorophenyl)-1H-indole-3-carbaldehyde | 485.2 | 1.14 |
| 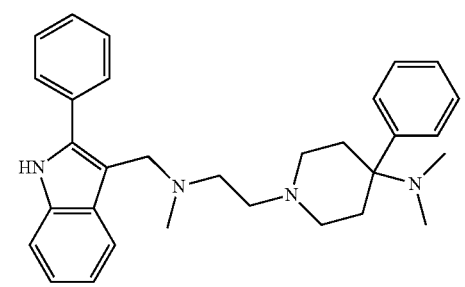 [SMILES: CN(CCN1CCC(c2ccccc2)(N(C)C)CC1)Cc1c(-c2ccccc2)[nH]c2ccccc12] | 71 (AMN-5) | Parallel synthesis method 2 | AA-1 | 2-Phenyl-1H-indole-3-carbaldehyde | 467.3 | 1.12 |

-continued

| Structure | Example (Entry No.) | Synthesis procedure | Amine structural unit | Acid/aldehyde structural unit | M+ [g/mol] | R$_t$ [min] |
|---|---|---|---|---|---|---|
| 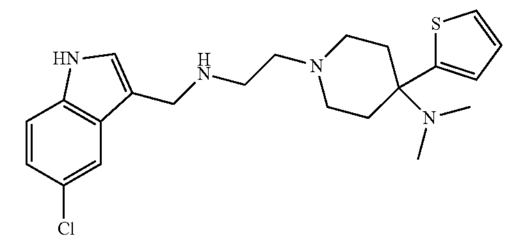 [SMILES: CN(C)C1(c2cccs2)CCN(CCNCc2c[nH]c3ccc(Cl)cc23)CC1] | 72 (AMN-6) | Parallel synthesis method 2 | AA-3 | 5-Chloro-1H-indole-3-carbaldehyde | 417.1 | 1.07 |
| 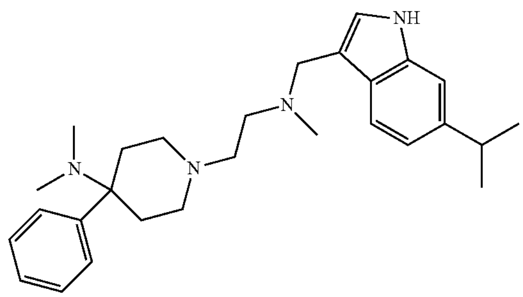 [SMILES: CC(C)c1ccc2c(CN(C)CCN3CCC(c4ccccc4)(N(C)C)CC3)c[nH]c2c1] | 73 (AMN-7) | Parallel synthesis method 2 | AA-1 | 6-Isopropyl-1H-indole-3-carbaldehyde | 433.3 | 1.15 |
| 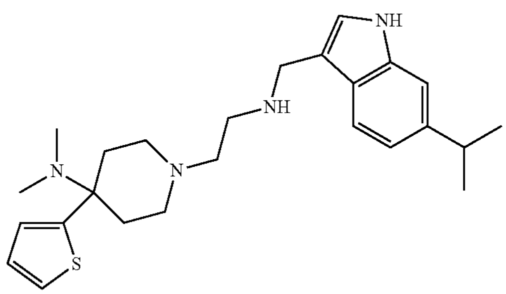 [SMILES: CC(C)c1ccc2c(CNCCN3CCC(c4cccs4)(N(C)C)CC3)c[nH]c2c1] | 74 (AMN-8) | Parallel synthesis method 2 | AA-3 | 6-Isopropyl-1H-indole-3-carbaldehyde | 425.2 | 1.14 |
| 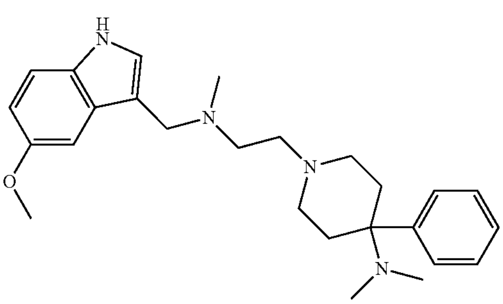 [SMILES: COc1ccc2[nH]cc(CN(C)CCN3CCC(c4ccccc4)(N(C)C)CC3)c2c1] | 75 (AMN-9) | Parallel synthesis method 2 | AA-1 | 5-Methoxy-1H-indole-3-carbaldehyde | 160.3 | 1.01 |
| 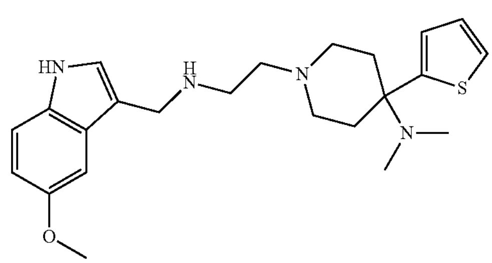 [SMILES: COc1ccc2[nH]cc(CNCCN3CCC(c4cccs4)(N(C)C)CC3)c2c1] | 76 (AMN-10) | Parallel synthesis method 2 | AA-3 | 5-Methoxy-1H-indole-3-carbaldehyde | 413.2 | 0.98 |

-continued

| Structure | Example (Entry No.) | Synthesis procedure | Amine structural unit | Acid/aldehyde structural unit | M⁺ [g/mol] | $R_t$ [min] |
|---|---|---|---|---|---|---|
| 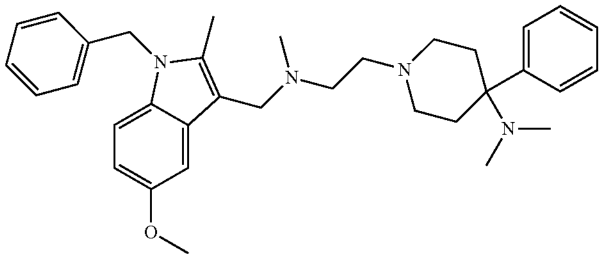 [SMILES: COc1ccc2c(c1)c(CN(C)CCN1CCC(c3ccccc3)(N(C)C)CC1)c(C)n2Cc1ccccc1] | 77 (AMN-11) | Parallel synthesis method 2 | AA-1 | 1-Benzyl-5-methoxy-2-methyl-1H-indole-3-carbaldehyde | 525.3 | 1.24 |
| 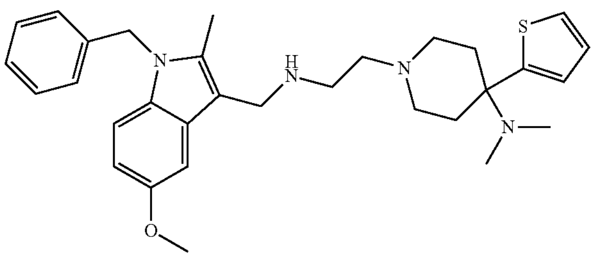 [SMILES: COc1ccc2c(c1)c(CNCCN1CCC(c3cccs3)(N(C)C)CC1)c(C)n2Cc1ccccc1] | 78 (AMN-12) | Parallel synthesis method 2 | AA-3 | 1-Benzyl-5-methoxy-2-methyl-1H-indole-3-carbaldehyde | 517.2 | 1.2 |
| 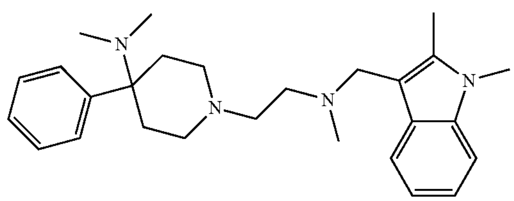 [SMILES: Cc1c(CN(C)CCN2CCC(c3ccccc3)(N(C)C)CC2)c2ccccc2n1C] | 79 (AMN-13) | Parallel synthesis method 2 | AA-1 | 1,2-Dimethyl-1H-indole-3-carbaldehyde | 419.2 | 1.08 |
| 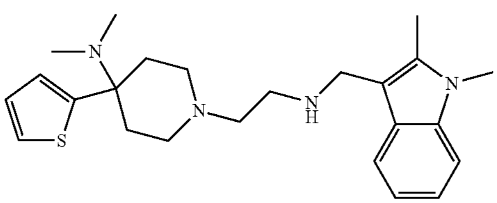 [SMILES: Cc1c(CNCCN2CCC(c3cccs3)(N(C)C)CC2)c2ccccc2n1C] | 80 (AMN-14) | Parallel synthesis method 2 | AA-3 | 1,2-Dimethyl-1H-indole-3-carbaldehyde | 411.2 | 1.03 |
| 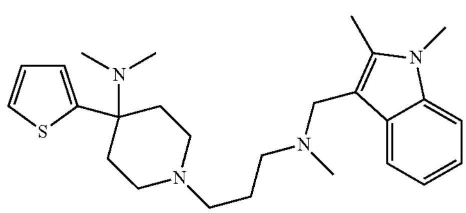 [SMILES: Cc1c(CN(C)CCCN2CCC(c3cccs3)(N(C)C)CC2)c2ccccc2n1C] | 81 (AMN-15) | Parallel synthesis method 2 | AA-6 | 1,2-Dimethyl-1H-indole-3-carbaldehyde | 439.2 | 0.92 |

In the following example, the free base of building block AA was always utilized in parallel synthesis method 2.

| Example Name | example (Entry No.) | Parallel Synthesis Method | AMN-Name | ACI_ALD-Name | M⁺ [g/mol] | $R_t$ [min] |
|---|---|---|---|---|---|---|
| N-(1-(4-(dimethylamino)-4-phenylpiperidin-1-yl)-3-methyl-1-oxobutan-2-yl)-2-(6-fluoro-1H-indol-3-yl)-N-methylacetamide | 82 (AMD-67) | no. 1 | AA-10 | ACI-8 | 493.2 | 1.58 |
| 2-(5-bromo-1H-indol-3-yl)-N-(1-(4-(dimethylamino)-4-phenylpiperidin-1-yl)-3-methyl-1-oxobutan-2-yl)-N-methylacetamide | 83 (AMD-68) | no. 1 | AA-10 | ACI-6 | 553.2 | 1.67 |

-continued

| Example Name | example (Entry No.) | Parallel Synthesis Method | AMN-Name | ACI_ALD-Name | M+ [g/mol] | Rt [min] |
|---|---|---|---|---|---|---|
| N-(3-(4-(dimethylamino)-4-phenylpiperidin-1-yl)-3-oxopropyl)-3-(1H-indol-3-yl)-4-methylpentanamide | 84 (AMD-69) | no. 1 | AA-7 | ACI-4 | 489.3 | 1.53 |
| N-(3-(4-(dimethylamino)-4-(thiophen-2-yl)piperidin-1-yl)-3-oxo-1-phenylpropyl)-3-(1H-indol-3-yl)-4-methylpentanamide | 85 (AMD-70) | no. 1 | AA-9 | ACI-4 | 571.3 | 1.68 |
| 1-(3-(4-(dimethylamino)-4-phenylpiperidine-1-carbonyl)indolin-1-yl)-2-(6-fluoro-1H-indol-3-yl)ethanone | 86 (AMD-71) | no. 1 | AA-13 | ACI-8 | 525.2 | 1.6 |
| N-(2-(4-(dimethylamino)-4-phenylpiperidin-1-yl)ethyl)-3-(1H-indol-3-yl)-N,4-dimethylpentanamide | 87 (AMD-72) | no. 1 | AA-1 | ACI-4 | 475.4 | 1.71 |
| N-(2-(4-(dimethylamino)-4-(thiophen-2-yl)piperidin-1-yl)-2-oxoethyl)-3-(1H-indol-3-yl)-4-methylpentanamide | 88 (AMD-73) | no. 1 | AA-8 | ACI-4 | 481.2 | 1.51 |
| 1-(3-(4-(dimethylamino)-4-phenylpiperidine-1-carbonyl)indolin-1-yl)-3-(1H-indol-3-yl)-4-methylpentan-1-one | 89 (AMD-74) | no. 1 | AA-13 | ACI-4 | 563.3 | 1.73 |
| N-(2-(4-(dimethylamino)-4-phenylpiperidin-1-yl)ethyl)-2-(6-fluoro-1H-indol-3-yl)-N-methylacetamide | 90 (AMD-75) | no. 1 | AA-1 | ACI-8 | 437.3 | 1.14 |
| N-(3-(4-(dimethylamino)-4-(thiophen-2-yl)piperidin-1-yl)-3-oxo-1-phenylpropyl)-3-(1H-indol-3-yl)butanamide | 91 (AMD-76) | no. 1 | AA-9 | ACI-3 | 543.2 | 1.61 |
| N-(3-(4-(dimethylamino)-4-phenylpiperidin-1-yl)-3-oxopropyl)-3-(1H-indol-3-yl)butanamide | 92 (AMD-77) | no. 1 | AA-7 | ACI-3 | 461.2 | 1.47 |
| N-(3-(4-(dimethylamino)-4-(thiophen-2-yl)piperidin-1-yl)-3-oxo-1-phenylpropyl)-2-(6-fluoro-1H-indol-3-yl)acetamide | 93 (AMD-78) | no. 1 | AA-9 | ACI-8 | 533.2 | 1.54 |
| N-(1-(4-(dimethylamino)-4-phenylpiperidin-1-yl)-3-methyl-1-oxobutan-2-yl)-3-(1H-indol-3-yl)-N-methylpropanamide | 94 (AMD-79) | no. 1 | AA-10 | ACI-5 | 489.3 | 1.62 |
| N-(2-(4-(dimethylamino)-4-(thiophen-2-yl)piperidin-1-yl)-2-oxo-1-phenylethyl)-2-(6-fluoro-1H-indol-3-yl)-N-methylacetamide | 95 (AMD-80) | no. 1 | AA-11 | ACI-8 | 533.2 | 1.62 |
| N-(3-(4-(dimethylamino)-4-(thiophen-2-yl)piperidin-1-yl)-3-oxo-1-phenylpropyl)-1H-indole-6-carboxamide | 96 (AMD-81) | no. 1 | AA-9 | ACI-13 | 501.2 | 1.52 |
| 6-chloro-N-(3-(4-(dimethylamino)-4-(thiophen-2-yl)piperidin-1-yl)-3-oxo-1-phenylpropyl)-2,3,4,9-tetrahydro-1H-carbazole-1-carboxamide | 97 (AMD-82) | no. 1 | AA-9 | ACI-7 | 589.2 | 1.79 |
| N-(3-(4-(dimethylamino)-4-phenylpiperidin-1-yl)-3-oxopropyl)-3-(1H-indol-3-yl)propanamide | 98 (AMD-83) | no. 1 | AA-7 | ACI-5 | 447.3 | 1.42 |
| N-(3-(4-(dimethylamino)-4-phenylpiperidin-1-yl)-3-oxopropyl)-1-methyl-1H-indole-6-carboxamide | 99 (AMD-84) | no. 1 | AA-7 | ACI-9 | 433.2 | 1.43 |
| 2-(5-bromo-1H-indol-3-yl)-N-(2-(4-(dimethylamino)-4-(thiophen-2-yl)piperidin-1-yl)-2-oxo-1-phenylethyl)-N-methylacetamide | 100 (AMD-85) | no. 1 | AA-11 | ACI-6 | 593.1 | 1.71 |
| N-(3-(4-(dimethylamino)-4-(thiophen-2-yl)piperidin-1-yl)-3-oxo-1-phenylpropyl)-1-methyl-1H-indole-6-carboxamide | 101 (AMD-86) | no. 1 | AA-9 | ACI-9 | 515.2 | 1.58 |
| N-(2-(4-(dimethylamino)-4-(thiophen-2-yl)piperidin-1-yl)-2-oxo-1-phenylethyl)-N-methyl-1H-indole-6-carboxamide | 102 (AMD-87) | no. 1 | AA-11 | ACI-13 | 501.2 | 1.6 |
| (6-chloro-2,3,4,9-tetrahydro-1H-carbazol-1-yl)(3-(4-(dimethylamino)-4-phenylpiperidine-1-carbonyl)piperidin-1-yl)methanone | 103 (AMD-88) | no. 1 | AA-12 | ACI-7 | 547.3 | 1.74 |

| Example Name | example (Entry No.) | Parallel Synthesis Method | AMN-Name | ACI_ALD-Name | M+ [g/mol] | R_t [min] |
|---|---|---|---|---|---|---|
| (4-(dimethylamino)-4-phenylpiperidin-1-yl)(1-(5-fluoro-1H-indole-2-carbonyl)piperidin-3-yl)methanone | 104 (AMD-89) | no. 1 | AA-12 | ACI-11 | 477.2 | 1.55 |
| N-(2-(4-(dimethylamino)-4-(thiophen-2-yl)piperidin-1-yl)-2-oxo-1-phenylethyl)-3-(1H-indol-3-yl)-N,4-dimethylpentanamide | 105 (AMD-90) | no. 1 | AA-11 | ACI-4 | 571.3 | 1.78 |
| 1-(3-(4-(dimethylamino)-4-phenylpiperidine-1-carbonyl)piperidin-1-yl)-3-(1H-indol-3-yl)-4-methylpentan-1-one | 106 (AMD-91) | no. 1 | AA-12 | ACI-4 | 529.3 | 1.6 |
| 6-chloro-N-(3-(4-(dimethylamino)-4-phenylpiperidin-1-yl)-3-oxopropyl)-2,3,4,9-tetrahydro-1H-carbazole-1-carboxamide | 107 (AMD-92) | no. 1 | AA-7 | ACI-7 | 507.2 | 1.64 |
| N-(3-(4-(dimethylamino)-4-(thiophen-2-yl)piperidin-1-yl)-3-oxo-1-phenylpropyl)-1-methyl-1H-indole-4-carboxamide | 108 (AMD-93) | no. 1 | AA-9 | ACI-10 | 515.2 | 1.56 |
| N-(2-(4-(dimethylamino)-4-(thiophen-2-yl)piperidin-1-yl)-2-oxoethyl)-1-methyl-1H-indole-6-carboxamide | 109 (AMD-94) | no. 1 | AA-8 | ACI-9 | 425.2 | 1.41 |
| N-(2-(4-(dimethylamino)-4-(thiophen-2-yl)piperidin-1-yl)-2-oxo-1-phenylethyl)-3-(1H-indol-3-yl)-N-methylpropanamide | 110 (AMD-95) | no. 1 | AA-11 | ACI-5 | 529.2 | 1.65 |
| N-(2-(4-(dimethylamino)-4-(thiophen-2-yl)piperidin-1-yl)-2-oxo-1-phenylethyl)-N,1-dimethyl-1H-indole-6-carboxamide | 111 (AMD-96) | no. 1 | AA-11 | ACI-9 | 515.2 | 1.67 |
| N-(2-(4-butyl-4-(dimethylamino)piperidin-1-yl)ethyl)-2-(6-fluoro-1H-indol-3-yl)-N-methylacetamide | 112 (AMD-97) | no. 1 | AA-4 | ACI-8 | 417.3 | 1.01 |
| N-(3-(4-(dimethylamino)-4-phenylpiperidin-1-yl)-3-oxopropyl)-1H-indole-6-carboxamide | 113 (AMD-98) | no. 1 | AA-7 | ACI-13 | 419.2 | 1.38 |
| (4-(dimethylamino)-4-phenylpiperidin-1-yl)(1-(1-methyl-1H-indole-4-carbonyl)indolin-3-yl)methanone | 114 (AMD-99) | no. 1 | AA-13 | ACI-10 | 507.3 | 1.58 |
| 2-(5-bromo-1H-indol-3-yl)-1-(3-(4-(dimethylamino)-4-phenylpiperidine-1-carbonyl)piperidin-1-yl)ethanone | (115 AMD-100) | no. 1 | AA-12 | ACI-6 | 551.1 | 1.56 |
| 6-chloro-N-(2-(4-(dimethylamino)-4-(thiophen-2-yl)piperidin-1-yl)-2-oxoethyl)-2,3,4,9-tetrahydro-1H-carbazole-1-carboxamide | 116 (AMD-101) | no. 1 | AA-8 | ACI-7 | 499.1 | 1.65 |
| N-(3-(4-(dimethylamino)-4-phenylpiperidin-1-yl)-3-oxopropyl)-3-(1-methyl-1H-indol-3-yl)propanamide | 117 (AMD-102) | no. 1 | AA-7 | ACI-2 | 461.2 | 1.48 |
| (4-(dimethylamino)-4-phenylpiperidin-1-yl)(1-(1-methyl-1H-indole-6-carbonyl)indolin-3-yl)methanone | 118 (AMD-103) | no. 1 | AA-13 | ACI-9 | 507.2 | 1.58 |
| N-(2-(4-(dimethylamino)-4-phenylpiperidin-1-yl)ethyl)-N,1-dimethyl-1H-indole-6-carboxamide | 119 (AMD-104) | no. 1 | AA-1 | ACI-9 | 419.3 | 1.19 |
| 6-(dimethylamino)-N-(3-(4-(dimethylamino)-4-phenylpiperidin-1-yl)-3-oxopropyl)-1H-indole-2-carboxamide | 120 (AMD-105) | no. 1 | AA-7 | ACI-14 | | |
| N-(3-(4-(dimethylamino)-4-phenylpiperidin-1-yl)-3-oxopropyl)-1-methyl-1H-indole-4-carboxamide | 121 (AMD-106) | no. 1 | AA-7 | ACI-10 | 433.2 | 1.41 |
| 1-(3-(4-(dimethylamino)-4-phenylpiperidine-1-carbonyl)piperidin-1-yl)-3-(1H-indol-3-yl)butan-1-one | 122 (AMD-107) | no. 1 | AA-12 | ACI-3 | 501.3 | 1.53 |
| 1-(3-(4-(dimethylamino)-4-phenylpiperidine-1-carbonyl)piperidin-1-yl)-3-(1H-indol-3-yl)propan-1-one | 123 (AMD-108) | no. 1 | AA-12 | ACI-5 | 487.2 | 1.5 |

-continued

| Example Name | example (Entry No.) | Parallel Synthesis Method | AMN-Name | ACI_ALD-Name | M+ [g/mol] | R$_t$ [min] |
|---|---|---|---|---|---|---|
| 1-(3-(4-(dimethylamino)-4-phenylpiperidine-1-carbonyl)piperidin-1-yl)-2-(6-fluoro-1H-indol-3-yl)ethanone | 124 (AMD-109) | no. 1 | AA-12 | ACI-8 | 491.2 | 1.47 |
| (1-(1H-indole-6-carbonyl)piperidin-3-yl)(4-(dimethylamino)-4-phenylpiperidin-1-yl)methanone | 125 (AMD-110) | no. 1 | AA-12 | ACI-13 | 459.2 | 1.45 |
| N-(2-(4-(dimethylamino)-4-(thiophen-2-yl)piperidin-1-yl)-2-oxo-1-phenylethyl)-N-methyl-3-(1-methyl-1H-indol-3-yl)propanamide | 126 (AMD-111) | no. 1 | AA-11 | ACI-2 | 543.2 | 1.7 |
| 6-chloro-N-(2-(4-(dimethylamino)-4-phenylpiperidin-1-yl)ethyl)-N-methyl-2,3,4,9-tetrahydro-1H-carbazole-1-carboxamide | 127 (AMD-112) | no. 1 | AA-1 | ACI-7 | 493.3 | 1.57 |
| (4-(dimethylamino)-4-phenylpiperidin-1-yl)(1-(1-methyl-1H-indole-6-carbonyl)piperidin-3-yl)methanone | 128 (AMD-113) | no. 1 | AA-12 | ACI-9 | 473.2 | 1.47 |
| N-(3-(4-(dimethylamino)-4-phenylpiperidin-1-yl)-3-oxopropyl)-5-methoxy-1H-indole-2-carboxamide | 129 (AMD-114) | no. 1 | AA-7 | ACI-12 | 449.2 | 1.45 |
| (4-(dimethylamino)-4-phenylpiperidin-1-yl)(1-(1-methyl-1H-indole-4-carbonyl)piperidin-3-yl)methanone | 130 (AMD-115) | no. 1 | AA-12 | ACI-10 | 473.3 | 1.48 |
| (1-(1H-indole-3-carbonyl)piperidin-3-yl)(4-(dimethylamino)-4-phenylpiperidin-1-yl)methanone | 131 (AMD-116) | no. 1 | AA-12 | ACI-1 | 459.2 | 1.46 |
| N-(1-(4-(dimethylamino)-4-phenylpiperidin-1-yl)-3-methyl-1-oxobutan-2-yl)-N-methyl-3-(1-methyl-1H-indol-3-yl)propanamide | 132 (AMD-117) | no. 1 | AA-10 | ACI-2 | 503.3 | 1.7 |
| 1-(3-(4-(dimethylamino)-4-phenylpiperidine-1-carbonyl)piperidin-1-yl)-3-(1-methyl-1H-indol-3-yl)propan-1-one | 133 (AMD-118) | no. 1 | AA-12 | ACI-2 | 501.3 | 1.56 |
| 6-chloro-N-(2-(4-(dimethylamino)-4-(thiophen-2-yl)piperidin-1-yl)-2-oxo-1-phenylethyl)-N-methyl-2,3,4,9-tetrahydro-1H-carbazole-1-carboxamide | 134 (AMD-119) | no. 1 | AA-11 | ACI-7 | 589.2 | 1.89 |
| N-(2-(4-(dimethylamino)-4-(thiophen-2-yl)piperidin-1-yl)-2-oxoethyl)-1-methyl-1H-indole-4-carboxamide | 135 (AMD-120) | no. 1 | AA-8 | ACI-10 | 425.3 | 1.35 |
| (6-(dimethylamino)-1H-indol-2-yl)(3-(4-(dimethylamino)-4-phenylpiperidine-1-carbonyl)piperidin-1-yl)methanone | 136 (AMD-121) | no. 1 | AA-12 | ACI-14 | 502.3 | 1.27 |
| N-((1H-indol-3-yl)methyl)-N-methyl-2-(4-phenyl-4-(pyrrolidin-1-yl)piperidin-1-yl)ethanamine | 137 (AMN-16) | no. 2 | AA-2 | ALD-2 | 417.2 | 1.22 |
| 1-(2-(((1H-indol-3-yl)methyl)(methyl)amino)ethyl)-4-butyl-N,N-dimethylpiperidin-4-amine | 138 (AMN-17) | no. 2 | AA-4 | ALD-2 | 371.3 | 1.21 |
| 3-((1H-indol-3-yl)methylamino)-1-(4-(dimethylamino)-4-phenylpiperidin-1-yl)propan-1-one | 139 (AMN-18) | no. 2 | AA-7 | ALD-2 | 405.2 | 1.44 |
| N-((1H-indol-5-yl)methyl)-N-methyl-2-(4-phenyl-4-(pyrrolidin-1-yl)piperidin-1-yl)ethanamine | 140 (AMN-19) | no. 2 | AA-2 | ALD-6 | 417.2 | 1.2 |
| 1-(2-(((1H-indol-5-yl)methyl)(methyl)amino)ethyl)-4-butyl-N,N-dimethylpiperidin-4-amine | 141 (AMN-20) | no. 2 | AA-4 | ALD-6 | 371.3 | 1.17 |
| 3-((1H-indol-5-yl)methylamino)-1-(4-(dimethylamino)-4-phenylpiperidin-1-yl)propan-1-one | 142 (AMN-21) | no. 2 | AA-7 | ALD-6 | 404.3 | 0.28 |
| N-((1H-indol-6-yl)methyl)-N-methyl-2-(4-phenyl-4-(pyrrolidin-1-yl)piperidin-1-yl)ethanamine | 143 (AMN-22) | no. 2 | AA-2 | ALD-13 | 417.2 | 1.24 |
| 1-(2-(((1H-indol-6-yl)methyl)(methyl)amino)ethyl)-4-butyl-N,N-dimethylpiperidin-4-amine | 144 (AMN-23) | no. 2 | AA-4 | ALD-13 | 371.3 | 1.23 |

| Example Name | example (Entry No.) | Parallel Synthesis Method | AMN-Name | ACI_ALD-Name | M+ [g/mol] | R$_t$ [min] |
|---|---|---|---|---|---|---|
| 3-((1H-indol-6-yl)methylamino)-1-(4-(dimethylamino)-4-phenylpiperidin-1-yl)propan-1-one | 145 (AMN-24) | no. 2 | AA-7 | ALD-13 | 405.2 | 1.23 |
| 2-(((1H-indol-5-yl)methyl)(methyl)amino)-1-(4-(dimethylamino)-4-phenylpiperidin-1-yl)-3-methylbutan-1-one | 146 (AMN-25) | no. 2 | AA-10 | ALD-6 | 447.3 | 1.23 |
| 2-(((1H-indol-5-yl)methyl)(methyl)amino)-1-(4-(dimethylamino)-4-(thiophen-2-yl)piperidin-1-yl)-2-phenylethanone | 147 (AMN-26) | no. 2 | AA-11 | ALD-6 | 487.2 | 1.3 |
| (1-((1H-indol-5-yl)methyl)piperidin-3-yl)(4-(dimethylamino)-4-phenylpiperidin-1-yl)methanone | 148 (AMN-27) | no. 2 | AA-12 | ALD-6 | 445.2 | 1.24 |
| 2-(((1H-indol-6-yl)methyl)(methyl)amino)-1-(4-(dimethylamino)-4-phenylpiperidin-1-yl)-3-methylbutan-1-one | 149 (AMN-28) | no. 2 | AA-10 | ALD-13 | 447.2 | 1.26 |
| 2-(((1H-indol-6-yl)methyl)(methyl)amino)-1-(4-(dimethylamino)-4-(thiophen-2-yl)piperidin-1-yl)-2-phenylethanone | 150 (AMN-29) | no. 2 | AA-11 | ALD-13 | 487.2 | 1.33 |
| (1-((1H-indol-3-yl)methyl)piperidin-3-yl)(4-(dimethylamino)-4-phenylpiperidin-1-yl)methanone | 151 (AMN-30) | no. 2 | AA-12 | ALD-2 | 445.2 | 1.26 |
| (1-((1H-indol-6-yl)methyl)piperidin-3-yl)(4-(dimethylamino)-4-phenylpiperidin-1-yl)methanone | 152 (AMN-31) | no. 2 | AA-12 | ALD-13 | 445.2 | 1.26 |
| N-((5-bromo-1H-indol-3-yl)methyl)-N-methyl-2-(4-phenyl-4-(pyrrolidin-1-yl)piperidin-1-yl)ethanamine | 153 (AMN-32) | no. 2 | AA-2 | ALD-1 | 495.1 | 1.36 |
| 1-(2-(((5-bromo-1H-indol-3-yl)methyl)(methyl)amino)ethyl)-4-butyl-N,N-dimethylpiperidin-4-amine | 154 (AMN-33) | no. 2 | AA-4 | ALD-1 | 449.1 | 1.34 |
| (1-((5-bromo-1H-indol-3-yl)methyl)piperidin-3-yl)(4-(dimethylamino)-4-phenylpiperidin-1-yl)methanone | 155 (AMN-34) | no. 2 | AA-12 | ALD-1 | 523.1 | 1.35 |
| (4-(dimethylamino)-4-phenylpiperidin-1-yl)(1-((2-methyl-1H-indol-3-yl)methyl)piperidin-3-yl)methanone | 156 (AMN-35) | no. 2 | AA-12 | ALD-12 | 459.2 | 1.28 |
| 1-(2-(((1H-indol-7-yl)methyl)(methyl)amino)ethyl)-4-butyl-N,N-dimethylpiperidin-4-amine | 157 (AMN-36) | no. 2 | AA-4 | ALD-14 | 371.3 | 1.24 |
| (1-((1H-indol-7-yl)methyl)piperidin-3-yl)(4-(dimethylamino)-4-phenylpiperidin-1-yl)methanone | 158 (AMN-37) | no. 2 | AA-12 | ALD-14 | 445.2 | 1.26 |
| N-((1H-indol-4-yl)methyl)-N-methyl-2-(4-phenyl-4-(pyrrolidin-1-yl)piperidin-1-yl)ethanamine | 159 (AMN-38) | no. 2 | AA-2 | ALD-15 | 417.3 | 0.28 |
| 1-(2-(((1H-indol-4-yl)methyl)(methyl)amino)ethyl)-4-butyl-N,N-dimethylpiperidin-4-amine | 160 (AMN-39) | no. 2 | AA-4 | ALD-15 | 371.3 | 1.13 |
| (1-((1H-indol-4-yl)methyl)piperidin-3-yl)(4-(dimethylamino)-4-phenylpiperidin-1-yl)methanone | 161 (AMN-40) | no. 2 | AA-12 | ALD-15 | 445.2 | 1.2 |
| 3-((5-bromo-1H-indol-3-yl)methylamino)-1-(4-(dimethylamino)-4-phenylpiperidin-1-yl)propan-1-one | 162 (AMN-41) | no. 2 | AA-7 | ALD-1 | 483.1 | 1.58 |
| 3-((5-bromo-1H-indol-3-yl)methylamino)-1-(4-(dimethylamino)-4-(thiophen-2-yl)piperidin-1-yl)-3-phenylpropan-1-one | 163 (AMN-42) | no. 2 | AA-9 | ALD-1 | 565.1 | 1.63 |
| 3-((1H-indol-3-yl)methylamino)-1-(4-(dimethylamino)-4-(thiophen-2-yl)piperidin-1-yl)-3-phenylpropan-1-one | 164 (AMN-43) | no. 2 | AA-9 | ALD-2 | 487.2 | 1.35 |
| 3-((1H-indol-5-yl)methylamino)-1-(4-(dimethylamino)-4-(thiophen-2-yl)piperidin-1-yl)-3-phenylpropan-1-one | 165 (AMN-44) | no. 2 | AA-9 | ALD-6 | 487.2 | 1.56 |

-continued

| Example Name | example (Entry No.) | Parallel Synthesis Method | AMN-Name | ACI_ALD-Name | M+ [g/mol] | R_t [min] |
|---|---|---|---|---|---|---|
| (1-((1H-indol-5-yl)methyl)indolin-3-yl)(4-(dimethylamino)-4-phenylpiperidin-1-yl)methanone | 166 (AMN-45) | no. 2 | AA-13 | ALD-6 | 479.2 | 1.67 |
| 1-(4-(dimethylamino)-4-phenylpiperidin-1-yl)-3-((2-methyl-1H-indol-3-yl)methylamino)propan-1-one | 167 (AMN-46) | no. 2 | AA-7 | ALD-12 | 419.2 | 1.49 |
| 1-(4-(dimethylamino)-4-(thiophen-2-yl)piperidin-1-yl)-3-((2-methyl-1H-indol-3-yl)methylamino)-3-phenylpropan-1-one | 168 (AMN-47) | no. 2 | AA-9 | ALD-12 | 501.2 | 1.38 |
| 3-((1H-indol-6-yl)methylamino)-1-(4-(dimethylamino)-4-(thiophen-2-yl)piperidin-1-yl)-3-phenylpropan-1-one | 169 (AMN-48) | no. 2 | AA-9 | ALD-13 | 487.2 | 1.35 |
| (1-((1H-indol-6-yl)methyl)indolin-3-yl)(4-(dimethylamino)-4-phenylpiperidin-1-yl)methanone | 170 (AMN-49) | no. 2 | AA-13 | ALD-13 | 479.2 | 1.69 |
| 3-((1H-indol-7-yl)methylamino)-1-(4-(dimethylamino)-4-phenylpiperidin-1-yl)propan-1-one | 171 (AMN-50) | no. 2 | AA-7 | ALD-14 | 405.2 | 1.24 |
| 2-((1H-indol-7-yl)methylamino)-1-(4-(dimethylamino)-4-(thiophen-2-yl)piperidin-1-yl)ethanone | 172 (AMN-51) | no. 2 | AA-8 | ALD-14 | 397.1 | 1.21 |
| 3-((1H-indol-7-yl)methylamino)-1-(4-(dimethylamino)-4-(thiophen-2-yl)piperidin-1-yl)-3-phenylpropan-1-one | 173 (AMN-52) | no. 2 | AA-9 | ALD-14 | 487.2 | 1.38 |
| 3-((1H-indol-4-yl)methylamino)-1-(4-(dimethylamino)-4-(thiophen-2-yl)piperidin-1-yl)-3-phenylpropan-1-one | 174 (AMN-53) | no. 2 | AA-9 | ALD-15 | 487.2 | 1.34 |
| (1-((1H-indol-4-yl)methyl)indolin-3-yl)(4-(dimethylamino)-4-phenylpiperidin-1-yl)methanone | 175 (AMN-54) | no. 2 | AA-13 | ALD-15 | 479.2 | 1.68 |
| (4-(dimethylamino)-4-phenylpiperidin-1-yl)(1-((6-methoxy-1,2-dimethyl-1H-indol-3-yl)methyl)piperidin-3-yl)methanone | 176 (AMN-55) | no. 2 | AA-12 | ALD-3 | 503.3 | 1.38 |
| (4-(dimethylamino)-4-phenylpiperidin-1-yl)(1-((2-(4-fluorophenyl)-1H-indol-3-yl)methyl)piperidin-3-yl)methanone | 177 (AMN-56) | no. 2 | AA-12 | ALD-7 | 539.3 | 1.4 |
| 1-(2-((5-chloro-1H-indol-3-yl)methylamino)ethyl)-N,N-dimethyl-4-(thiophen-2-yl)piperidin-4-amine | 178 (AMN-57) | no. 2 | AA-3 | ALD-10 | 417.1 | 1.06 |
| 1-(2-((1H-indol-3-yl)methylamino)ethyl)-N,N-dimethyl-4-(thiophen-2-yl)piperidin-4-amine | 179 (AMN-58) | no. 2 | AA-3 | ALD-2 | 383.2 | 1.2 |
| 1-(2-(((6-isopropyl-1H-indol-3-yl)methyl)(methyl)amino)ethyl)-N,N-dimethyl-4-phenylpiperidin-4-amine | 180 (AMN-59) | no. 2 | N AA-1 | ALD-11 | 433.3 | 1.15 |
| 1-(2-(((1H-indol-6-yl)methyl)(methyl)amino)ethyl)-N,N-dimethyl-4-phenylpiperidin-4-amine | 181 (AMN-60) | no. 2 | AA-1 | ALD-13 | 391.2 | 1 |
| 1-(2-(((5-chloro-1H-indol-3-yl)methyl)(methyl)amino)ethyl)-N,N-dimethyl-4-phenylpiperidin-4-amine | 182 (AMN-61) | no. 2 | AA-1 | ALD-10 | 425.2 | 1.09 |
| 1-(2-(((5-chloro-1H-indol-3-yl)methyl)(methyl)amino)ethyl)-N,N-dimethyl-4-phenylpiperidin-4-amine | 183 (AMN-62) | no. 2 | AA-1 | ALD-10 | 425.2 | 1.1 |
| 1-(2-(((1H-indol-6-yl)methyl)(methyl)amino)ethyl)-N,N-dimethyl-4-phenylpiperidin-4-amine | 184 (AMN-63) | no. 2 | AA-1 | ALD-13 | 391.2 | 1 |
| 1-(2-(((5-bromo-1H-indol-3-yl)methyl)(methyl)amino)ethyl)-N,N-dimethyl-4-phenylpiperidin-4-amine | 185 (AMN-64) | no. 2 | AA-1 | ALD-1 | 469.0 | 1.11 |
| 1-(2-(((1H-indol-3-yl)methyl)(methyl)amino)ethyl)-N,N-dimethyl-4-phenylpiperidin-4-amine | 186 (AMN-65) | no. 2 | AA-1 | ALD-2 | 391.2 | 0.98 |
| 1-(2-(((1H-indol-3-yl)methyl)(methyl)amino)ethyl)-N,N-dimethyl-4-phenylpiperidin-4-amine | 187 (AMN-66) | no. 2 | AA-1 | ALD-2 | 391.2 | 0.99 |

-continued

| Example Name | example (Entry No.) | Parallel Synthesis Method | AMN-Name | ACI_ALD-Name | M+ [g/mol] | R$_t$ [min] |
|---|---|---|---|---|---|---|
| 1-(2-((5-methoxy-1H-indol-3-yl)methylamino)ethyl)-N,N-dimethyl-4-(thiophen-2-yl)piperidin-4-amine | 188 (AMN-67) | no. 2 | AA-3 | ALD-8 | 413.2 | 1.16 |
| 1-(2-(((1,2-dimethyl-1H-indol-3-yl)methyl)(methyl)amino)ethyl)-N,N-dimethyl-4-phenylpiperidin-4-amine | 189 (AMN-68) | no. 2 | AA-1 | ALD-5 | 419.3 | 1.08 |
| 1-(2-(((5-methoxy-1H-indol-3-yl)methyl)(methyl)amino)ethyl)-N,N-dimethyl-4-phenylpiperidin-4-amine | 190 (AMN-69) | no. 2 | AA-1 | ALD-8 | 421.3 | 1.01 |
| 1-(2-(((5-methoxy-1H-indol-3-yl)methyl)(methyl)amino)ethyl)-N,N-dimethyl-4-phenylpiperidin-4-amine | 191 (AMN-70) | no. 2 | AA-1 | ALD-8 | 421.3 | 1 |
| 1-(2-(((5-methoxy-1H-indol-3-yl)methyl)(methyl)amino)ethyl)-N,N-dimethyl-4-phenylpiperidin-4-amine | 192 (AMN-71) | no. 2 | AA-1 | ALD-8 | 421.3 | 1.01 |
| 1-(2-(((1-benzyl-5-methoxy-2-methyl-1H-indol-3-yl)methyl)(methyl)amino)ethyl)-N,N-dimethyl-4-phenylpiperidin-4-amine | 193 (AMN-72) | no. 2 | AA-1 | ALD-4 | 525.3 | 1.22 |
| 1-(2-(((1H-indol-4-yl)methyl)(methyl)amino)ethyl)-N,N-dimethyl-4-phenylpiperidin-4-amine | 194 (AMN-73) | no. 2 | AA-1 | ALD-15 | 391.2 | 0.96 |
| 1-(2-(((1H-indol-4-yl)methyl)(methyl)amino)ethyl)-N,N-dimethyl-4-phenylpiperidin-4-amine | 195 (AMN-74) | no. 2 | AA-1 | ALD-15 | 391.2 | 0.94 |

Investigations into the effectiveness of the compounds according to the invention:

The data resulting from the following assays and models is summarised in Table 1.

Measurement of ORL1 Binding

The cyclohexane derivatives having the general formula I were investigated in a receptor binding assay with $^3$H-nociceptin/orphanin FQ with membranes of recombinant CHO—ORL1 cells. This test system was conducted in accordance with the method described by Ardati et al. (Mol. Pharmacol., 51, 1997, p. 816-824). The concentration of $^3$H-nociceptin/orphanin FQ in these tests was 0.5 nM. The binding assays were carried out with 20 μg amounts of membrane protein per 200 μl batch in 50 mM Hepes, pH 7.4, 10 mM MgCl$_2$ and 1 mM EDTA. The binding to the ORL1 receptor was determined using 1 mg amounts of WGA-SPA beads (Amersham-Pharmacia, Freiburg, Germany), by incubation of the batch for one hour at room temperature and subsequent measurement in a Trilux scintillation counter (Wallac, Finland). The affinity is given in Table 1 as the nanomolar K$_i$ value or in % inhibition at c=1 μM.

Measurement of μ Binding

The receptor affinity to the human μ-opiate receptor was determined in a homogeneous batch in microtitre plates. To this end, dilution series of the substituted indole derivative to be tested were incubated for 90 minutes at room temperature with a receptor membrane preparation (15-40 μg protein per 250 μl incubation batch) of CHO-K1 cells, which express the human μ-opiate receptor (RB—HOM receptor membrane preparation from NEN, Zaventem, Belgium), in the presence of 1 nmol/l of the radioactive ligand [$^3$H] naloxone (NET719, NEN, Zaventem, Belgium) and 1 mg of WGA-SPA beads (wheat germ agglutinin SPA beads from Amersham/Pharmacia, Freiburg, Germany) in a total volume of 250 μl. 50 mmol/l tris-HCl supplemented with 0.05 wt. % sodium azide and 0.06 wt. % bovine serum albumin were used as the incubation buffer. In order to determine the non-specific binding, 25 μmol/l of naloxone were also added. At the end of the ninety-minute incubation period the microtitre plates were centrifuged for 20 minutes at 1000 g and the radioactivity was measured in a β counter (Microbeta-Trilux, PerkinElmer Wallac, Freiburg, Germany). The percentage displacement of the radioactive ligand from its binding to the human μ-opiate receptor was determined at a test substance concentration of 1 μmol/l and stated as the percentage inhibition (% inhibition) of the specific binding. In some cases the percentage displacement due to differing concentrations of the compounds having the general formula I to be tested was used to calculate the IC$_{50}$ inhibition concentrations which bring about a 50-percent displacement of the radioactive ligand. K$_i$ values for the test substances were obtained by extrapolation using the Cheng-Prusoff equation.

| Example | % Inhibition (ORL1) at 1 μM | % Inhibition (μ) at 1 μM |
|---|---|---|
| 1 | 80 | 94 |
| 2 | 96 | 99 |
| 3 | 90 | 92 |
| 4 | 86 | 93 |
| 5 | 89 | 98 |
| 6 | 98 | 102 |
| 7 | 62 | 95 |
| 8 | 96 | 99 |
| 9 | 77 | 101 |
| 10 | 56 | 99 |
| 11 | 80 | 86 |
| 12 | 67 | 84 |
| 13 | 35 | 80 |
| 14 | 48 | 73 |
| 15 | 58 | 88 |
| 16 | 89 | 94 |
| 17 | 38 | 70 |
| 18 | 82 | 95 |
| 19 | 59 | 89 |
| 20 | 68 | 88 |
| 21 | 62 | 87 |
| 22 | 25 | 70 |
| 23 | 53 | 86 |
| 24 | 84 | 97 |
| 25 | 62 | 86 |
| 26 | 59 | 88 |

| Example | % Inhibition (ORL1) at 1 μM | % Inhibition (μ) at 1 μM |
| --- | --- | --- |
| 27 | 93 | 98 |
| 28 | 36 | 88 |
| 29 | 51 | 94 |
| 30 | 21 | 78 |
| 31 | 35 | 88 |
| 32 | — | 61 |
| 33 | 27 | 94 |
| 34 | 43 | 88 |
| 35 | 79 | 57 |
| 36 | 31 | 62 |
| 37 | 16 | 47 |
| 38 | — | 68 |
| 39 | 32 | 76 |
| 40 | — | 40 |
| 41 | 17 | 63 |
| 42 | 22 | 28 |
| 43 | 21 | 54 |
| 44 | 50 | 92 |
| 45 | 49 | 82 |
| 46 | — | 20 |
| 47 | — | 61 |
| 48 | — | 14 |
| 49 | 17 | 52 |
| 50 | 39 | 79 |
| 51 | 26 | 43 |
| 52 | 28 | 65 |
| 53 | 73 | 90 |
| 54 | — | 15 |
| 55 | — | 66 |
| 56 | 35 | 71 |
| 57 | — | 45 |
| 58 | 20 | 77 |
| 59 | 60 | 86 |
| 60 | 45 | 81 |
| 61 | 65 | 89 |
| 62 | 14 | 57 |
| 63 | 41 | 81 |
| 64 | — | 18 |
| 65 | — | 42 |
| 66 | 33 | 71 |
| 67 | 90 | 93 |
| 68 | 65 | 93 |
| 69 | 90 | 96 |
| 70 | 80 | 98 |
| 71 | 83 | 96 |
| 72 | 95 | 101 |
| 73 | 95 | 95 |
| 74 | 97 | 99 |
| 75 | 79 | 97 |
| 76 | 93 | 99 |
| 77 | 60 | 89 |
| 78 | 62 | 93 |
| 79 | 83 | 101 |
| 80 | 97 | 101 |
| 81 | 98 | 100 |
| 82 | 97 | 97 |
| 83 | 95 | 84 |
| 84 | 95 | 100 |
| 85 | 94 | 101 |
| 86 | 94 | 88 |
| 87 | 93 | 102 |
| 88 | 92 | 94 |
| 89 | 91 | 94 |
| 90 | 90 | 99 |
| 91 | 89 | 97 |
| 92 | 88 | 93 |
| 93 | 88 | 97 |
| 94 | 82 | 71 |
| 95 | 82 | 81 |
| 96 | 79 | 96 |
| 97 | 77 | 70 |
| 98 | 73 | 85 |
| 99 | 71 | 87 |
| 100 | 69 | 95 |
| 101 | 68 | 96 |
| 102 | 65 | 66 |
| 103 | 65 | 35 |
| 104 | 64 | 89 |
| 105 | 63 | 91 |
| 106 | 63 | 92 |
| 107 | 63 | 52 |
| 108 | 63 | 98 |
| 109 | 61 | 81 |
| 110 | 60 | 92 |
| 111 | 60 | 82 |
| 112 | 59 | 92 |
| 113 | 57 | 89 |
| 114 | 56 | 90 |
| 115 | 53 | 72 |
| 116 | 50 | 83 |
| 117 | 48 | 79 |
| 118 | 46 | 97 |
| 119 | 45 | 95 |
| 120 | 45 | 60 |
| 121 | 44 | 88 |
| 122 | 43 | 84 |
| 123 | 43 | 72 |
| 124 | 43 | 64 |
| 125 | 42 | 55 |
| 126 | 40 | 90 |
| 127 | 39 | 68 |
| 128 | 39 | 56 |
| 129 | 37 | 73 |
| 130 | 36 | 51 |
| 131 | 34 | 43 |
| 132 | 34 | 63 |
| 133 | 32 | 71 |
| 134 | 29 | 34 |
| 135 | 27 | 61 |
| 136 | 24 | 46 |
| 137 | — | 82 |
| 138 | 12 | 81 |
| 139 | 74 | 90 |
| 140 | 17 | 54 |
| 141 | — | 82 |
| 142 | 40 | 78 |
| 143 | 13 | 71 |
| 144 | 39 | 90 |
| 145 | 45 | 80 |
| 146 | 24 | 53 |
| 147 | 27 | 47 |
| 148 | 17 | 41 |
| 149 | 52 | 54 |
| 150 | 76 | 54 |
| 151 | 52 | 83 |
| 152 | 80 | 93 |
| 153 | — | 93 |
| 154 | 28 | 94 |
| 155 | 69 | 89 |
| 156 | 39 | 57 |
| 157 | 30 | 96 |
| 158 | 61 | 93 |
| 159 | — | 64 |
| 160 | — | 87 |
| 161 | 15 | 66 |
| 162 | 63 | 80 |
| 163 | 55 | 87 |
| 164 | 82 | 96 |
| 165 | 47 | 92 |
| 166 | 40 | 77 |
| 167 | 65 | 86 |
| 168 | 73 | 92 |
| 169 | 54 | 91 |
| 170 | 38 | 80 |
| 171 | 73 | 97 |
| 172 | 67 | 96 |
| 173 | 74 | 96 |
| 174 | 68 | 92 |
| 175 | 10 | 70 |
| 176 | 53 | 61 |
| 177 | 51 | 94 |
| 178 | 99 | 100 |

| Example | % Inhibition (ORL1) at 1 μM | % Inhibition (μ) at 1 μM |
|---------|-----|-----|
| 179 | 97 | 76 |
| 180 | 96 | 95 |
| 181 | 96 | 34 |
| 182 | 95 | 101 |
| 183 | 95 | 100 |
| 184 | 95 | 99 |
| 185 | 91 | 95 |
| 186 | 88 | 102 |
| 187 | 87 | 100 |
| 188 | 85 | 99 |
| 189 | 83 | 100 |
| 190 | 80 | 97 |
| 191 | 80 | 96 |
| 192 | 76 | 96 |
| 193 | 68 | 82 |
| 194 | 56 | 99 |
| 195 | 56 | 78 |

Parenteral Solution of a Substituted Indole Derivative According to the Invention 38 g of one of the substituted indole derivatives according to the invention, in this case example 3, are dissolved in 1 l of water for injection at room temperature and then adjusted to isotonic conditions by the addition of anhydrous glucose for injection.

The invention claimed is:

1. A substituted indole derivative compound having the formula I:

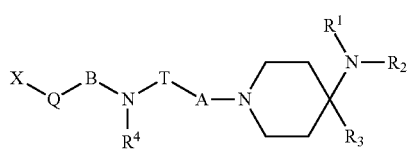

wherein
A and B independently denote $CH_2$, C=O or $SO_2$,
X stands for indolyl, which is unsubstituted or mono- or polysubstituted;
T stands for $(CR^{5a-c}R^{6a-c})_n$, where n =1, 2 or 3,
Q stands for $(CR^{7a-c}R^{8a-c})_m$, where m =0,1, 2 or 3,
$R^1$ and $R^2$ independently denote $C_{1-3}$ alkyl or H,
or $R^1$ and $R^2$ together with the N atom to which they are bonded form a ring, with $R^1$ and $R^2$ together denoting —$(CH_2)_3$— or —$(CH_2)_4$—;
$R^3$ denotes aryl or heteroaryl, each of which is optionally bound by a $C_{1-3}$ alkyl chain, each of which aryl, heteroaryl or alkyl is unsubstituted or mono- or polysubstituted; or denotes $C_{1-6}$alkyl, which is unsubstituted or mono- or polysubstituted with groups other than =O;
$R^4$ denotes H; $C_{1-6}$ alkyl, which is branched or unbranched, saturated or unsaturated, and unsubstituted or mono- or polysubstituted; or denotes aryl or heteroaryl, each of which is optionally bound by a $C_{1-3}$ alkyl chain;
$R^{5a-c}$ and $R^{6a-c}$ independently stand for H, F, CN, OH, $OCH_3$, $OCF_3$, $C_{1-6}$ alkyl, each of which alkyl is saturated or unsaturated, branched or unbranched, unsubstituted or mono- or polysubstituted; $C_{3-8}$ cycloalkyl, aryl or heteroaryl, each of which is unsubstituted or mono- or polysubstituted; or for a $C_{3-8}$ cycloalkyl, aryl or heteroaryl radical bound by a $C_{1-3}$ alkyl chain, each of which is unsubstituted or mono- or polysubstituted;
or one of the radicals $R^{5a-c}$ or $R^{6a-c}$ forms a five-, six- or seven-membered ring with the radical $R^4$ with inclusion of the nitrogen atom, which ring can itself be substituted or unsubstituted or can be fused to a further five-, six- or seven-membered ring, which can be aromatic or non-aromatic;
$R^{7a-c}R^{8a-c}$ independently stand for H; F, CN, OH, $OCH_3$, $OCF_3$, $C_{1-6}$ alkyl, each of which alkyl is saturated or unsaturated, branched or unbranched, unsubstituted or mono- or poly-substituted; $C_{3-8}$ cycloalkyl, aryl or heteroaryl, each of which is unsubstituted or mono- or polysubstituted; or for a $C_{3-8}$ cycloalkyl, aryl or heteroaryl radical bound by a $C_{1-3}$ alkyl chain, each of which is unsubstituted or mono- or polysubstituted;
or one of the radicals $R^{7a-c}$ or $R^{8a-c}$ forms a five-, six- or seven-membered unsaturated ring with a substituent in the 2 or 3 position of the indolyl ring X,
with the proviso that compounds in which $R^3$ stands for a phenyl radical which is substituted in the 3 position with OH or $OCOC_{1-8}$ alkyl are excluded from protection,
said compound optionally being in the form of a racemic mixture, or in the form of individual enantiomers or diastereomers, or in the form of mixtures of enantiomers and/or diastereomers in any mixing ratio;
or a base and/or salt of said compound or one of said forms with a physiologically compatible acid or cation.

2. Substituted indole derivative according to claim 1, wherein
substituents on alkyl and/or cycloalkyl are one or more members independently selected from the group consisting of F, Cl, Br, I, —CN, $NH_2$, NH—$C_{1-6}$ alkyl, NH—$C_{1-6}$ alkyl-OH, $C_{1-6}$ alkyl, $N(C_{1-6}$ alkyl$)_2$, $N(C_{1-6}$ alkyl-OH$)_2$, $NO_2$, SH, S—$C_{1-6}$ alkyl, S-benzyl, O—$C_{1-6}$ alkyl, OH, O—$C_{1-6}$ alkyl-OH, O-benzyl, C(=O)$C_{1-6}$ alkyl, C(=O)O$C_{1-6}$ alkyl, phenyl and benzyl,
and substituents on aryl, indolyl and/or heteroaryl are one or more members independently selected from the group consisting of F, Cl, Br, I, CN, $NH_2$, NH—$C_{1-6}$ alkyl, NH—$C_{1-6}$ alkyl-OH, $N(C_{1-6}$ alkyl$)_2$, $N(C_{1-6}$ alkyl-OH$)_2$, $NO_2$, SH, S—$C_{1-6}$ alkyl, OH, O—$C_{1-6}$ alkyl, O—$C_{1-6}$ alkyl-OH, C(=O)-aryl; C(=O)$C_{1-6}$ alkyl, C(=O)NH$C_{1-6}$ alkyl; C(=O)—N-morpholine; C(=O)-piperidine; (C=O)-pyrrolidine; (C=O)-piperazine; $NHSO_2C_{1-6}$ alkyl, NHCO$C_{1-6}$ alkyl, $CO_2H$, $CH_2SO_2$ phenyl, $CO_2$—$C_{1-6}$ alkyl, $OCF_3$, $CF_3$,

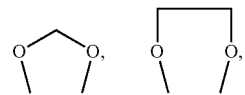

$C_{1-6}$ alkyl, pyrrolidinyl, piperidinyl, morpholinyl, benzyloxy, phenoxy, phenyl, pyridyl, alkylaryl, thienyl and furyl, wherein aryl and heteroaryl substituents can themselves be substituted with F, Cl, Br, I, CN, $CH_3$, $C_2H_5$, $NH_2$, $NO_2$, SH, $CF_3$, OH, $OCH_3$, $OC_2H_5$ or $N(CH_3)_2$.

3. Substituted indole derivative according to claim 1, wherein A denotes $CH_2$ and B denotes $CH_2$ or C=O.

4. Substituted indole derivative according to claim 1, wherein X stands for indolyl, which is unsubstituted or mono- or polysubstituted with one or more substituents independently selected from the group consisting of F, Cl, Br, I, CN, $CH_3$, $C_2H_5$, $C_3H_8$, $NH_2$, $NO_2$, SH, $CF_3$, OH, $OCH_3$, $OC_2H_5$, $N(CH_3)_2$ and phenyl, which phenyl is itself unsubstituted or mono- or polysubstituted with one or more substituents independently selected from the group consisting of F, Cl, Br, I, CN, CH₃, C₂H₅, NH₂, NO₂, SH, CF₃, OH, OCH₃, OC₂H₅ and N(CH₃)₂.

5. Substituted indole derivative according to claim 1, wherein R¹ and R² independently denote methyl or H.

6. Substituted indole derivative according to claim 1, wherein

R³ stands for phenyl, benzyl, phenethyl, thienyl, pyridyl, thiazolyl, imidazolyl, 1,2,4-triazolyl, benzimidazolyl or benzyl, each of which is unsubstituted or mono- or polysubstituted with one or more substituents independently selected from the group consisting of F, Cl, Br, CN, CH₃, C₂H₅, NH₂, NO₂, SH, CF₃, OH, OCH₃, OC₂H₅ or N(CH₃)₂; and ethyl, n-propyl, 2-propyl, allyl, n-butyl, isobutyl, sec-butyl, tert-butyl, n-pentyl, isopentyl, neopentyl, n-hexyl, cyclopentyl or cyclohexyl, each of which is unsubstituted or mono- or polysubstituted with one or more substituents independently selected from the group consisting of OH, OCH₃ and OC₂H₅.

7. Substituted indole derivative according to claim 1, wherein

R⁴ denotes H, CH₃ or benzyl.

8. Substituted indole derivative according to claim 1, wherein

R⁵ᵃ⁻ᶜ and R⁶ᵃ⁻ᶜ stand for H.

9. Substituted indole derivatives according to claim 1, wherein

R⁷ᵃ⁻ᶜR⁸ᵃ⁻ᶜ independently denote H; C₁₋₆ alkyl, which is saturated or unsaturated, branched or unbranched, or one of the radicals R⁷ᵃ⁻ᶜ or R⁸ᵃ⁻ᶜ forms a five-, six- or seven-membered unsaturated ring with a substituent in the 3 position of the indolyl ring X, such that a structural element having the formulae IIa-f is produced:

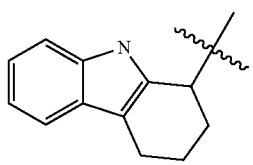
IIa

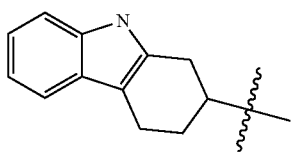
IIb

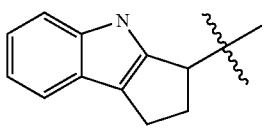
IIc

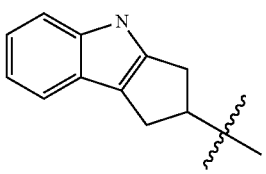
IId

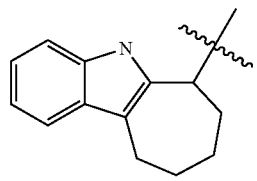
IIe

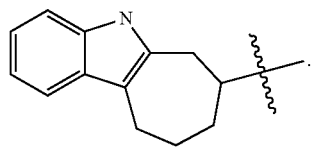
IIf

10. Substituted indole derivative according to claim 1, which is selected from the group consisting of:

1  N-(2-(4-(Dimethylamino)-4-phenylpiperidin-1-yl)ethyl)-N-methyl-1H-indol-6-carboxamide;
2  N-(2-(4-(Dimethylamino)-4-(thiophen-2-yl)piperidin-1-yl)ethyl)-3-(1H-indol-3-yl)-4-methylpentanamide;
3  N-(2-(4-(Dimethylamino)-4-phenylpiperidin-1-yl)ethyl)-5-fluoro-N-methyl-1H-indole-2-carboxamide;
4  N-(2-(4-(Dimethylamino)-4-phenylpiperidin-1-yl)ethyl)-3-(1H-indol-3-yl)-N-methylpropanamide;
5  N-(2-(4-(Dimethylamino)-4-(thiophen-2-yl)piperidin-1-yl)ethyl)-3-(1H-indol-3-yl)propanamide;
6  N-(2-(4-(Dimethylamino)-4-(thiophen-2-yl)piperidin-1-yl)ethyl)-3-(1H-indol-3-yl)-4-methylpentanamide;
7  6-Chloro-N-(2-(4-(dimethylamino)-4-(thiophen-2-yl)piperidin-1-yl)ethyl)-2,3,4,9-tetrahydro-1H-carbazole-1-carboxamide;
8  N-(2-(4-(Dimethylamino)-4-(thiophen-2-yl)piperidin-1-yl)ethyl)-2-(6-fluoro-1H-indol-3-yl)acetamide;
9  N-(2-(4-(Dimethylamino)-4-(thiophen-2-yl)piperidin-1-yl)ethyl)-1-methyl-1H-indol-6-carboxamide;
10 N-(2-(4-(Dimethylamino)-4-(thiophen-2-yl)piperidin-1-yl)ethyl)-1-methyl-1H-indol-4-carboxamide;
11 N-(3-(4-(Dimethylamino)-4-(thiophen-2-yl)piperidin-1-yl)propyl)-N-methyl-1H-indol-3-carboxamide;
12 N-(2-(4-(Dimethylamino)-4-phenylpiperidin-1-yl)ethyl)-N-methyl-1H-indol-3-carboxamide;
13 N-(3-(4-(Dimethylamino)-4-(thiophen-2-yl)piperidin-1-yl)propyl)-N-methyl-3-(1-methyl-1H-indol-3-yl)propanamide;
14 N-(2-(4-(Dimethylamino)-4-phenylpiperidin-1-yl)ethyl)-N-methyl-3-(1-methyl-1H-indol-3-yl)propanamide;
15 N-(3-(4-(Dimethylamino)-4-(thiophen-2-yl)piperidin-1-yl)propyl)-5-fluoro-N-methyl-1H-indole-2-carboxamide;
16 N-(2-(4-(Dimethylamino)-4-phenylpiperidin-1-yl)ethyl)-5-fluoro-N-methyl-1H-indole-2-carboxamide;
17 N-(3-(4-(Dimethylamino)-4-(thiophen-2-yl)piperidin-1-yl)propyl)-N-methyl-1H-indol-6-carboxamide;
18 N-(2-(4-(Dimethylamino)-4-phenylpiperidin-1-yl)ethyl)-N-methyl-1H-indol-6-carboxamide;
19 N-(3-(4-(Dimethylamino)-4-(thiophen-2-yl)piperidin-1-yl)propyl)-3-(1H-indol-3-yl)-N-methylbutanamide;
20 N-(2-(4-(Dimethylamino)-4-phenylpiperidin-1-yl)ethyl)-3-(1H-indol-3-yl)-N-methylbutanamide;

21 N-(3-(4-(Dimethylamino)-4-(thiophen-2-yl)piperidin-1-yl)propyl)-3-(1H-indol-3-yl)-N-methylpropanamide;
22 N-(3-(4-(Dimethylamino)-4-(thiophen-2-yl)piperidin-1-yl)propyl)-5-methoxy-N-methyl-1H-indol-2-carboxamide;
23 N-(3-(4-(Dimethylamino)-4-(thiophen-2-yl)piperidin-1-yl)propyl)-3-(1H-indol-3-yl)-N,4-dimethylpentanamide;
24 N-(2-(4-(Dimethylamino)-4-phenylpiperidin-1-yl)ethyl)-3-(1H-indol-3-yl)-N,4-dimethylpentanamide;
25 6-Cloro-N-(2-(4-(Dimethylamino)-4-phenylpiperidin-1-yl)ethyl)-N-methyl-2,3,4,9-tetrahydro-1H-carbazole-1-carboxamide;
26 N-(3-(4-(Dimethylamino)-4-(thiophen-2-yl)piperidin-1-yl)propyl)-2-(6-fluoro-1H-indol-3-yl)-N-methylacetamide;
27 N-(2-(4-(Dimethylamino)-4-phenylpiperidin-1-yl)ethyl)-2-(6-fluoro-1H-indol-3-yl)-N-methylacetamide;
28 N-(3-(4-(Dimethylamino)-4-(thiophen-2-yl)piperidin-1-yl)propyl)-N,1-dimethyl-1H-indole-6-carboxamide;
29 N-(2-(4-(Dimethylamino)-4-phenylpiperidin-1-yl)ethyl)-N,1-dimethyl-1H-indol-6-carboxamide;
30 N-(3-(4-(Dimethylamino)-4-(thiophen-2-yl)piperidin-1-yl)propyl)-N,1-dimethyl-1H-indole-4-carboxamide;
31 N-(2-(4-(Dimethylamino)-4-phenylpiperidin-1-yl)ethyl)-N,1-dimethyl-1H-indol-4-carboxamide;
32 3-(1H-Indol-3-yl)-N,4-dimethyl-N-(2-(4-phenyl-4-(pyrrolidin-1-yl)piperidin-1-yl)ethyl)pentanamide;
33 N-(2-(4-Butyl-4-(dimethylamino)piperidin-1-yl)ethyl)-3-(1H-indol-3-yl)-N,4-dimethylpentanamide;
34 N-(3-(4-(Dimethylamino)-4-phenylpiperidin-1-yl)propyl)-3-(1H-indol-3-yl)-N,4-dimethylpentanamide;
35 6-Chloro-N-(3-(4-(Dimethylamino)-4-phenylpiperidin-1-yl)propyl)-N-methyl-2,3,4,9-tetrahydro-1H-carbazole-1-carboxamide;
36 2-(6-Fluoro-1H-indol-3-yl)-N-methyl-N-(2-(4-phenyl-4-(pyrrolidin-1-yl)piperidin-1-yl)ethyl)acetamide;
37 N,1-Dimethyl-N-(2-(4-phenyl-4-(pyrrolidin-1-yl)piperidin-1-yl)ethyl)-1H-indol-6-carboxamide;
38 N-(2-(4-Butyl-4-(dimethylamino)piperidin-1-yl)ethyl)-N,1-dimethyl-1H-indol-6-carboxamide;
39 N-(3-(4-(Dimethylamino)-4-phenylpiperidin-1-yl)propyl)-N,1-dimethyl-1H-indol-6-carboxamide;
40 N,1-Dimethyl-N-(2-(4-phenyl-4-(pyrrolidin-1-yl)piperidin-1-yl)ethyl)-1H-indol-4-carboxamide;
41 N-(2-(4-Butyl-4-(dimethylamino)piperidin-1-yl)ethyl)-N,1-dimethyl-1H-indol-4-carboxamide;
42 6-Chloro-N-methyl-N-(2-(4-phenyl-4-(pyrrolidin-1-yl)piperidin-1-yl)ethyl)-2,3,4,9-tetrahydro-1H-carbazole-1-carboxamide;
43 N-(2-(4-Butyl-4-(dimethylamino)piperidin-1-yl)ethyl)-6-chloro-N-methyl-2,3,4,9-tetrahydro-1H-carbazole-1-carboxamide;
44 N-(2-(4-Butyl-4-(dimethylamino)piperidin-1-yl)ethyl)-2-(6-fluoro-1H-indol-3-yl)-N-methylacetamide;
45 N-(3-(4-(Dimethylamino)-4-phenylpiperidin-1-yl)propyl)-2-(6-fluoro-1H-indol-3-yl)-N-methylacetamide;
46 N-Methyl-N-(2-(4-phenyl-4-(pyrrolidin-1-yl)piperidin-1-yl)ethyl)-1H-indol-3-carboxamide;
47 N-(2-(4-Butyl-4-(dimethylamino)piperidin-1-yl)ethyl)-N-methyl-1H-indol-3-carboxamide;
48 N-Methyl-3-(1-methyl-1H-indol-3-yl)-N-(2-(4-phenyl-4-(pyrrolidin-1-yl)piperidin-1-yl)ethyl)propanamide;
49 N-(2-(4-Butyl-4-(dimethylamino)piperidin-1-yl)ethyl)-N-methyl-3-(1-methyl-1H-indol-3-yl)propanamide;
50 N-(3-(4-(Dimethylamino)-4-phenylpiperidin-1-yl)propyl)-N-methyl-3-(1-methyl-1H-indol-3-yl)propanamide;
51 5-Fluoro-N-methyl-N-(2-(4-phenyl-4-(pyrrolidin-1-yl)piperidin-1-yl)ethyl)-1H-indole-2-carboxamide;
52 N-(2-(4-Butyl-4-(dimethylamino)piperidin-1-yl)ethyl)-5-fluoro-N-methyl-1H-indole-2-carboxamide;
53 N-(3-(4-(Dimethylamino)-4-phenylpiperidin-1-yl)propyl)-5-fluoro-N-methyl-1H-indole-2-carboxamide;
54 N-Methyl-N-(2-(4-phenyl-4-(pyrrolidin-1-yl)piperidin-1-yl)ethyl)-1H-indole-6-carboxamide;
55 N-(2-(4-Butyl-4-(dimethylamino)piperidin-1-yl)ethyl)-N-methyl-1H-indole-6-carboxamide;
56 N-(3-(4-(Dimethylamino)-4-phenylpiperidin-1-yl)propyl)-N-methyl-1H-indole-6-carboxamide;
57 3-(1H-Indol-3-yl)-N-methyl-N-(2-(4-phenyl-4-(pyrrolidin-1-yl)piperidin-1-yl)ethyl)butanamide;
58 N-(2-(4-Butyl-4-(dimethylamino)piperidin-1-yl)ethyl)-3-(1H-indol-3-yl)-N-methylbutanamide;
59 N-(3-(4-(Dimethylamino)-4-phenylpiperidin-1-yl)propyl)-3-(1H-indol-3-yl)-N-methylbutanamide;
60 N-(2-(4-Butyl-4-(dimethylamino)piperidin-1-yl)ethyl)-3-(1H-indol-3-yl)-N-methylpropanamide;
61 N-(3-(4-(Dimethylamino)-4-phenylpiperidin-1-yl)propyl)-3-(1H-indol-3-yl)-N-methylpropanamide;
62 2-(5-Bromo-1H-indol-3-yl)-N-methyl-N-(2-(4-phenyl-4-(pyrrolidin-1-yl)piperidin-1-yl)ethyl)acetamide;
63 2-(5-Bromo-1H-indol-3-yl)-N-(3-(4-(dimethylamino)-4-phenylpiperidin-1-yl)propyl)-N-methylacetamide;
64 5-Methoxy-N-methyl-N-(2-(4-phenyl-4-(pyrrolidin-1-yl)piperidin-1-yl)ethyl)-1H-indole-2-carboxamide;
65 N-(2-(4-Butyl-4-(dimethylamino)piperidin-1-yl)ethyl)-5-methoxy-N-methyl-1H-indole-2-carboxamide;
66 N-(3-(4-(Dimethylamino)-4-phenylpiperidin-1-yl)propyl)-5-methoxy-N-methyl-1H-indole-2-carboxamide;
67 1-(3-(((6-Isopropyl-1 H-indol-3-yl)methyl)(methyl)amino)propyl)-N,N-dimethyl-4-(thiophen-2-yl)piperidin-4-amine;
68 1-(2-(((1H-Indol-5-yl)methyl)(methyl)amino)ethyl)-N,N-dimethyl-4-phenylpiperidin-4-amine;
69 1-(2 -(((1H-Indol-5-yl)methyl)amino)ethyl)-N,N-dimethyl-4-(thiophen-2-yl)piperidin-4-amine;
70 1-(2 -(((2-(4-Fluorophenyl)-1H-indol-3-yl)methyl)(methyl)amino)ethyl)-N,N-dimethyl-4-phenylpiperidin-4-amine;
71 N,N-Dimethyl-1-(2-(methyl((2-phenyl-1H-indol-3-yl)methyl)amino)ethyl)-4-phenylpiperidin-4-amine;
72 1-(2-(((5-Chloro -1H-indol-3-yl)methyl)amino)ethyl)-N,N-dimethyl-4-(thiophen-2-yl)piperidin-4 -amine;
73 1-(2-(((6-Isopropyl-1 H-indol-3-yl)methyl)(methyl)amino)ethyl)-N,N-dimethyl-4-phenylpiperidin-4-amine;

74 1-(2-(((6-Isopropyl-1H-indol-3-yl)methyl)amino) ethyl)-N,N-dimethyl-4-(thiophen-2-yl)piperidin-4-amine;

75 1-(2-(((5-Methoxy-1H-indol-3-yl)methyl)(methyl) amino)ethyl)-N,N-dimethyl-4-phenylpiperidin-4-amine;

76 1-(2-(((5-Methoxy-1H-indol-3-yl)methyl)amino) ethyl)-N,N-dimethyl-4-(thiophen-2-yl)piperidin-4-amine;

77 1-(2-(((1-Benzyl-5-methoxy-2-methyl-1H-indol-3-yl) methyl)(methyl)amino)ethyl)-N,N-dimethyl-4-phenylpiperidin-4-amine;

78 1-(2-(((1-Benzyl-5-methoxy-2-methyl-1H-indol-3-yl) methyl)amino)ethyl)-N,N-dimethyl-4-(thiophen-2-yl) piperidin-4-amine;

79 1-(2-(((1,2-Dimethyl-1H-indol-3-yl)methyl)(methyl) amino)ethyl)-N,N-dimethyl-4-phenylpiperidin-4-amine;

80 1-(2-(((1,2-Dimethyl-1H-indol-3-yl)methyl)amino) ethyl)-N,N-dimethyl-4-(thiophen-2-yl)piperidin-4-amine;

81 1-(3-(((1,2-Dimethyl-1H-indol-3-yl)methyl)(methyl) amino)propyl)-N,N-dimethyl-4-(thiophen-2-yl)piperidin-4-amine;

82 N-(1-(4-(dimethylamino)-4-phenylpiperidin-1-yl)-3-methyl-1-oxobutan-2-yl)-2-(6-fluoro-1H-indol-3-yl)-N-methylacetamide;

83 2-(5-bromo-1H-indol-3-yl)-N-(1-(4-(dimethylamino)-4-phenylpiperidin-1-yl)-3-methyl-1-oxobutan-2-yl)-N-methylacetamide;

84 N-(3-(4-(dimethylamino)-4-phenylpiperidin-1-yl)-3-oxopropyl)-3-(1H-indol-3-yl)-4-methylpentanamide;

85 N-(3-(4-(dimethylamino)-4-(thiophen-2-yl)piperidin-1-yl)-3-oxo-1-phenylpropyl)-3-(1H-indol-3-yl)-4-methylpentanamide;

86 1-(3-(4-(dimethylamino)-4-phenylpiperidine-1-carbonyl)indolin-1-yl)-2-(6-fluoro-1H-indol-3-yl)ethanone;

87 N-(2-(4-(dimethylamino)-4-phenylpiperidin-1-yl) ethyl)-3-(1H-indol-3-yl)-N,4-dimethylpentanamide;

88 N-(2-(4-(dimethylamino)-4-(thiophen-2-yl)piperidin-1-yl)-2-oxoethyl)-3-(1H-indol-3-yl)-4-methylpentanamide;

89 1-(3-(4-(dimethylamino)-4-phenylpiperidine-1-carbonyl)indolin-1-yl)-3-(1H-indol-3-yl)-4-methylpentan-1-one;

90 N-(2-(4-(dimethylamino)-4-phenylpiperidin-1-yl) ethyl)-2-(6-fluoro-1H-indol-3-yl)-N-methylacetamide;

91 N-(3-(4-(dimethylamino)-4-(thiophen-2-yl)piperidin-1-yl)-3-oxo-1-phenylpropyl)-3-(1H-indol-3-yl)butanamide;

92 N-(3-(4-(dimethylamino)-4-phenylpiperidin-1-yl)-3-oxopropyl)-3-(1H-indol-3-yl)butanamide;

93 N-(3-(4-(dimethylamino)-4-(thiophen-2-yl)piperidin-1-yl)-3-oxo-1-phenylpropyl)-2-(6-fluoro-1H-indol-3-yl)acetamide;

94 N-(1-(4-(dimethylamino)-4-phenylpiperidin-1-yl)-3-methyl-1-oxobutan-2-yl)-3-(1H-indol-3-yl)-N-methylpropanamide;

95 N-(2-(4-(dimethylamino)-4-(thiophen-2-yl)piperidin-1-yl)-2-oxo-1-phenylethyl)-2-(6-fluoro-1H-indol-3-yl)-N-methylacetamide;

96 N-(3-(4-(dimethylamino)-4-(thiophen-2-yl)piperidin-1-yl)-3-oxo-1-phenylpropyl)-1H-indole-6-carboxamide;

97 6-chloro-N-(3-(4-(dimethylamino)-4-(thiophen-2-yl) piperidin-1-yl)-3-oxo-1-phenylpropyl)-2,3,4,9-tetrahydro-1H-carbazole-1-carboxamide;

98 N-(3-(4-(dimethylamino)-4-phenylpiperidin-1-yl)-3-oxopropyl)-3-(1H-indol-3-yl)propanamide;

99 N-(3-(4-(dimethylamino)-4-phenylpiperidin-1-yl)-3-oxopropyl)-1-methyl-1H-indol-6-carboxamide;

100 2-(5-bromo-1H-indol-3-yl)-N-(2-(4-(dimethylamino)-4-(thiophen-2-yl)piperidin-1-yl)-2-oxo-1-phenylethyl)-N-methylacetamide;

101 N-(3-(4-(dimethylamino)-4-(thiophen-2-yl)piperidin-1-yl)-3-oxo-1-phenylpropyl)-1-methyl-1H-indole-6-carboxamide;

102 N-(2-(4-(dimethylamino)-4-(thiophen-2-yl)piperidin-1-yl)-2-oxo-1-phenylethyl)-N-methyl-1H-indole-6-carboxamide;

103 (6-chloro-2,3,4,9-tetrahydro-1H-carbazol-1-yl)(3-(4-(dimethylamino)-4-phenylpiperidine-1-carbonyl)piperidin-1-yl)methanone;

104 (4-(dimethylamino)-4-phenylpiperidin-1-yl)(1-(5-fluoro-1H-indole-2-carbonyl)piperidin-3-yl)methanone;

105 N-(2-(4-(dimethylamino)-4-(thiophen-2-yl)piperidin-1-yl)-2-oxo-1-phenylethyl)-3-(1H-indol-3-yl)-N,4-dimethylpentanamide;

106 1-(3-(4-(dimethylamino)-4-phenylpiperidine-1-carbonyl)piperidin-1-yl)-3-(1H-indol-3-yl)-4-methylpentan-1-one;

107 6-chloro-N-(3-(4-(dimethylamino)-4-phenylpiperidin-1-yl)-3-oxopropyl)-2,3,4,9-tetrahydro-1H-carbazole-1-carboxamide;

108 N-(3-(4-(dimethylamino)-4-(thiophen-2-yl)piperidin-1-yl)-3-oxo-1-phenylpropyl)-1-methyl-1H-indole-4-carboxamide;

109 N-(2-(4-(dimethylamino)-4-(thiophen-2-yl)piperidin-1-yl)-2-oxoethyl)-1-methyl-1H-indole-6-carboxamide;

110 N-(2-(4-(dimethylamino)-4-(thiophen-2-yl)piperidin-1-yl)-2-oxo-1-phenylethyl)-3-(1H-indol-3-yl)-N-methylpropanamide;

111 N-(2-(4-(dimethylamino)-4-(thiophen-2-yl)piperidin-1-yl)-2-oxo-1-phenylethyl)-N,1-dimethyl-1H-indol-6-carboxamide;

112 N-(2-(4-butyl-4-(dimethylamino)piperidin-1-yl) ethyl)-2-(6-fluoro-1H-indol-3-yl)-N-methylacetamide;

113 N-(3-(4-(dimethylamino)-4-phenylpiperidin-1-yl)-3-oxopropyl)-1H-indole-6-carboxamide;

114 (4-(dimethylamino)-4-phenylpiperidin-1-yl)(1-(1-methyl-1H-indole-4-carbonyl)indolin-3-yl)methanone;

115 2-(5-bromo-1H-indol-3-yl)-1-(3-(4-(dimethylamino)-4-phenylpiperidine-1-carbonyl)piperidin-1-yl) ethanone;

116 6-chloro-N-(2-(4-(dimethylamino)-4-(thiophen-2-yl) piperidin-1-yl)-2-oxoethyl)-2,3,4,9-tetrahydro-1H-carbazole-1-carboxamide;

117 N-(3-(4-(dimethylamino)-4-phenylpiperidin-1-yl)-3-oxopropyl)-3-(1-methyl-1H-indol-3-yl)propanamide;

118 (4-(dimethylamino)-4-phenylpiperidin-1-yl)(1-(1-methyl-1H-indole-6-carbonyl)indolin-3-yl)methanone;

119 N-(2-(4-(dimethylamino)-4-phenylpiperidin-1-yl) ethyl)-N,1-dimethyl-1H-indole-6-carboxamide;
120 6-(dimethylamino)-N-(3-(4-(dimethylamino)-4-phenylpiperidin-1-yl)-3-oxopropyl)-1H-indole-2-carboxamide;
121 N-(3-(4-(dimethylamino)-4-phenylpiperidin-1-yl)-3-oxopropyl)-1-methyl-1H-indol-4-carboxamide;
122 1-(3-(4-(dimethylamino)-4-phenylpiperidine-1-carbonyl)piperidin-1-yl)-3-(1H-indol-3-yl)butan-1-one;
123 1-(3-(4-(dimethylamino)-4-phenylpiperidine-1-carbonyl)piperidin-1-yl)-3-(1H-indol-3-yl)propan-1-one;
124 1-(3-(4-(dimethylamino)-4-phenylpiperidine-1-carbonyl)piperidin-1-yl)-2-(6-fluoro-1H-indol-3-yl)ethanone;
125 (1-(1H-indole-6-carbonyl)piperidin-3-yl)(4-(dimethylamino)-4-phenylpiperidin-1-yl)methanone;
126 N-(2-(4-(dimethylamino)-4-(thiophen-2-yl)piperidin-1-yl)-2-oxo-1-phenylethyl)-N-methyl-3-(1-methyl-1H-indol-3-yl)propanamide;
127 6-chloro-N-(2-(4-(dimethylamino)-4-phenylpiperidin-1-yl)ethyl)-N-methyl-2,3,4,9-tetrahydro-1H-carbazole-1-carboxamide;
128 (4-(dimethylamino)-4-phenylpiperidin-1-yl)(1-(1-methyl-1H-indole-6-carbonyl)piperidin-3-yl)methanone;
129 N-(3-(4-(dimethylamino)-4-phenylpiperidin-1-yl)-3-oxopropyl)-5-methoxy-1H-indole-2-carboxamide;
130 (4-(dimethylamino)-4-phenylpiperidin-1-yl)(1-(1-methyl-1H-indole-4-carbonyl)piperidin-3-yl)methanone;
131 (1-(1H-indole-3-carbonyl)piperidin-3-yl)(4-(dimethylamino)-4-phenylpiperidin-1-yl)methanone;
132 N-(1-(4-(dimethylamino)-4-phenylpiperidin-1-yl)-3-methyl-1-oxobutan-2-yl)-N-methyl-3-(1-methyl-1H-indol-3-yl)propanamide;
133 1-(3-(4-(dimethylamino)-4-phenylpiperidine-1-carbonyl)piperidin-1-yl)-3-(1-methyl-1H-indol-3-yl)propan-1-one;
134 6-chloro-N-(2-(4-(dimethylamino)-4-(thiophen-2-yl)piperidin-1-yl)-2-oxo-1-phenylethyl)-N-methyl-2,3,4,9-tetrahydro-1H-carbazole-1-carboxamide;
135 N-(2-(4-(dimethylamino)-4-(thiophen-2-yl)piperidin-1-yl)-2-oxoethyl)-1-methyl-1H-indole-4-carboxamide;
136 (6-(dimethylamino)-1H-indol-2-yl)(3-(4-(dimethylamino)-4-phenylpiperidine-1-carbonyl)piperidin-1-yl)methanone;
137 N-((1H-indol-3-yl)methyl)-N-methyl-2-(4-phenyl-4-(pyrrolidin-1-yl)piperidin-1-yl)ethanamine;
138 1-(2-(((1H-indol-3-yl)methyl)(methyl)amino)ethyl)-4-butyl-N,N-dimethylpiperidin-4-amine;
139 3-(((1H-indol-3-yl)methyl)amino)-1-(4-(dimethylamino)-4-phenylpiperidin-1-yl)propan-1-one;
140 N-((1H-indol-5-yl)methyl)-N-methyl-2-(4-phenyl-4-(pyrrolidin-1-yl)piperidin-1-yl)ethanamine;
141 1-(2-(((1H-indol-5-yl)methyl)(methyl)amino)ethyl)-4-butyl-N,N-dimethylpiperidin-4-amine;
142 3-(((1H-indol-5-yl)methyl)amino)-1-(4-(dimethylamino)-4-phenylpiperidin-1-yl)propan-1-one;
143 N-((1H-indol-6-yl)methyl)-N-methyl-2-(4-phenyl-4-(pyrrolidin-1-yl)piperidin-1-yl)ethanamine;
144 1-(2-(((1H-indol-6-yl)methyl)(methyl)amino)ethyl)-4-butyl-N,N-dimethylpiperidin-4-amine;
145 3-(((1H-indol-6-yl)methyl)amino)-1-(4-(dimethylamino)-4-phenylpiperidin-1-yl)propan-1-one;
146 2-(((1H-indol-5-yl)methyl)(methyl)amino)-1-(4-(dimethylamino)-4-phenylpiperidin-1-yl)-3-methylbutan-1-one;
147 2-(((1H-indol-5-yl)methyl)(methyl)amino)-1-(4-(dimethylamino)-4-(thiophen-2-yl)piperidin-1-yl)-2-phenylethanone;
148 (1-((1H-indol-5-yl)methyl)piperidin-3-yl)(4-(dimethylamino)-4-phenylpiperidin-1-yl)methanone;
149 2-(((1H-indol-6-yl)methyl)(methyl)amino)-1-(4-(dimethylamino)-4-phenylpiperidin-1-yl)-3-methylbutan-1-one;
150 2-(((1H-indol-6-yl)methyl)(methyl)amino)-1-(4-(dimethylamino)-4-(thiophen-2-yl)piperidin-1-yl)-2-phenylethanone;
151 (1-((1H-indol-3-yl)methyl)piperidin-3-yl)(4-(dimethylamino)-4-phenylpiperidin-1-yl)methanone;
152 (1-((1H-indol-6-yl)methyl)piperidin-3-yl)(4-(dimethylamino)-4-phenylpiperidin-1-yl)methanone;
153 N-((5-bromo-1H-indol-3-yl)methyl)-N-methyl-2-(4-phenyl-4-(pyrrolidin-1-yl)piperidin-1-yl)ethanamine;
154 1-(2-(((5-bromo-1H-indol-3-yl)methyl)(methyl)amino)ethyl)-4-butyl-N,N-dimethylpiperidin-4-amine;
155 (1-((5-bromo-1H-indol-3-yl)methyl)piperidin-3-yl)(4-(dimethylamino)-4-phenylpiperidin-1-yl)methanone;
156 (4-(dimethylamino)-4-phenylpiperidin-1-yl)(1-((2-methyl-1H-indol-3-yl)methyl)piperidin-3-yl)methanone;
157 1-(2-(((1H-indol-7-yl)methyl)(methyl)amino)ethyl)-4-butyl-N,N-dimethylpiperidin-4-amine;
158 (1-((1H-indol-7-yl)methyl)piperidin-3-yl)(4-(dimethylamino)-4-phenylpiperidin-1-yl)methanone;
159 N-((1H-indol-4-yl)methyl)-N-methyl-2-(4-phenyl-4-(pyrrolidin-1-yl)piperidin-1-yl)ethanamine;
160 1-(2-(((1H-indol-4-yl)methyl)(methyl)amino)ethyl)-4-butyl-N,N-dimethylpiperidin-4-amine;
161 (1-((1H-indol-4-yl)methyl)piperidin-3-yl)(4-(dimethylamino)-4-phenylpiperidin-1-yl)methanone;
162 3-(((5-bromo-1H-indol-3-yl)methyl)amino)-1-(4-(dimethylamino)-4-phenylpiperidin-1-yl)propan-1-one;
163 3-(((5-bromo-1H-indol-3-yl)methyl)amino)-1-(4-(dimethylamino)-4-(thiophen-2-yl)piperidin-1-yl)-3-phenylpropan-1-one;
164 3-(((1H-indol-3-yl)methyl)amino)-1-(4-(dimethylamino)-4-(thiophen-2-yl)piperidin-1-yl)-3-phenylpropan-1-one;
165 3-(((1H-indol-5-yl)methyl)amino)-1-(4-(dimethylamino)-4-(thiophen-2-yl)piperidin-1-yl)-3-phenylpropan-1-one;
166 (1-((1H-indol-5-yl)methyl)indolin-3-yl)(4(dimethylamino)-4-phenylpiperidin-1-yl)methanone;
167 1-(4-(dimethylamino)-4-phenylpiperidin-1-yl)-3-(((2-methyl-1H-indol-3-yl)methyl)amino)propan-1-one;
168 1-(4-(dimethylamino)-4-(thiophen-2-yl)piperidin-1-yl)-3-(((2-methyl-1H-indol-3-yl)methyl)amino)-3-phenylpropan-1-one;
169 3-(((1H-indol-6-yl)methyl)amino)-1-(4-(dimethylamino)-4-(thiophen-2-yl)piperidin-1-yl)-3-phenylpropan-1-one;
170 (1-((1H-indol-6-yl)methyl)indolin-3-yl)(4-(dimethylamino)-4-phenylpiperidin-1-yl)methanone;
171 3-(((1H-indol-7-yl)methyl)amino)-1-(4-(dimethylamino)-4-phenylpiperidin-1-yl)propan-1-one;
172 2-(((1H-indol-7-yl)methyl)amino)-1-(4-(dimethylamino)-4-(thiophen-2-yl)piperidin-1-yl)ethanone;

173 3-(((1H-indol-7-yl)methyl)amino)-1-(4-(dimethylamino)-4-(thiophen-2-yl)piperidin-1-yl)-3-phenylpropan-1-one;
174 3-(((1H-indol-4-yl)methyl)amino)-1-(4-(dimethylamino)-4-(thiophen-2-yl)piperidin-1-yl)-3-phenylpropan-1-one;
175 (1-((1H-indol-4-yl)methyl)indolin-3-yl)(4dimethylamino)-4-phenylpiperidin-1-yl)methanone;
176 (4-(dimethylamino)-4-phenylpiperidin-1-yl)(1-((6-methoxy-1,2-dimethyl-1H-indol-3-yl)methyl)piperidin-3-yl)methanone;
177 (4-(dimethylamino)-4-phenylpiperidin-1-yl)(1-((2-(4-fluorophenyl)-1H-indol-3-yl)methyl)piperidin-3-yl)methanone;
178 1-(2-(((5-chloro-1H-indol-3-yl)methyl)amino)ethyl)-N,N-dimethyl-4-(thiophen-2-yl)piperidin-4-amine;
179 1-(2-(((1H-indol-3-yl)methyl)amino)ethyl)-N,N-dimethyl-4-(thiophen-2-yl)piperidin-4-amine;
180 1-(2-(((6-isopropyl-1H-indol-3-yl)methyl)(methyl)amino)ethyl)-N,N-dimethyl-4-phenylpiperidin-4-amine;
181 1-(2-(((1H-indol-6-yl)methyl)(methyl)amino)ethyl)-N,N-dimethyl-4-phenylpiperidin-4-amine;
182 1-(2-(((5-chloro -1H-indol-3-yl)methyl)(methyl)amino)ethyl)-N,N-dimethyl-4-phenylpiperidin-4-amine;
183 1-(2-(((5-chloro -1H-indol-3-yl)methyl)(methyl)amino)ethyl)-N,N-dimethyl-4-phenylpiperidin-4-amine;
184 1-(2-(((1H-indol-6-yl)methyl)(methyl)amino)ethyl)-N,N-dimethyl-4-phenylpiperidin-4-amine;
185 1-(2-(((5-bromo-1H-indol-3-yl)methyl)(methyl)amino)ethyl)-N,N-dimethyl-4-phenylpiperidin-4-amine;
186 1-(2-(((1H-indol-3-yl)methyl)(methyl)amino)ethyl)-N,N-dimethyl-4-phenylpiperidin-4-amine;
187 1-(2-(((1H-indol-3-yl)methyl)(methyl)amino)ethyl)-N,N-dimethyl-4-phenylpiperidin-4-amine;
188 1-(2-(((5-methoxy-1H-indol-3-yl)methyl)amino)ethyl)-N,N-dimethyl-4-(thiophen-2-yl)piperidin-4-amine;
189 1-(2-(((1,2-dimethyl-1H-indol-3-yl)methyl)(methyl)amino)ethyl)-N,N-dimethyl-4-phenylpiperidin-4-amine;
190 1-(2-(((5-methoxy-1H-indol-3-yl)methyl)(methyl)amino)ethyl)-N,N-dimethyl-4-phenylpiperidin-4-amine;
191 1-(2-(((5-methoxy-1H-indol-3-yl)methyl)(methyl)amino)ethyl)-N,N-dimethyl-4-phenylpiperidin-4-amine;
192 1-(2-(((5-methoxy-1H-indol-3-yl)methyl)(methyl)amino)ethyl)-N,N-dimethyl-4-phenylpiperidin-4-amine;
193 1-(2-(((1-benzyl-5-methoxy-2-methyl-1H-indol-3-yl)methyl)(methyl)amino)ethyl)-N,N-dimethyl-4-phenylpiperidin-4-amine;
194 1-(2-(((1H-indol-4-yl)methyl)(methyl)amino)ethyl)-N,N-dimethyl-4-phenylpiperidin-4-amine; and
195 1-(2-(((1H-indol-4-yl)methyl)(methyl)amino)ethyl)-N,N-dimethyl-4-phenylpiperidin-4-amine;

said compound optionally being in the form of a racemic mixture, or in the form of individual enantiomers or diastereomers, or in the form of mixtures of enantiomers and/or diastereomers in any mixing ratio;

or a base and/or salt of said compound or one of said forms with a physiologically compatible acid or cation.

11. Process for the preparation of a substituted indole derivative according to claim 1,

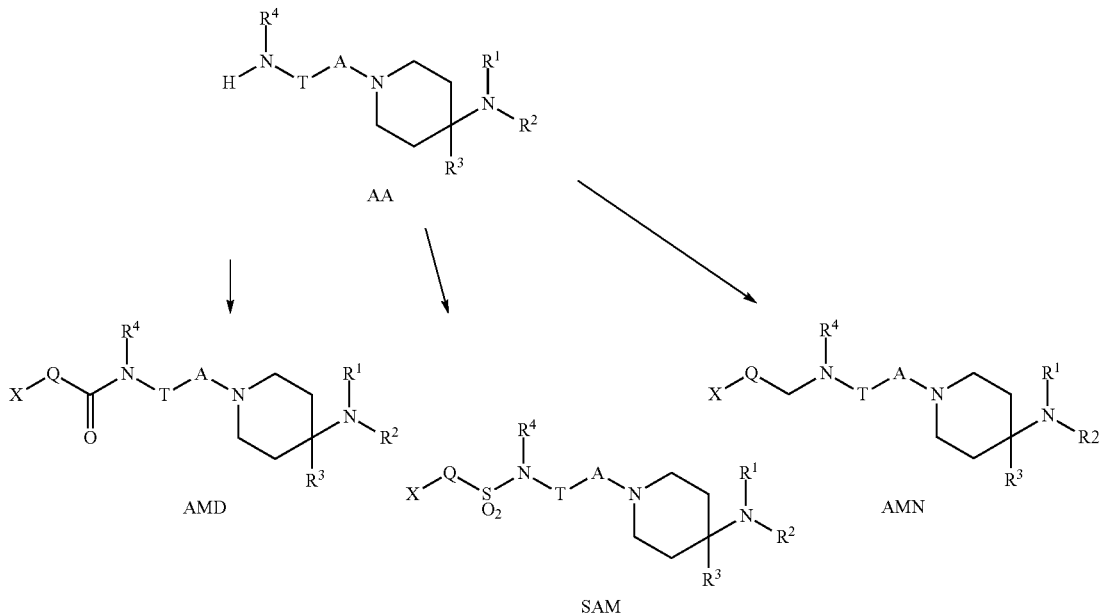

comprising reacting a compound having the formula AA in at least one solvent with an acid having the formula X-Q-CO$_2$H, wherein X and Q have the meanings given in claim 1, with addition of at least one coupling reagent, optionally in the presence of at least one inorganic base, and optionally with addition of 4-(dimethylamino)pyridine or 1-hydroxybenzotriazole, to form a compound having the formula AMD, or reacting a compound having the formula AA with a sulfonyl chloride having the formula X-Q-SO$_2$Cl, wherein X and Q have the meanings given in claim 1, in at least one organic solvent, in the presence of an excess of a base to form a compound having the formula SAM, or reacting a compound having the formula AA with an aldehyde having the formula X-Q-CHO, wherein X and Q have the meanings given in claim 1, in at least one organic solvent, with addition of at least one reducing agent, optionally in the presence of at least one acid to form a compound having the formula AMN.

12. A pharmaceutical composition comprising a therapeutically effective amount of at least one substituted indole derivative according to claim 1 and optionally suitable additives and/or auxiliary substances and/or optionally further active ingredients.

13. A method of treating pain in a patient in need thereof, comprising administering to said patient an effective amount therefore of a substituted indole derivative according to claim 1.

14. The method according to claim 13, wherein the pain is selected from the group consisting of acute, neuropathic and chronic pain.

* * * * *